US010590427B2

(12) United States Patent
Gasser et al.

(10) Patent No.: US 10,590,427 B2
(45) Date of Patent: Mar. 17, 2020

(54) RECOMBINANT HOST CELL FOR EXPRESSING PROTEINS OF INTEREST

(71) Applicants: Boehringer Ingelheim RCV GmbH & Co KG, Vienna (AT); Validogen GmbH, Grambach (AT); Lonza Ltd., Visp (CH)

(72) Inventors: Brigitte Gasser, Vienna (AT); Diethard Mattanovich, Vienna (AT); Markus Buchetics, Vienna (AT)

(73) Assignees: Boehringer Ingelheim RCV GmbH & Co KG, Vienna (AT); Lonza Ltd., Visp (CH); Validogen GmbH, Grambach (AT)

( * ) Notice: Subject to any disclaimer, the term of this patent is extended or adjusted under 35 U.S.C. 154(b) by 185 days.

(21) Appl. No.: 15/304,504

(22) PCT Filed: Apr. 16, 2015

(86) PCT No.: PCT/EP2015/058225
§ 371 (c)(1),
(2) Date: Oct. 14, 2016

(87) PCT Pub. No.: WO2015/158800
PCT Pub. Date: Oct. 22, 2015

(65) Prior Publication Data
US 2017/0044557 A1 Feb. 16, 2017

(30) Foreign Application Priority Data
Apr. 17, 2014 (EP) .................... 14165188

(51) Int. Cl.
C12N 15/81 (2006.01)
C12P 21/00 (2006.01)
(52) U.S. Cl.
CPC ........... *C12N 15/815* (2013.01); *C12N 15/81* (2013.01); *C12P 21/005* (2013.01)
(58) Field of Classification Search
None
See application file for complete search history.

(56) References Cited

U.S. PATENT DOCUMENTS 6,344,341 B1 * 2/2002 Keranen ................ C07K 14/39
435/254.21

FOREIGN PATENT DOCUMENTS

WO    WO 2015/158808 A2    10/2015

OTHER PUBLICATIONS

Kim et al., CUrr. Genet. 44:261-267 (Year: 2004).*
Nathan et al., Proc. Natl. Acad. USA 96:1409-1414 (Year: 1999).*
Silberstein et al., J. Cell. Biol., 143 (4): 921-933 (Year: 1998).*
Gasser et al., "*Pichia pastoris*: Protein Production Host and Model Organism for Biomedical Research," Future Microbiol. (2013), 8(2):191-208, Future Medicine Ltd.
Heiss et al., "Identification and Deletion of the Major Secreted Protein of *Pichia pastoris*," Appl. Microbiol. Biotechnol. (2013), 97:1241-1249, Springer-Verlag.
Payne et al., "A Mutation in the *Bordetella bronchiseptica* bvgS Gene Results in Reduced Virulence and Increased Resistance to Starvation, and Identifies a New Class of Bvg-Regulated Antigens," Molecular Microbiology (1997), 24(4):671-685, Blackwell Science Ltd.
Zhang et al., "Enhanced Secretion of Heterologous Proteins in *Pichia pastoris* Following Overexpression of *Saccharomyces cerevisiae* Chaperone Proteins," Biotechnol. Prog. (2006), 22:1090-1095, American Chemical Society and American Institute of Chemical Engineers.
Chinese Office Action and Search Report dated Jan. 25, 2019, regarding CN 201580032885.6.
Japanese Office Action dated Jan. 29, 2019, regarding JP 2016-562864.
Payne, T. et al.: "Modulation of Chaperone Gene Expression in Mutagenized *Saccharomyces cerevisiae* Strains Developed for Recombinant Human Albumin Production Results in Increased Production of Multiple Heterologous Proteins"; Applied & Environmental Microbiology, vol. 74, No. 24, Dec. 2008, pp. 7759-7766.

* cited by examiner

Primary Examiner — Nancy A Treptow
(74) Attorney, Agent, or Firm — DLA Piper LLP (US)

(57) ABSTRACT

The present invention is in the field of recombinant biotechnology, in particular in the field of protein expression. The invention generally relates to a method of expressing a protein of interest (POI) from a host cell. The invention relates particularly to improving a host cell's capacity to express and/or secrete a protein of interest and use of the host cell for protein expression. The invention also relates to cell culture technology, and more specifically to culturing cells to produce desired molecules for medical purposes or food products.

16 Claims, 10 Drawing Sheets
Specification includes a Sequence Listing.

HP1 ("56") amino acid sequence (SEQ ID NO: 4)

MSSDAVEQLENFQLIKFDRFDPSTQSTIRIARSPKPIPVKVVIVGDGGCGKTCLLNVFATGTFPEAYVPTIIENV
VITLVTPTGQIAAVTLWDTAGQEEYDRLRPLSYSDVDVVLLCYSIDNLSTFHNVADKWYPEVAHFCPNTPIILVG
TKSDMRRHQKSQPHFVSPQDSSQLARQMGAVMNIECSAKEVSNVNIVFDAAVSYCLSNSRPKTRGDNDNNRSNRR
LSRAKRASMFIRGKDVSSTSGNSREELVEYDQDGLAIIPDRKKRKCSII

HP2 ("2") amino acid sequence (SEQ ID NO: 1)

MLNKLFIAILIVITAVIGETTTSSTTASLSESPTLVWVTGTDASGRLATTQSAYTQQFSQLYSSIASPSSGSIGL
GTIQGTVGIVRTYETITLAS

HP3 ("3") amino acid sequence (SEQ ID NO: 2)

MSTAIPGGQRTLAKRRAANLDKKQDEPTSARSAGAGGSSSTMLKLYTDEAQGLKVDPLIVLVLAVGFIFSVIGLH
VVAKLTGKLIN

HP4 ("27") amino acid sequence (SEQ ID NO: 3)

MTPRSHIFFDISINNQPAGRIIFELFNDIVPKTAENFRALSTGEKGIGKSGKPLHYKGSTFHRIIKDFMVQGGDF
TNGNGTGGESIYGEKFEDENFQLTHDKPFLLSMANAGPGTNGSQFFITTVPTPHLDNKHVVFGKVIAGKATVRKI
ERNSEGEAPIEPVVIEDCGELPEDADLTISDETGDKYEEVLKDNENIDIDDFEQVYQAITEIKELGTKYFKNGDT
KIAFEKYQKAANYLLEYIPSDLSEEQSSKLELLKTSVFSNVALAGLKVSKFKDTIKYATLVIEDESADAKAKSKG
YYRRGSAYSSLKDEDSAISDFQKALELSPGDPAISQSLQRTTKARKDRLAKEKAALSKFFE

HP5 ("4") amino acid sequence (SEQ ID NO: 5)

MTNWKAILTPAQYQVLRLGGTERPYTGQYVNFKKNGTYLCSGCQTPLYKSGTKFDSSCGWPAFYEALPGAVKRIE
DNSLGMRRIEIRCSKCDGHLGHVFEGEGFDTPTDSRHCVNSISLKFQGEEEN

HP6 ("54") amino acid sequence (SEQ ID NO: 7)

MSHLLLRDSFWGRTIYHLSKHRYFSFPEEKDGFIAPEKYYLNMDQVSIHAESEKNIVEGLVDTSNSSLEEVKTTR
VIVDWDEYDQKENPQNWSSLLKCFVVFEVGILTVAVYMGSAIYTPGIEDIMRDLNVSRTVATLPLTLFVIGYAVG
PMIFSPMSEHPAIGRTTIYVWTLFIFAILQIPTALTTNIAGFCILRFIGGFFASPALATGPASVGDVIAIPHLPV
GLGLWSICAVCGPSLGPLFGAIFSQLVSWRWCFWFLLITSGTLFIVLGFTLPETYVPTLLYRKARRLRALTKNEL
IISKGELDIQDRTAKEVLIECLWRPVDISFRDPVVLMINLYISMVYSIWYIWFEAFPIVFLEIYGFSLIGMGASF
AGILIGVLICSACYCYACHVTFARRIIANETIHPEFFVPGAIIGGCIMPTGIFILGWTATKSVHWIVPIIGSGLF
AAGGYLIFQTLFNYLAMSFPRYMASAFAGNDLFRSFSASVFPLFGHALYANLGSEKFPVGWGSSVLGFITVAMIA
IPVTFMRYGPRLRANSRYAGP

HP7 ("55") amino acid sequence (SEQ ID NO: 8)

MTDYVTSKRPDNVLNWTSIHVSSWIGETIPEIDPSLLQNFLEHDIAGDVLPYLKSEDLKEIGINELKHRISIKKN
IHELLVSNEKHIDTSILSDTATELGTLILTNKFITQMANRKNVVDDSTHHSNNRRLTEQFNKLRDLLPIFKWIK
ETQPLPTPENTHFANMGSVPASPVEHTSGESTLSNPSLSTINAGEGVNSAVAGQSLGRKPTLSSRRQSHALSPTG
EHLNVSSSSPSTGNFETLNGERPNLRSASSGSQEHTENELLKPLRVKADEPCYKVIQNAMKRHGLSVDDWRKYAL
VICYGDEERVLGLHEKPGSIFKELKDQKQNPAIMLRQIDTNNDDQNHIETPGGRL

FIG. 1A

HP8 ("40") amino acid sequence (SEQ ID NO: 6)

MTTNGQKRQK TRKPLLINAF VMGCAGLQNP GLWKHPKDSS HRFNQIDHWT YLAKLAEKGK
FNALFIADVL GGYDVYKGPE NLATPAVAGA QWPVTEPSAV VSAMAAVTTN LAFGVTFSTI
SEAPYHFARR LSTLDHLTKG RIGWNVVSSY LESAARNLLN GEKLDEHDQR YLKAEEYIQI
VYELLLSSWR DDAVVLDKKA GVYTDPTRFR KINFEGKFFK VPGPHIVDPT PQRLPVILQA
GTSKVGKEFA AKHAEIVFVI SFSPDDLKPK IAEVRQLAKE KFGRNHDDIK FVALATPVIG
ATHELAEEKY QELLSYGDIE GAQALFGGWT GIDLSQYGED EELGNVSSNA MRGAVQNWTK
AIPNEKRWTR KVIAKQITVG GLGPAFVGTP EEIADELEHW SDHAGLDGFN FTYAVNPLSF
EEIVEDLIPV LQRRGLAQKE YPNPETGSTF RKNLFGTDFV PSTHPAYNLR WRAGVSKEEF
EKSLNATTNW YSSFARSGAL GELHNTCRIL YLQIVKYKYR LRVRSEGNSI PFAKMTKENE
AKRQKTSQPK AKKQLIINAF MSGSSGNQSP GLWSYPGDKS TEYTTLDYWV ELAQKLEKAK
FHSIFIADVL GGYDVYNGPG NYSAAAKSGA QFPMIEPSAA VTAMAAATKS ITFGVTFSTI
SEAPYHFARR LGTLDLLTNG RVGWNIVSSY LDSAARNLLN GEPLPLHADR YKRAEEFLQV
VYRLFLSSWR DDAYKLDKKT RTFADPKLIR TIDHVGEFFN VPGPQFLPPT PQRLPLILQA
GTSKVGMDYA AKHAEVVFLA SFDPESLQEK IKTVRDIAET KYNRPRDSIK FLILITVVIA
DTHEDAVKRY EDLASYADLE GAQALFSGWT GIDIGKYGED EPLEHVESNA IKSHVKNWTK
FKDNKPRARK DIAKQIGVGG SGPLLVGSVQ EIADELERWA EVSDLDGFNF AYADYPQTFD
DIIEKLLPEL NKRGVFWDDY KIPGGTFRES VFGRKFVDKD HPAYDLRWRS DQTREEFEKK
LAELEKK

HP9 ("60") amino acid sequence (SEQ ID NO: 9)

MRFSNVVLTAIAAAGVQADEALYTVFYNDVTENAQEYLSYIQANTAAGFTDLLSLYTELATYTDDSYTSIFTEED
FPASELSSFVVNLPWYSSRIEPQVAAAETGESEEESETGESEEESETGEETETETGSESESESESETSATGTGTG
TSASESAETETSTDAAVSIDHPKSTLLMGLTAAVVSITFGVFAL

HP10 ("34") amino acid sequence (SEQ ID NO: 162)

MSSFRVLDLV KPFTPFLPEV ISPERKVPFQ QKLMWTGVTL LIFLVMSEIP LYGITSSDSS
DPLFWLRMML ASNRGTLMEL GISPIVTSGM VFQLLQGIQI LDVNMENKAD RELFQTAQKV
FAILLSIGQA TVYVLTGMYG PPGELGVGVC LLLVLQLVFA GIVVILLDEL LQKGYGLGSG
ISLFMATNIC EQIFWKTFAP TTVNRGRGKE FEGAFISFFH LILTKKDKKR ALLESFYRDN
APNMFQVIAT LVVFFTVVYL QGFRLEIPVK STRQRGPYGT YPIRLFYTSN MPIMLQSALT
SNIFIISQML YSHFPDNAFV KLIGTWEAQP GSAQLFAASG LAYYMQPPMS LSQALLDPIK
TVVYVVFVLT TCAIFSKTWI EISGSSPRDV AKQFKDQGLV IAGHRDATVY KELKKIIPTA
AAFGGATIGA LSVVSDLLGT LGSGTSILLA VTTIYGYYEL AVKEGGFSKG GPSGFVDL

FIG. 1B

HP1 polynucleotide sequence (SEQ ID NO: 16)

ATGTCGTCTGATGCTGTGGAGCAACTTGAAAACTTCCAGTTGATCAAGTTCGACAGATTCGATCCTTCAACGCAA
TCGACTATCAGAATAGCGCGATCTCCCAAACCAATTCCAGTCAAGGTTGTGATAGTGGGAGATGGTGGATGTGGA
AAGACATGTCTTCTCAATGTCTTTGCCACTGGAACGTTTCCTGAGGCGTATGTCCCCACAATCATAGAAAATGTG
GTTATTACATTGGTGACCCCAACTGGCCAGATAGCTGCCGTTACTCTGTGGGATACTGCAGGGCAAGAAGAGTAC
GACAGATTGAGACCCCTAAGCTACTCCGACGTTGACGTGGTCTTGCTGTGCTACAGCATAGACAATCTGTCCACC
TTTCATAATGTGGCCGACAAATGGTACCCAGAAGTGGCACATTTTTGTCCAAACACACCGATCATCTTGGTAGGT
ACCAAATCTGATATGCGGCGTCATCAGAAGAGTCAGCCGCACTTTGTATCTCCCCAGGATTCGTCGCAGTTGGCA
AGGCAGATGGGGGCAGTGATGAACATCGAGTGTTCTGCGAAGGAGGTTTCAAACGTCAATATCGTTTTTGATGCT
GCTGTGTCGTACTGTTTGAGTAACAGCAGGCCCAAGACCAGAGGGGATAATGACAACAATAGGAGTAACAGACGG
CTAAGTAGAGCCAAGCGAGCCAGCATGTTTATAAGGGGTAAGGATGTTAGCTCAACGTCAGGAAACTCTCGGGAA
GAACTTGTTGAATACGATCAAGATGGGTTGGCAATAATACCGGACAGAAAGAAACGCAAATGTAGCATTATTTGA

HP2 polynucleotide sequence (SEQ ID NO: 13)

ATGTTAAACAAGCTGTTCATTGCAATACTCATAGTCATCACTGCTGTCATAGGCGAGACGACTACGTCATCTACC
ACTGCCAGTCTCTCCGAAAGCCCTACTCTGGTTTGGGTGACTGGCACTGATGCAAGTGGGAGATTGGCAACTACA
CAGTCTGCTTACACTCAACAGTTTTCACAGTTATACTCATCCATAGCATCTCCATCAAGTGGTAGCATAGGCCTG
GGTACTATCCAGGGGACTGTTGGAATTGTCAGAACATATGAGACAATTACCCTTGCCAGCTAA

HP3 polynucleotide sequence (SEQ ID NO: 14)

ATGTCTACAGCAATTCCAGGAGGACAGAGAACGTTAGCTAAAAGAAGAGCAGCAAACTTGGATAAGAAACAGGAT
GAACCAACCTCCGCCAGATCTGCCGGTGCTGGAGGTTCTTCGTCTACCATGCTAAAGTTGTACACAGACGAGGCC
CAAGGTTTGAAAGTTGATCCTTTAATTGTTCTTGTTCTTGCTGTTGGTTTCATTTTCAGTGTCATTGGTTTGCAC
GTTGTTGCTAAGCTGACAGGAAAGTTGATCAACTAA

HP4 polynucleotide sequence (SEQ ID NO: 15)

ATGACTCCCCGTTCTCATATTTTCTTTGACATCTCCATCAACAACCAGCCAGCTGGCAGAATAATCTTTGAGCTC
TTCAATGACATTGTTCCTAAGACAGCAGAGAATTTTAGAGCTTTATCTACTGGTGAGAAAGGTATAGGTAAGTCT
GGGAAACCATTGCACTACAAGGGTTCTACTTTCCATAGGATCATTAAGGATTTTATGGTACAAGGTGGTGACTTT
ACCAACGGTAACGGTACTGGAGGCGAATCCATATATGGAGAAAAATTTGAAGATGAAAATTTCCAATTGACTCAT
GACAAACCGTTCCTTCTCTCTATGGCAAACGCTGGACCAGGAACTAATGGATCCCAGTTTTTTATCACCACCGTT
CCTACTCCTCATCTGGATAACAAGCATGTAGTGTTTGGAAAAGTAATTGCTGGTAAAGCCACAGTTAGAAAGATT
GAAAGAAACTCCGAAGGTGAAGCTCCAATTGAACCCGTTGTCATTGAGGACTGTGGTGAACTTCCAGAAGACGCA
GATTTGACCATCTCCGACGAGACTGGAGACAAGTATGAGGAAGTTCTGAAAGATAATGAGAACATAGACATCGAT
GACTTTGAACAGGTCTACCAGGCCATCACTGAAATCAAAGAATTGGGTACAAAGTATTTCAAAAATGGTGACACC
AAAATCGCCTTCGAAAAGTATCAAAAGGCTGCTAATTATTTGCTGGAATACATACCATCAGATTTATCAGAGGAA
CAGAGCTCTAAGTTGGAGCTGCTAAAAACATCTGTCTTCTCCAACGTGGCATTGGCTGGACTGAAAGTTTCCAAG
TTCAAAGACACGATTAAGTATGCCACATTGGTCATTGAGGATGAATCTGCGGATGCAAAGGCCAAGTCCAAGGC
TACTACCGTAGAGGAAGTGCTTACAGCTCACTGAAAGACGAAGATTCAGCCATCTCAGATTTCCAGAAAGCACTT
GAATTATCCCCAGGTGATCCTGCAATTAGCCAATCTCTACAAAGAACCACGAAGGCCAGAAAAGACCGTCTTGCC
AAAGAGAAAGCTGCTTTGTCTAAGTTCTTTGAGTAG

FIG. 1C

HP5 polynucleotide sequence (SEQ ID NO: 17)

ATGACTAACTGGAAAGCGATATTGACTCCCGCTCAATACCAAGTCCTCCGTTTGGGCGGAACAGAAAGACCGTAT
ACCGGACAGTATGTGAACTTCAAGAAAAATGGAACCTACTTGTGTAGTGGGTGTCAAACTCCGCTTTACAAAAGT
GGCACAAAATTTGATTCATCTTGTGGTTGGCCTGCATTCTATGAAGCATTACCTGGAGCAGTTAAACGAATAGAA
GACAATTCGCTTGGAATGCGAAGAATAGAAATCAGATGCTCCAAATGTGATGGACATCTTGGCCATGTTTTTGAG
GGTGAGGGATTTGACACTCCAACAGATTCCAGACATTGTGTCAACAGCATCAGCCTAAAATTTCAAGGTGAAGAA
GAGAACTAA

HP6 polynucleotide sequence (SEQ ID NO: 19)

ATGTCTCATCTATTACTGCGTGACAGCTTTTGGGGAAGGACCATCTACCATCTGAGTAAACACAGGTATTTCTCT
TTTCCTGAAGAGAAAGATGGTTTCATTGCTCCTGAAAAGTACTACCTGAATATGGACCAAGTATCGATACATGCT
GAATCTGAGAAAAATATAGTGGAAGGTTTGGTAGACACTTCAAATTCTTCGTTGGAGGAAGTAAAGACCACTAGA
GTCATAGTCGACTGGGATGAATATGATCAGAAAGAAAATCCCCAAAACTGGAGCTCGCTTTTAAAGTGCTTCGTT
GTTTTTGAAGTGGGAATCTTAACCGTAGCTGTTTATATGGATCTGCAATTTACACTCCCGGTATAGAAGATATT
ATGAGAGATCTCAATGTTAGCAGAACGGTGGCAACACTTCCATTAACCTTGTTTGTGATTGGATACGCTGTGGGT
CCAATGATATTCTCCCCCATGTCTGAGCATCCCGCTATCGGAAGGACAACGATATATGTGTGGACCCTGTTCATA
TTTGCTATACTACAAATCCCAACGGCCCTGACCACTAACATTGCTGGATTTTGCATTTTGAGGTTTATTGGAGGG
TTTTTTGCGTCACCAGCATTAGCTACAGGTCCAGCTTCTGTAGGTGATGTTATTGCAATCCCGCACTTGCCTGTA
GGGTTAGGCCTTTGGAGTATCTGTGCTGTTTGTGGTCCTTCTCTAGGACCACTTTTTGGAGCCATATTTTCCCAA
CTTGTGAGTTGGAGGTGGTGCTTCTGGTTTCTGTTAATTACCTCTGGGACACTATTTATAGTTCTTGGCTTCACT
TTACCAGAAACGTATGTACCAACCCTTCTTTACAGAAAGGCTAGGAGGCTACGAGCATTAACAAAAAACGAACTG
ATTATCAGCAAAGGGGAGTTAGATATTCAGGACAGAACTGCCAAGGAAGTTTTGATTGAATGCTTATGGAGGCCA
GTCGACATATCATTCAGAGACCCCGTTGTCTTGATGATAAATCTTTACATTTCAATGGTTTATTCTATTTGGTAC
ATTTGGTTTGAAGCGTTTCCTATTGTATTCTTAGAGATATATGGATTCAGCCTTATTGGAATGGGAGCTAGTTTT
GCCGGAATCTTAATTGGTGTCTTAATATGCTCTGCGTGCTATTGCTATGCGTGTCATGTTACTTTTGCAAGAAGA
ATAATTGCAAACGAAACCATTCATCCTGAGTTCTTTGTACCGGGCGCTATTATTGGAGGTTGCATAATGCCCACT
GGAATCTTTATTTTGGGATGGACTGCCACCAAAAGTGTCCACTGGATTGTACCTATAATAGGTAGCGGTTTATTT
GCTGCTGGTGGTTATCTCATTTTCCAGACACTCTTCAACTACCTTGCAATGTCTTTCCCTAGATACATGGCATCA
GCTTTTGCCGGAAATGATCTTTTCAGGTCCTTTTCTGCCAGTGTTTTCCCACTGTTTGGACATGCACTATATGCC
AACTTGGGATCCGAAAAGTTCCCTGTTGGTTGGGGTTCTTCTGTACTGGGGTTCATCACTGTTGCAATGATCGCA
ATTCCAGTAACTTTCATGAGATATGGTCCAAGATTGCGTGCAAATTCTAGATATGCCGGGCCATGA

HP7 polynucleotide sequence (SEQ ID NO: 20)

ATGACGGACTATGTCACTTCTAAGCGGCCAGATAACGTGCTCAATTGGACAAGTATTCATGTATCGTCCTGGATA
GGGGAGACTATTCCTGAGATCGATCCAAGTCTACTCCAAAATTTTTTAGAACATGACATTGCGGGAGATGTTCTA
CCCTACTTGAAGTCTGAAGATCTGAAGGAAATTGGGATCAACGAGCTCAAGCACAGAATCTCTATAAAAAAGAAC
ATTCATGAACTTCTTGTGAGCAATGAAAAGCACATTGATACCAGTATTCTATCAGACACCGCTACCGAGCTAGGA
ACTTTGATACTGACTAATAAATTCATAACCCAGATGGCGAACAGAAAGAATGTTGTAGATGATTCCACTCATCAT
TCGAATAACAGAAGGCTCACTGAACAGTTTAATAAGCTTCGCAAAGATCTTTTGCCGATATTCAAATGGATCAAG
GAGACCCAACCATTACCCACTCCAGAGAATACACATTTCGCAAATATGGGTTCAGTACCAGCATCTCCTGTGGAG
CATACTTCAGGTGAGTCAACATTGTCTAACCCCAGTCTAAGCACCATCAATGCTGGCGAAGGAGTGAACTCTGCA
GTTGCAGGGCAATCTCTCGGGAGGAAACCTACATTATCCTCCAGAAGACAATCACATGCTTTGTCTCCAACTGGT
GAACACCTGAATGTGTCATCATCATCTCCTTCGACGGGGAATTTTGAAACTCTGAATGGAGAAAGACCCAATCTT
AGATCTGCTTCGTCAGGATCACAGGAACATACTGAGAACGAACTATTGAAGCCGTTGAGAGTTAAAGCAGATGAG
CCTTGCTATAAGGTGATTCAGAATGCCATGAAAAGACATGGCTTATCGGTAGATGATTGGCGCAAGTATGCTTTG
GTCATCTGCTATGGAGATGAAGAACGAGTACTAGGCTTACATGAAAAACCTGGGAGTATCTTCAAGGAACTCAAA
GATCAGAAACAGAATCCTGCAATCATGCTTCGTCAAATTGACACTAATAATGACGATCAGAACCATATTGAAACC
CCTGGAGGGAGATTATGA

FIG. 1D

HP8 polynucleotide sequence (SEQ ID NO: 18)

ATGACTACAAACGGCCAGAAAAGACAAAAAACTCGCAAACCACTTTTGATCAACGCATTTGTCATGGGAT
GTGCTGGGTTACAGAATCCTGGTTTATGGAAGCATCCCAAGGACTCATCCCATAGATTTAATCAGATTGA
TCACTGGACTTATTTGGCCAAGTTAGCCGAAAAGGGGAAGTTTAATGCGCTCTTCATTGCCGACGTCTTG
GGTGGCTATGATGTCTACAAAGGACCTGAGAATTTAGCCACTCCTGCTGTGGCTGGAGCCCAGTGGCCTG
TCACCGAGCCCAGTGCTGTGGTCTCCGCCATGGCTGCAGTCACAACTAACTTGGCGTTTGGAGTGACGTT
CTCTACTATCAGCGAAGCCCCCTATCATTTTGCCAGAAGACTGTCCACTTTAGACCACTTGACCAAGGGT
AGAATAGGATGGAATGTTGTTTCATCTTACTTGGAGAGTGCTGCTCGTAACCTCTTGAATGGTGAAAAAT
TGGACGAGCATGACCAAAGATACTTGAAAGCTGAAGAGTACATTCAAATAGTTTATGAGCTGTTGTTATC
GTCTTGGAGAGATGATGCAGTAGTTTTAGACAAGAAAGCTGGTGTTTATACTGACCCAACAAGATTTCGA
AAGATCAACTTTTGAAGGTAAATTTTTCAAAGTTCCGGGACCACATATTGTTGACCCCACCCCTCAAAGAC
TGCCTGTGATTCTTCAAGCTGGTACTTCTAAAGTTGGTAAGGAGTTTGCTGCTAAGCATGCCGAGATTGT
GTTTGTCATTTCATTTTCTCCAGATGATTTGAAACCCAAGATTGCAGAAGTTCGTCAACTGGCCAAAGAA
AAGTTTGGTAGAAACCACGACGATATTAAGTTTGTTGCCCTTGCAACCCCTGTTATTGGAGCCACACATG
AACTAGCTGAAGAAAAGTACCAAGAGTTACTAAGTTATGGTGATATTGAAGGTGCTCAAGCCTTATTTGG
AGGGTGGACTGGCATTGACCTCTCTCAATATGGCGAAGATGAAGAACTAGGAAATGTTAGTTCCAATGCT
ATGCGTGGCGCTGTACAAAACTGGACTAAAGCAATTCCAAATGAGAAGCGTTGGACACGTAAGGTTATTG
CTAAACAGATTACCGTTGGTGGTCTAGGTCCAGCTTTCGTTGGAACCCCAGAAGAAATCGCCGATGAGCT
GGAACACTGGTCCGACCACGCTGGTTTGGACGGATTCAACTTCACTTATGCTGTCAACCCGCTTTCTTTC
GAAGAGATAGTGGAAGACTTGATTCCAGTTCTTCAGCGAAGAGGGTTGGCCCAAAAGGAATACCCAAATC
CAGAAACTGGAAGCACATTCCGTAAAAACCTTTTTGGAACAGACTTTGTACCATCTACCCACCCAGCTTA
TAACTTAAGATGGAGGGCTGGTGTGTCCAAGGAAGAATTCGAAAAGTCCCTAAACGCCACAACAAATTGG
TATTCCAGTTTCGCTAGGTCAGGTGCTCTAGGTGAATTGCATAATACATGCAGGATTCTCTATCTCCAAA
TAGTGAAATATAAATATAGGCTTCGAGTCCGTTCAGAAGGGAATAGCATCCCCTTCGCCAAAATGACCAA
GGAAAATGAAGCCAAGAGGCAGAAAACCTCTCAACCAAAAGCGAAGAAGCAATTGATTATCAATGCTTTC
ATGTCAGGCTCTTCGGGTAACCAATCGCCAGGACTGTGGTCGTACCCTGGAGACAAATCAACAGAGTATA
CTACCCTAGATTACTGGGTGGAGTTAGCTCAAAAGCTGGAAAAGGCCAAATTCCATTCTATCTTCATTGC
CGATGTTCTGGGTGGATATGACGTTTACAATGGACCTGGAAACTACAGTGCTGCTGCAAAATCTGGTGCC
CAATTTCCAATGATTGAACCAAGTGCTGCAGTTACTGCCATGGCTGCTGCTACCAAGTCAATAACGTTCG
GAGTGACTTTTTCCACTATAAGTGAGGCACCTTATCATTTTGCAAGAAGATTGGGAACTTTAGATCTGCT
GACAAACGGAAGAGTCGGCTGGAATATCGTCTCTTCGTATCTTGACAGTGCCGCCAGAAATCTTTTGAAT
GGAGAACCACTCCCTCTCCATGCAGACCGTTATAAGAGAGCCGAAGAATTCCTACAAGTTGTATATCGGT
TATTCCTTTCTTCATGGAGAGACGATGCTTATAAATTGGATAAGAAAACCAGAACCTTTGCTGACCCAAA
ACTTATTAGAACTATCGACCACGTTGGAGAGTTCTTCAATGTCCCAGGCCCCCAGTTCCTACCACCCACT
CCTCAGAGACTACCGCTGATTTTGCAGGCTGGTACTTCCAAGGTTGGTATGGATTATGCTGCAAAACATG
CAGAGGTTGTCTTTTTAGCTTCATTTGACCCAGAGTCACTCCAAGAAAAATCAAAACAGTGAGAGATAT
CGCTGAAACCAAGTACAACAGACCAAGAGATTCAATCAAATTCTTAATTTTGATAACAGTAGTCATAGCT
GATACACACGAAGATGCCGTGAAGAGATACGAAGATCTCGCCAGTTATGCTGATCTGGAAGGGGCCCAAG
CACTGTTCAGTGGTTGGACTGGAATAGATATTGGAAAGTATGGTGAAGATGAACCTCTTGAGCATGTGGA
ATCTAACGCTATTAAGAGCCATGTTAAGAACTGGACTAAGTTCAAGGACAATAAGCCTAGAGCCAGAAAA
GATATCGCTAAACAGATTGGAGTTGGAGGCTCAGGTCCCTTACTTGTTGGATCTGTACAAGAGATAGCCG
ACGAGCTTGAGAGATGGGCAGAAGTCTCTGACCTCGATGGCTTTAACTTCGCTTACGCAGATTACCCCCA
AACTTTTGATGATATCATTGAAAAACTGCTTCCAGAGTTGAACAAGAGAGGTGTGTTCTGGGATGATTAT
AAAATTCCAGGTGGAACCTTCAGAGAGAGCGTGTTTGGAAGAAAGTTCGTTGATAAGGATCATCCTGCTT
ATGATCTGAGATGGAGAAGTGACCAAACTAGGGAGGAGTTTGAAAAGAAACTGGCTGAATTGGAGAAAAA
ATAA

FIG. 1E

HP9 polynucleotide sequence (SEQ ID NO: 21)

ATGAGATTTTCTAACGTCGTTTTAACTGCAATTGCCGCTGCCGGCGTACAGGCAGATGAAGCCCTTTACACTGTG
TTCTACAATGATGTCACTGAGAACGCCCAAGAGTATCTGTCTTACATCCAGGCCAATACTGCGGCTGGTTTCACT
GACCTCTTGAGTCTGTACACTGAACTGGCCACTTACACCGACGATTCTTACACAAGTATCTTTACTGAGGAGGAT
TTCCCTGCGAGCGAACTTTCATCGTTCGTTGTTAACCTGCCATGGTATTCCTCCAGAATTGAGCCACAAGTTGCG
GCTGCTGAAACTGGTGAAAGTGAGGAGGAATCAGAGACTGGTGAAAGTGAGGAAGAATCAGAGACTGGTGAGGAG
ACAGAAACTGAGACTGGATCTGAGTCTGAATCTGAGTCTGAATCGGAGACCTCCGCTACTGGCACTGGCACTGGC
ACCTCCGCCTCTGAGAGCGCGGAGACTGAAACTTCTACCGACGCTGCTGTGTCTATCGATCACCCAAAGTCCACC
TTATTGATGGGTTTGACTGCCGCAGTTGTCAGTATCACTTTCGGAGTCTTTGCCTTGTAA

HP10 polynucleotide sequence (SEQ ID NO: 163)

ATGAGCAGCTTCAGAGTTCTAGACTTGGTAAAGCCCTTTACCCCATTTCTGCCTGAGGTTATCTCTCCAG
AGAGAAAGGTCCCCTTTCAACAGAAGTTGATGTGGACTGGAGTCACTCTTCTGATCTTCTTGGTCATGAG
TGAAATTCCCCTGTATGGTATCACTTCAAGTGACTCCTCTGACCCTTTGTTTTGGCTGCGTATGATGTTG
GCCTCTAACAGAGGAACGCTGATGGAGTTAGGTATCTCTCCTATTGTCACTTCTGGAATGGTGTTCCAAC
TGTTGCAGGGAATCCAAATCTTGGACGTGAACATGGAAAACAAAGCAGACAGAGAGTTGTTCCAAACTGC
TCAAAAAGTGTTCGCCATTTTGCTGAGTATCGGACAAGCTACTGTTTATGTTTTAACTGGAATGTATGGC
CCCCCTGGTGAACTAGGAGTTGGTGTCTGTCTTTTGTTGGTTCTTCAATTGGTGTTTGCAGGTATTGTGG
TCATTTTGTTGGATGAACTCTTACAAAAAGGTTACGGTTTAGGAAGTGGAATTTCTCTTTTCATGGCCAC
CAACATTTGTGAGCAGATTTTTTGGAAGACTTTTGCTCCTACCACCGTTAACCGTGGAAGAGGTAAGGAA
TTTGAAGGAGCTTTCATTTCTTTCTTTCACCTGATCTTGACCAAGAAGGACAAGAAGAGAGCTCTGTTGG
AATCATTTTACAGAGACAACGCTCCAAACATGTTCCAAGTTATTGCTACTCTTGTCGTCTTTTTCACCGT
TGTCTATCTTCAGGGCTTCCGTTTGGAGATTCCAGTTAAGTCTACCCGTCAAAGAGGTCCTTACGGAACT
TACCCAATCAGATTGTTCTACACATCCAACATGCCAATCATGTTACAATCCGCTTTGACCTCAAACATTT
TCATTATTTCCCAGATGTTGTATTCACACTTCCCTGACAATGCCTTTGTTAAGCTCATTGGAACTTGGGA
AGCTCAACCTGGTTCAGCACAACTGTTTGCTGCCTCGGGATTAGCCTACTACATGCAGCCTCCAATGTCC
CTGAGTCAAGCTTTATTAGACCCTATCAAGACTGTCGTCTACGTTGTGTTTGTTTTGACCACTTGTGCCA
TCTTCTCCAAGACATGGATTGAGATTTCGGGATCTTCCCCAAGAGACGTTGCTAAGCAATTCAAAGACCA
AGGATTGGTTATTGCTGGACACAGAGATGCTACTGTTTACAAGGAGTTGAAGAAGATTATACCAACAGCC
GCTGCATTTGGAGGTGCCACAATTGGTGCACTTTCCGTTGTTTCCGACCTTTTGGGTACTTTAGGTTCGG
GAACCTCCATCCTTTTGGCTGTTACAACCATCTATGGTTACTACGAGTTGGCTGTTAAGGAAGGTGGTTT
TTCAAAGGGTGGACCCTCTGGATTCGTTGATCTGTAA

FIG. 1F

K01 amino acid sequence (SEQ ID NO: 10)

MNKPNGSEQQPPSRGMKQESGGPVTSSTTPGTNTGLENSHSMGADMEPDVGATSPRHLLNGYIYDYLVKSNMQNL
ADQFAQETELLETDLTVPMDTPSGYLLEWWMVFWDLFNARLKQRGSQKAHQYIQLNMLRQQQQRTMRNTARVQKV
PLRPHTQSSPSMSQTFIPQQPQQQAQGQQHAQAQAQVQAHQQAQHHAQAQVPVQPQQHQLGGQTQQQQSINTGSP
AGPNAINSRVQHLAQQQMNHLRQQATATTQQPIPQQNIPSNQQGPTGPYPTSPSRRPRLLSNESGASAPSVMTKS
QLQGVPPSQQPHQQQGQQVGPPNQHQGQSSSFYSGMPPQGVVVPHQFNPQQYANMLARQQHVQAQQQVQLQQVQH
VQQRQQQDQQQHRLSAGSPGHPSFGVFQQPPPMSNHNQVMINQQGETFFDPHSPYAQPNGYPQPQQQQQQQQQQQ
QQQQPQQQQQQQQQKQQPPPPPRQPQRQQAMAMAPLPHSTSAAGTPHSSTTPRFSQPGPVYQQPLPASQPQHSP
PSSIQQPELVPTPGSQHQQIAQPQSQSQHQQSQQSQSSASKIVGIQEYQKELMMLEKQNKQRHDMACKKGSGHFS
NFDPIPEHTPPEPKFNVNVMLPPQNSAVVTKNTPGTSPGTQTQNTAHSTGNTSAGSTPNNVAPVRKKKEPAKKKA
KKATEPPTPTTPQTPIAARTHQNSTGGIPGNNAATKRRKREPLVDQTVSPNLNEASKSTKTGKISSQTDFTGSDN
GFLQDFGDGTGPPTGTDDMEFDFNSFLNNETGEPNSSTIHFDNVFNWGEGTEAGDL

K02 amino acid sequence (SEQ ID NO: 11)

MVVHNPNNWHWVDKNCLPWAKSYFQEVLPNTTQKNDAYEIVVTSVDLVDGDCDVTQRKGVTKCIFDLKIQVSATV
KVNTNSEVEEISYTVTLPELVHDQDEDEYEYVIEGNLDHKSQIRKLLTPLLTEKLSKFQQALIDAHTQDVQHST

K03 amino acid sequence (SEQ ID NO: 12)

MKIWLVLLLVFATVFAETDYYKVLGVAKNADEKDIKKAYRSLSKKFHPDKNPGDDEAAQKFIQVGEAYDVLGDPE
KRQRYDRFGAEGLDSRQEQFHDPFDMFQQFFGGGGQQHRGKPKGKSSLLHLEFSLQDFYNGASNDFRIEMQNICE
TCSGSGSQDGKVHQCDTCKGHGRVVQTRQFGGGMQQRFETICPKCSGTGNLITHKCKKCQGNRVVRGPRIHNVHL
GAGTSRNHVEILEGQGDQSPDWIAGDLQIMFKEKAEGNMGYRRIGNNLYRDEALTLKEALHGGWERQIAFLDKIE
NTITLSKKKGEVVVDGQVDTIKGRGMPLHDHYDEHGDLFIKYHIIYPQQIRDEL

FIG. 1G

KO1 polynucleotide sequence (SEQ ID NO: 22)

ATGAACAAGCCAAACGGGTCTGAACAACAACCACCGTCACGCGGAATGAAGCAAGAGTCAGGAGGCCCAGTTACT
TCATCTACGACGCCGGGTACCAATACTGGCCTAGAAAACTCTCATTCCATGGGGCGGATATGGAGCCTGATGTT
GGTGCTACCTCTCCTCGCCATCTTCTTAATGGGTACATTTACGATTATTTAGTCAAATCTAACATGCAAAATTTG
GCTGATCAATTTGCCCAAGAGACGGAGCTCTTAGAAACAGACTTGACAGTACCAATGGATACGCCTTCAGGCTAT
CTTCTAGAATGGTGGATGGTATTCTGGGACCTTTTCAATGCCCGCCTAAAGCAACGGGGTTCACAGAAGGCCCAC
CAGTATATTCAGTTGAACATGCTACGACAACAGCAACAGAGGACCATGCGAAATACAGCCCGTGTTCAAAAGTC
CCGTTGAGGCCACACACCCAATCATCTCCTTCAATGTCACAGACTTTTATTCCACAGCAGCCTCAACAGCAAGCA
CAGGGACAACAGCACGCCCAGGCTCAAGCCCAAGTGCAAGCACATCAGCAAGCCCAACACCACGCGCAGGCACAA
GTGCCAGTGCAACCGCAACAGCACCAGCTAGGAGGCCAAACTCAACAGCAGCAATCCATTAACACTGGGTCTCCT
GCGGGTCCAAATGCTATCAACTCGCGTGTTCAACACTTAGCACAACAACAGATGAATCACCTTCGCCAGCAGGCG
ACTGCCACTACGCAACAACCTATCCCGCAACAGAATATCCCATCAAACCAACAGGGTCCTACAGGCCCTTATCCT
ACTTCCCCTTCAAGAAGACCGAGATTACTGTCTAACGAATCGGGTGCAAGTGCACCCTCTGTAATGACAAAGTCA
CAGCTCCAAGGAGTCCCTCCCTCACAACAACCACACCAGCAGCAAGGTCAGCAGGTAGGCCCCCCTAATCAACAT
CAAGGTCAATCTTCTTCCTTTTATTCGGGCATGCCTCCTCAAGGGGTCGTGGTTCCTCATCAGTTCAATCCTCAG
CAGTATGCCAATATGCTAGCAAGACAACAGCATGTACAAGCTCAACAACAGGTTCAGTTACAACAGGTCCAACAT
GTACAACAGAGACAACAGCAAGACCAACAACAACACCGCCTGTCCGCCGGTTCACCGGGGCACCCTTCATTTGGC
GTTTTTCAACAACCTCCTCCGATGTCAAACCATAATCAGGTCATGATCAATCAGCAGGGAGAAACTTTTTTTGAT
CCACATTCTCCATATGCTCAACCTAACGGGTACCCCAGCCACAGCAACAACAACAACAACAGCAACAACAACAA
CAACAGCAGCAACCGCAACAGCAGCAGCAGCAGCAGCAGCAACAGAAGCAGCAACCACCACCACCACCACGACAG
CCTCAGCGCCAACAAGCGATGGCCATGGCTCCTCTGCCTCACTCTACTTCTGCCGCCGGTACTCCTCACTCGTCC
ACCACACCTAGATTCTCGCAACCTGGTCCTGTTTATCAGCAGCCTTTACCTGCATCTCAACCGCAACATTCTCCG
CCTTCTTCTATTCAGCAGCCGGAGCTAGTTCCAACTCCAGGGTCACAACATCAGCAAATAGCACAACCACAATCA
CAGAGCCAACACCAGCAATCGCAACAGTCTCAATCAAGTGCTTCTAAAATTGTAGGTATACAGGAGTATCAGAAA
GAGCTAATGATGCTTGAGAAACAGAACAAACAGCGTCATGACATGGCATGTAAGAAGGGAAGCGGGCATTTTTCT
AACTTTGATCCAATTCCAGAGCACACACCGCCCGAACCAAAATTTAATGTGAATGTAATGCTCCCTCCCCAGAAC
TCTGCAGTGGTCACGAAGAATACTCCCGGAACTTCACCTGGTACACAAACTCAAAACACTGCACATAGTACTGGT
AACACTTCTGCGGGGTCTACACCAAATAATGTCGCACCTGTACGAAAGAAAAAGGAGCCAGCTAAAAAGAAGGCA
AAGAAAGCTACTGAGCCCCCGACTCCCACTACTCCACAGACTCCAATTGCAGCTAGGACACATCAAAACTCTACA
GGCGGCATTCCTGGTAATAATGCTGCTACTAAGCGACGAAAACGGGAGCCGCTGGTTGATCAAACTGTTTCACCT
AACCTTAACGAAGCTTCCAAGTCAACAAAGACCGGAAAAATTTCATCTCAAACTGACTTTACAGGTTCTGACAAT
GGATTCTTACAGGATTTTGGCGATGGAACTGGTCCTCCCACTGGAACCGATGATATGGAATTTGATTTTAACAGT
TTTCTTAATAACGAAACTGGCGAACCTAATAGTTCAACCATTCATTTTGACAATGTATTCAATTGGGGAGAAGGT
ACCGAAGCCGGAGATTTATAG

KO2 polynucleotide sequence (SEQ ID NO: 23)

ATGGTGGTGCACAACCCTAATAACTGGCACTGGGTCGACAAGAACTGCCTTCCTTGGGCCAAAAGCTACTTTCAG
GAAGTCCTTCCAAACACCACTCAGAAGAATGACGCCTATGAAATAGTGGTAACATCTGTGGACCTTGTAGATGGA
GACTGCGATGTCACTCAACGTAAAGGTGTTACCAAATGTATTTTTGATCTGAAGATACAGGTATCTGCAACCGTC
AAAGTCAACACGAACAGTGAAGTAGAGGAGATCAGTTATACAGTGACATTACCTGAACTGGTGCACGACCAGGAC
GAGGATGAATATGAATACGTAATAGAGGGAAATTTGGATCACAAGTCTCAAATTAGAAAGCTACTCACTCCTCTG
TTGACCGAGAAGTTATCAAAGTTTCAACAAGCTTTGATAGACGCTCATACTCAGGATGTTCAGCATAGTACCTAG

KO3 polynucleotide sequence (SEQ ID NO: 24)

ATGAAGATATGGCTGGTACTTCTTTTAGTTTTTGCCACGGTGTTTGCCGAGACAGATTATTATAAAGTTCTTGGA
GTAGCTAAAAATGCGGATGAAAAAGATATCAAGAAGGCCTACAGATCGTTGAGTAAGAAGTTTCATCCAGATAAG
AACCCGGGTGATGATGAAGCCGCTCAAAAGTTCATTCAAGTTGGAGAAGCTTATGATGTGCTTGGTGATCCCGAG
AAGCGTCAAAGGTATGACAGATTTGGAGCAGAAGGACTGGACTCAAGACAGGAACAATTCCATGATCCATTTGAC
ATGTTTCAACAGTTCTTCGGAGGAGGTGGACAGCAACACAGAGGCAAACCAAAGGGTAAGAGTTCCTTGTTACAT
TTAGAATTCAGTCTACAAGACTTTTACAATGGTGCTAGTAACGACTTTAGAATCGAAATGCAGAATATCTGTGAA
ACTTGTTCTGGATCAGGTTCACAAGACGGGAAAGTTCATCAATGTGACACTTGCAAAGGGCACGGGCGTGTTGTT
CAAACGAGACAGTTTGGTGGTGGCATGCAACAGAGGTTTGAAACAATTTGCCCAAAATGTTCAGGAACAGGAAAT
CTGATCACTCACAAGTGTAAGAAATGCCAAGGAAACCGTGTAGTTAGAGGACCCAGAATTCACAATGTGCATTTG
GGGGCGGGAACTAGTAGGAACCATGTTGAGATCCTGGAAGGTCAGGGAGACCAGTCTCCAGACTGGATTGCAGGT
GATCTACAAATCATGTTCAAGGAGAAAGCCGAAGGCAACATGGGTATAGAAGAATAGGAAACAACCTGTACAGA
GACGAAGCATTAACGCTGAAAGAGGCATTGCATGGTGGCTGGGAGAGACAAATTGCGTTTTTGGATAAAATAGAG
AACACGATTACTCTTTCCAAGAAGAAAGGAGAGGTGGTAGTTGACGGCCAAGTAGACACCATCAAGGGTAGAGGG
ATGCCATTACATGACCACTATGACGAACATGGTGATCTCTTTATCAAGTACCATATCATTTACCCGCAACAAATT
AGAGACGAATTGTGA

FIG. 1H

SDZ-Fab HC amino acid sequence (SEQ ID NO: 25)

*MRFPSIFTAVLFAASSALAAPVNTTTEDETAQIPAEAVIGYSDLEGDFDVAVLPFSNSTNNGLLFINTTIASIAA*
*KEEGVSLEKRE*VQLVQSGGGLVQPGGSLRLSCAASGFTFSHYWMSWVRQAPGKGLEWVANIEQDGSEKYYVDSVK
GRFTISRDNAKNSLYLQMNSLRAEDTAVYFCARDLEGLHGDGYFDLWGRGTLVTVSSASTKGPSVFPLAPCSRST
SESTAALGCLVKDYFPEPVTVSWNSGALTSGVHTFPAVLQSSGLYSLSSVVTVPSSSLGTKTYTCNVDHKPSNTK
VDKRVESKYGPP

SDZ-Fab LC amino acid sequence (SEQ ID NO: 26)

*MRFPSIFTAVLFAASSALAAPVNTTTEDETAQIPAEAVIGYSDLEGDFDVAVLPFSNSTNNGLLFINTTIASIAA*
*KEEGVSLEKR*AIQLTQSPSSLSASVGDRVILTCRASQGVSSALAWYQQKPGKAPKLLIYDASSLESGVPSRFSGS
GSGPDFTLTISSLQPEDFATYFCQQFNSYPLTFGGGTKLEIKRTVAAPSVFIFPPSDEQLKSGTASVVCLLNNFY
PREAKVQWKVDNALQSGNSQESVTEQDSKDSTYSLSSTLTLSKADYEKHKVYACEVTHQGLSSPVTKSFNRGEC

SDZ-Fab HC polynucleotide sequence (SEQ ID NO: 27)

*ATGAGATTCCCATCTATTTTCACCGCTGTCTTGTTCGCTGCCTCCTCTGCATTGGCTGCCCCTGTTAACACTACC*
*ACTGAAGACGAGACTGCTCAAATTCCAGCTGAAGCAGTTATCGGTTACTCTGACCTTGAGGGTGATTTCGACGTC*
*GCTGTTTTGCCTTTCTCTAACTCCACTAACAACGGTTTGTTGTTCATTAACACCACTATCGCTTCCATTGCTGCT*
*AAGGAAGAGGGTGTCTCTCTCGAGAAGAGA*GAGGTCCAATTGGTCCAATCTGGTGGAGGATTGGTTCAACCAGGT
GGATCTCTGAGATTGTCTTGTGCTGCTTCTGGTTTCACCTTCTCTCACTACTGGATGTCATGGGTTAGACAAGCT
CCTGGTAAGGGTTTGGAATGGGTTGCTAACATCGAGCAAGATGGATCAGAGAAGTACTACGTTGACTCTGTTAAG
GGAAGATTCACTATTTCCCGTGATAACGCCAAGAACTCCTTGTACCTGCAAATGAACTCCCTTAGAGCTGAGGAT
ACTGCTGTCTACTTCTGTGCTAGAGACTTGGAAGGTTTGCATGGTGATGGTTACTTCGACTTATGGGGTAGAGGT
ACTCTTGTCACCGTTTCATCTGCCTCTACCAAAGGACCTTCTGTGTTCCCATTAGCTCCATGTTCCAGATCCACC
TCCGAATCTACTGCAGCTTTGGGTTGTTTGGTGAAGGACTACTTTCCTGAACCAGTGACTGTCTCTTGGAACTCT
GGTGCTTTGACTTCTGGTGTTCACACCTTTCCTGCAGTTTTGCAGTCATCTGGTCTGTACTCTCTGTCCTCAGTT
GTCACTGTTCCTTCCTCATCTCTTGGTACCAAGACCTACACTTGCAACGTTGACCATAAGCCATCCAATACCAAG
GTTGACAAGAGAGTTGAGTCCAAGTATGGTCCACCTtaa

SDZ-Fab LC polynucleotide sequence (SEQ ID NO: 28)

*ATGAGATTCCCATCTATTTTCACCGCTGTCTTGTTCGCTGCCTCCTCTGCATTGGCTGCCCCTGTTAACACTACC*
*ACTGAAGACGAGACTGCTCAAATTCCAGCTGAAGCAGTTATCGGTTACTCTGACCTTGAGGGTGATTTCGACGTC*
*GCTGTTTTGCCTTTCTCTAACTCCACTAACAACGGTTTGTTGTTCATTAACACCACTATCGCTTCCATTGCTGCT*
*AAGGAAGAGGGTGTCTCTCTCGAGAAGAGA*GCTATCCAGTTGACTCAATCACCATCCTCTTTGTCTGCTTCTGTT
GGTGATAGAGTCATCCTGACTTGTCGTGCATCTCAAGGTGTTTCCTCAGCTTTAGCTTGGTACCAACAAAAGCCA
GGTAAAGCTCCAAAGTTGCTGATCTACGACGCTTCATCCCTTGAATCTGGTGTTCCTTCACGTTTCTCTGGATCT
GGATCAGGTCCTGATTTCACTCTGACTATCTCATCCCTTCAACCAGAAGACTTTGCTACCTACTTCTGTCAACAG
TTCAACTCTTACCCTTTGACCTTTGGAGGTGGAACTAAGTTGGAGATCAAGAGAACTGTTGCTGCACCATCAGTG
TTCATCTTTCCTCCATCTGATGAGCAACTGAAGTCTGGTACTGCATCTGTTGTCTGCTTACTGAACAACTTCTAC
CCAAGAGAAGCTAAGGTCCAATGGAAGGTTGACAATGCCTTGCAATCTGGTAACTCTCAAGAGTCTGTTACTGAG
CAAGACTCTAAGGACTCTACTTACTCCCTTTCTTCCACCTTGACTTTGTCTAAGGCTGATTACGAGAAGCACAAG
GTTTACGCTTGTGAGGTTACTCACCAAGGTTTGTCTTCTCCTGTTACCAAGTCTTTCAACAGAGGTGAATGCTAA

FIG. 2A

HyHEL-Fab HC amino acid sequence (SEQ ID NO: 29)

*MRFPSIFTAVLFAASSALAAPVNTTTEDETAQIPAEAVIGYSDLEGDFDVAVLPFSNSTNNGLLFINTTIASIAA
KEEGVSLEKR*DVQLQESGPSLVKPSQTLSLTCSVTGDSITSDYWSWIRKFPGNRLEYMGYVSYSGSTYYNPSLKS
RISITRDTSKNQYYLDLNSVTTEDTATYYCANWDGDYWGQGTLVTVSSASTKGPSVFPLAPSSKSTSGGTAALGC
LVKDYFPEPVTVSWNSGALTSGVHTFPAVLQSSGLYSLSSVVTVPSSSLGTQTYICNVNHKPSNTKVDKRVEPKS
CDK

HyHEL-Fab LC amino acid sequence (SEQ ID NO: 30)

*MRFPSIFTAVLFAASSALAAPVNTTTEDETAQIPAEAVIGYSDLEGDFDVAVLPFSNSTNNGLLFINTTIASIAA
KEEGVSLEKR*DIVLTQSPATLSVTPGNSVSLSCRASQSIGNNLHWYQQKSHESPRLLIKYASQSISGIPSRFSGS
GSGTDFTLSINSVETEDFGMYFCQQSNSWPYTFGGGTKLEIKRTVAAPSVFIFPPSDEQLKSGTASVVCLLNNFY
PREAKVQWKVDNALQSGNSQESVTEQDSKDSTYSLSSTLTLSKADYEKHKVYACEVTHQGLSSPVTKSFNRGEC

HyHEL-Fab HC polynucleotide sequence (SEQ ID NO: 31)

*ATGAGATTCCCATCTATTTTCACCGCTGTCTTGTTCGCTGCCTCCTCTGCATTGGCTGCCCCTGTTAACACTACC
ACTGAAGACGAGACTGCTCAAATTCCAGCTGAAGCAGTTATCGGTTACTCTGACCTTGAGGGTGATTTCGACGTC
GCTGTTTTGCCTTTCTCTAACTCCACTAACAACGGTTTGTTGTTCATTAACACCACTATCGCTTCCATTGCTGCT
AAGGAAGAGGGTGTCTCTCTCGAGAAGAGA*GACGTTCAATTGCAAGAATCTGGTCCATCCTTGGTTAAGCCATCC
CAGACTTTGTCCTTGACTTGTTCCGTTACTGGTGACTCCATCACTTCTGACTACTGGTCCTGGATCAGAAAGTTC
CCAGGTAACAGATTGGAGTACATGGGTTACGTTTCTTACTCCGGTTCCACTTACTACAACCCATCCTTGAAGTCC
AGAATCTCCATCACTAGAGACACTTCCAAGAACCAGTACTACTTGGACTTGAACTCCGTTACTACTGAGGACACT
GCTACTTACTACTGTGCTAACTGGGACGGTGACTATTGGGGTCAAGGTACTTTGGTTACTGTTTCCTCCGCTTCC
ACTAAGGGTCCATCTGTTTTTCCATTGGCTCCATCCTCCAAGTCTACTTCAGGTGGTACTGCTGCTTTGGGTTGT
TTGGTTAAGGACTACTTCCCAGAGCCAGTTACTGTTTCTTGGAACTCCGGTGCTTTGACTTCCGGTGTTCACACT
TTCCCAGCTGTCTTGCAATCCTCCGGTCTGTACTCCTTGTCCTCCGTTGTTACTGTTCCTTCTTCCTCCTTGGGT
ACTCAAACTTACATCTGTAACGTTAACCACAAGCCATCCAACACTAAGGTTGACAAGAGAGTTGAGCCAAAGTCC
TGTGACAAGTAATAG

HyHEL-Fab LC polynucleotide sequence (SEQ ID NO: 32)

*ATGAGATTCCCATCTATTTTCACCGCTGTCTTGTTCGCTGCCTCCTCTGCATTGGCTGCCCCTGTTAACACTACC
ACTGAAGACGAGACTGCTCAAATTCCAGCTGAAGCAGTTATCGGTTACTCTGACCTTGAGGGTGATTTCGACGTC
GCTGTTTTGCCTTTCTCTAACTCCACTAACAACGGTTTGTTGTTCATTAACACCACTATCGCTTCCATTGCTGCT
AAGGAAGAGGGTGTCTCTCTCGAGAAGAGA*GACATCGTTTTGACTCAATCCCCAGCTACTTTGTCCGTTACTCCA
GGTAACTCCGTTTCCTTGTCCTGTAGAGCTTCCCAGTCCATCGGTAACAACTTGCACTGGTATCAGCAGAAGTCT
CACGAGTCCCCAAGACTGTTGATCAAGTACGCTTCCCAATCCATCTCCGGTATCCCATCTAGATTCTCTGGTTCT
GGTTCCGGTACTGACTTCACTTTGTCCATCAACTCCGTTGAGACTGAGGACTTCGGTATGTACTTCTGTCAGCAA
TCCAACTCCTGGCCATACACTTTTGGTGGTGGTACTAAGTTGGAGATCAAGAGAACTGTTGCTGCTCCATCCGTT
TTCATCTTCCCACCATCTGACGAGCAGTTGAAGTCTGGTACTGCTTCCGTTGTTTGTTTGTTGAACAACTTCTAC
CCAAGAGAAGCTAAGGTTCAGTGGAAGGTTGACAACGCCTTGCAATCCGGTAACTCCCAAGAGTCCGTTACTGAA
CAAGACTCCAAGGACTCTACTTACTCCTTGTCCTCCACTTTGACTTTGTCCAAGGCTGACTACGAGAAGCACAAG
GTTTACGCTTGTGAGGTTACTCACCAGGGTTTGTCCTCCCAGTTACTAAGTCCTTCAACAGAGGTGAGTGTTAA
TAG (Underlined and italics: S. cerevisiae-alfa mating factor prepro leader)

FIG. 2B

```
                        SEQUENCE LISTING

<160> NUMBER OF SEQ ID NOS: 163

<210> SEQ ID NO 1
<211> LENGTH: 95
<212> TYPE: PRT
<213> ORGANISM: Pichia pastoris

<400> SEQUENCE: 1

Met Leu Asn Lys Leu Phe Ile Ala Ile Leu Ile Val Ile Thr Ala Val
1               5                   10                  15

Ile Gly Glu Thr Thr Thr Ser Ser Thr Thr Ala Ser Leu Ser Glu Ser
            20                  25                  30

Pro Thr Leu Val Trp Val Thr Gly Thr Asp Ala Ser Gly Arg Leu Ala
        35                  40                  45

Thr Thr Gln Ser Ala Tyr Thr Gln Gln Phe Ser Gln Leu Tyr Ser Ser
    50                  55                  60

Ile Ala Ser Pro Ser Ser Gly Ser Ile Gly Leu Gly Thr Ile Gln Gly
65                  70                  75                  80

Thr Val Gly Ile Val Arg Thr Tyr Glu Thr Ile Thr Leu Ala Ser
                85                  90                  95

<210> SEQ ID NO 2
<211> LENGTH: 86
<212> TYPE: PRT
<213> ORGANISM: Pichia pastoris

<400> SEQUENCE: 2

Met Ser Thr Ala Ile Pro Gly Gly Gln Arg Thr Leu Ala Lys Arg Arg
1               5                   10                  15

Ala Ala Asn Leu Asp Lys Lys Gln Asp Glu Pro Thr Ser Ala Arg Ser
            20                  25                  30

Ala Gly Ala Gly Gly Ser Ser Ser Thr Met Leu Lys Leu Tyr Thr Asp
        35                  40                  45

Glu Ala Gln Gly Leu Lys Val Asp Pro Leu Ile Val Leu Val Leu Ala
    50                  55                  60

Val Gly Phe Ile Phe Ser Val Ile Gly Leu His Val Val Ala Lys Leu
65                  70                  75                  80
```

Thr Gly Lys Leu Ile Asn
            85

<210> SEQ ID NO 3
<211> LENGTH: 361
<212> TYPE: PRT
<213> ORGANISM: Pichia pastoris

<400> SEQUENCE: 3

Met Thr Pro Arg Ser His Ile Phe Phe Asp Ile Ser Ile Asn Asn Gln
1               5                   10                  15

Pro Ala Gly Arg Ile Ile Phe Glu Leu Phe Asn Asp Ile Val Pro Lys
            20                  25                  30

Thr Ala Glu Asn Phe Arg Ala Leu Ser Thr Gly Glu Lys Gly Ile Gly
        35                  40                  45

Lys Ser Gly Lys Pro Leu His Tyr Lys Gly Ser Thr Phe His Arg Ile
    50                  55                  60

Ile Lys Asp Phe Met Val Gln Gly Gly Asp Phe Thr Asn Gly Asn Gly
65                  70                  75                  80

Thr Gly Gly Glu Ser Ile Tyr Gly Glu Lys Phe Glu Asp Glu Asn Phe
                85                  90                  95

Gln Leu Thr His Asp Lys Pro Phe Leu Leu Ser Met Ala Asn Ala Gly
            100                 105                 110

Pro Gly Thr Asn Gly Ser Gln Phe Phe Ile Thr Thr Val Pro Thr Pro
        115                 120                 125

His Leu Asp Asn Lys His Val Val Phe Gly Lys Val Ile Ala Gly Lys
    130                 135                 140

Ala Thr Val Arg Lys Ile Glu Arg Asn Ser Glu Gly Glu Ala Pro Ile
145                 150                 155                 160

Glu Pro Val Val Ile Glu Asp Cys Gly Glu Leu Pro Glu Asp Ala Asp
                165                 170                 175

Leu Thr Ile Ser Asp Glu Thr Gly Asp Lys Tyr Glu Glu Val Leu Lys
            180                 185                 190

Asp Asn Glu Asn Ile Asp Ile Asp Asp Phe Glu Gln Val Tyr Gln Ala
        195                 200                 205

Ile Thr Glu Ile Lys Glu Leu Gly Thr Lys Tyr Phe Lys Asn Gly Asp
    210                 215                 220

Thr Lys Ile Ala Phe Glu Lys Tyr Gln Lys Ala Ala Asn Tyr Leu Leu
225                 230                 235                 240

Glu Tyr Ile Pro Ser Asp Leu Ser Glu Glu Gln Ser Ser Lys Leu Glu
                245                 250                 255

Leu Leu Lys Thr Ser Val Phe Ser Asn Val Ala Leu Ala Gly Leu Lys
            260                 265                 270

Val Ser Lys Phe Lys Asp Thr Ile Lys Tyr Ala Thr Leu Val Ile Glu
        275                 280                 285

Asp Glu Ser Ala Asp Ala Lys Ala Lys Ser Lys Gly Tyr Tyr Arg Arg
    290                 295                 300

Gly Ser Ala Tyr Ser Ser Leu Lys Asp Glu Asp Ser Ala Ile Ser Asp
305                 310                 315                 320

Phe Gln Lys Ala Leu Glu Leu Ser Pro Gly Asp Pro Ala Ile Ser Gln
                325                 330                 335

Ser Leu Gln Arg Thr Thr Lys Ala Arg Lys Asp Arg Leu Ala Lys Glu
            340                 345                 350

Lys Ala Ala Leu Ser Lys Phe Phe Glu
        355                 360

-continued

```
<210> SEQ ID NO 4
<211> LENGTH: 274
<212> TYPE: PRT
<213> ORGANISM: Pichia pastoris

<400> SEQUENCE: 4

Met Ser Ser Asp Ala Val Glu Gln Leu Glu Asn Phe Gln Leu Ile Lys
1               5                   10                  15

Phe Asp Arg Phe Asp Pro Ser Thr Gln Ser Thr Ile Arg Ile Ala Arg
            20                  25                  30

Ser Pro Lys Pro Ile Pro Val Lys Val Ile Val Gly Asp Gly Gly
        35                  40                  45

Cys Gly Lys Thr Cys Leu Leu Asn Val Phe Ala Thr Gly Thr Phe Pro
    50                  55                  60

Glu Ala Tyr Val Pro Thr Ile Ile Glu Asn Val Val Ile Thr Leu Val
65                  70                  75                  80

Thr Pro Thr Gly Gln Ile Ala Ala Val Thr Leu Trp Asp Thr Ala Gly
            85                  90                  95

Gln Glu Glu Tyr Asp Arg Leu Arg Pro Leu Ser Tyr Ser Asp Val Asp
            100                 105                 110

Val Val Leu Leu Cys Tyr Ser Ile Asp Asn Leu Ser Thr Phe His Asn
        115                 120                 125

Val Ala Asp Lys Trp Tyr Pro Glu Val Ala His Phe Cys Pro Asn Thr
    130                 135                 140

Pro Ile Ile Leu Val Gly Thr Lys Ser Asp Met Arg Arg His Gln Lys
145                 150                 155                 160

Ser Gln Pro His Phe Val Ser Pro Gln Asp Ser Ser Gln Leu Ala Arg
            165                 170                 175

Gln Met Gly Ala Val Met Asn Ile Glu Cys Ser Ala Lys Glu Val Ser
            180                 185                 190

Asn Val Asn Ile Val Phe Asp Ala Ala Val Ser Tyr Cys Leu Ser Asn
        195                 200                 205

Ser Arg Pro Lys Thr Arg Gly Asp Asn Asp Asn Arg Ser Asn Arg
    210                 215                 220

Arg Leu Ser Arg Ala Lys Arg Ala Ser Met Phe Ile Arg Gly Lys Asp
225                 230                 235                 240

Val Ser Ser Thr Ser Gly Asn Ser Arg Glu Glu Leu Val Glu Tyr Asp
            245                 250                 255

Gln Asp Gly Leu Ala Ile Ile Pro Asp Arg Lys Lys Lys Cys Ser
            260                 265                 270

Ile Ile

<210> SEQ ID NO 5
<211> LENGTH: 127
<212> TYPE: PRT
<213> ORGANISM: Pichia pastoris

<400> SEQUENCE: 5

Met Thr Asn Trp Lys Ala Ile Leu Thr Pro Ala Gln Tyr Gln Val Leu
1               5                   10                  15

Arg Leu Gly Gly Thr Glu Arg Pro Tyr Thr Gly Gln Tyr Val Asn Phe
            20                  25                  30

Lys Lys Asn Gly Thr Tyr Leu Cys Ser Gly Cys Gln Thr Pro Leu Tyr
        35                  40                  45
```

-continued

```
Lys Ser Gly Thr Lys Phe Asp Ser Ser Cys Gly Trp Pro Ala Phe Tyr
     50                  55                  60

Glu Ala Leu Pro Gly Ala Val Lys Arg Ile Glu Asp Asn Ser Leu Gly
 65                  70                  75                  80

Met Arg Arg Ile Glu Ile Arg Cys Ser Lys Cys Asp Gly His Leu Gly
                 85                  90                  95

His Val Phe Glu Gly Glu Gly Phe Asp Thr Pro Thr Asp Ser Arg His
            100                 105                 110

Cys Val Asn Ser Ile Ser Leu Lys Phe Gln Gly Glu Glu Asn
        115                 120                 125

<210> SEQ ID NO 6
<211> LENGTH: 1027
<212> TYPE: PRT
<213> ORGANISM: Pichia pastoris

<400> SEQUENCE: 6

Met Thr Thr Asn Gly Gln Lys Arg Gln Lys Thr Arg Lys Pro Leu Leu
  1               5                  10                  15

Ile Asn Ala Phe Val Met Gly Cys Ala Gly Leu Gln Asn Pro Gly Leu
                 20                  25                  30

Trp Lys His Pro Lys Asp Ser His Arg Phe Asn Gln Ile Asp His
             35                  40                  45

Trp Thr Tyr Leu Ala Lys Leu Ala Glu Lys Gly Lys Phe Asn Ala Leu
     50                  55                  60

Phe Ile Ala Asp Val Leu Gly Gly Tyr Asp Val Tyr Lys Gly Pro Glu
 65                  70                  75                  80

Asn Leu Ala Thr Pro Ala Val Ala Gly Ala Gln Trp Pro Val Thr Glu
                 85                  90                  95

Pro Ser Ala Val Val Ser Ala Met Ala Ala Val Thr Thr Asn Leu Ala
            100                 105                 110

Phe Gly Val Thr Phe Ser Thr Ile Ser Glu Ala Pro Tyr His Phe Ala
            115                 120                 125

Arg Arg Leu Ser Thr Leu Asp His Leu Thr Lys Gly Arg Ile Gly Trp
        130                 135                 140

Asn Val Val Ser Ser Tyr Leu Glu Ser Ala Ala Arg Asn Leu Leu Asn
145                 150                 155                 160

Gly Glu Lys Leu Asp Glu His Asp Gln Arg Tyr Leu Lys Ala Glu Glu
                165                 170                 175

Tyr Ile Gln Ile Val Tyr Glu Leu Leu Leu Ser Ser Trp Arg Asp Asp
            180                 185                 190

Ala Val Val Leu Asp Lys Lys Ala Gly Val Tyr Thr Asp Pro Thr Arg
        195                 200                 205

Phe Arg Lys Ile Asn Phe Glu Gly Lys Phe Phe Lys Val Pro Gly Pro
    210                 215                 220

His Ile Val Asp Pro Thr Pro Gln Arg Leu Pro Val Ile Leu Gln Ala
225                 230                 235                 240

Gly Thr Ser Lys Val Gly Lys Glu Phe Ala Ala Lys His Ala Glu Ile
                245                 250                 255

Val Phe Val Ile Ser Phe Ser Pro Asp Asp Leu Lys Pro Lys Ile Ala
            260                 265                 270

Glu Val Arg Gln Leu Ala Lys Glu Lys Phe Gly Arg Asn His Asp Asp
        275                 280                 285

Ile Lys Phe Val Ala Leu Ala Thr Pro Val Ile Gly Ala Thr His Glu
    290                 295                 300
```

```
Leu Ala Glu Glu Lys Tyr Gln Glu Leu Leu Ser Tyr Gly Asp Ile Glu
305                 310                 315                 320

Gly Ala Gln Ala Leu Phe Gly Gly Trp Thr Gly Ile Asp Leu Ser Gln
            325                 330                 335

Tyr Gly Glu Asp Glu Glu Leu Gly Asn Val Ser Ser Asn Ala Met Arg
            340                 345                 350

Gly Ala Val Gln Asn Trp Thr Lys Ala Ile Pro Asn Glu Lys Arg Trp
            355                 360                 365

Thr Arg Lys Val Ile Ala Lys Gln Ile Thr Val Gly Gly Leu Gly Pro
370                 375                 380

Ala Phe Val Gly Thr Pro Glu Glu Ile Ala Asp Glu Leu Glu His Trp
385                 390                 395                 400

Ser Asp His Ala Gly Leu Asp Gly Phe Asn Phe Thr Tyr Ala Val Asn
                405                 410                 415

Pro Leu Ser Phe Glu Glu Ile Val Glu Asp Leu Ile Pro Val Leu Gln
                420                 425                 430

Arg Arg Gly Leu Ala Gln Lys Glu Tyr Pro Asn Pro Glu Thr Gly Ser
                435                 440                 445

Thr Phe Arg Lys Asn Leu Phe Gly Thr Asp Phe Val Pro Ser Thr His
450                 455                 460

Pro Ala Tyr Asn Leu Arg Trp Arg Ala Gly Val Ser Lys Glu Glu Phe
465                 470                 475                 480

Glu Lys Ser Leu Asn Ala Thr Thr Asn Trp Tyr Ser Ser Phe Ala Arg
                485                 490                 495

Ser Gly Ala Leu Gly Glu Leu His Asn Thr Cys Arg Ile Leu Tyr Leu
                500                 505                 510

Gln Ile Val Lys Tyr Lys Tyr Arg Leu Arg Val Arg Ser Gly Asn
                515                 520                 525

Ser Ile Pro Phe Ala Lys Met Thr Lys Glu Asn Glu Ala Lys Arg Gln
530                 535                 540

Lys Thr Ser Gln Pro Lys Ala Lys Lys Gln Leu Ile Ile Asn Ala Phe
545                 550                 555                 560

Met Ser Gly Ser Ser Gly Asn Gln Ser Pro Gly Leu Trp Ser Tyr Pro
                565                 570                 575

Gly Asp Lys Ser Thr Glu Tyr Thr Thr Leu Asp Tyr Trp Val Glu Leu
                580                 585                 590

Ala Gln Lys Leu Glu Lys Ala Lys Phe His Ser Ile Phe Ile Ala Asp
            595                 600                 605

Val Leu Gly Gly Tyr Asp Val Tyr Asn Gly Pro Gly Asn Tyr Ser Ala
            610                 615                 620

Ala Ala Lys Ser Gly Ala Gln Phe Pro Met Ile Glu Pro Ser Ala Ala
625                 630                 635                 640

Val Thr Ala Met Ala Ala Ala Thr Lys Ser Ile Thr Phe Gly Val Thr
                645                 650                 655

Phe Ser Thr Ile Ser Glu Ala Pro Tyr His Phe Ala Arg Arg Leu Gly
                660                 665                 670

Thr Leu Asp Leu Leu Thr Asn Gly Arg Val Gly Trp Asn Ile Val Ser
                675                 680                 685

Ser Tyr Leu Asp Ser Ala Ala Arg Asn Leu Asn Gly Glu Pro Leu
                690                 695                 700

Pro Leu His Ala Asp Arg Tyr Lys Arg Ala Glu Glu Phe Leu Gln Val
705                 710                 715                 720
```

-continued

Val Tyr Arg Leu Phe Leu Ser Ser Trp Arg Asp Ala Tyr Lys Leu
              725                 730                 735

Asp Lys Lys Thr Arg Thr Phe Ala Asp Pro Lys Leu Ile Arg Thr Ile
        740                 745                 750

Asp His Val Gly Glu Phe Phe Asn Val Pro Gly Pro Gln Phe Leu Pro
        755                 760                 765

Pro Thr Pro Gln Arg Leu Pro Leu Ile Leu Gln Ala Gly Thr Ser Lys
    770                 775                 780

Val Gly Met Asp Tyr Ala Ala Lys His Ala Glu Val Val Phe Leu Ala
785                 790                 795                 800

Ser Phe Asp Pro Glu Ser Leu Gln Glu Lys Ile Lys Thr Val Arg Asp
                805                 810                 815

Ile Ala Glu Thr Lys Tyr Asn Arg Pro Arg Asp Ser Ile Lys Phe Leu
            820                 825                 830

Ile Leu Ile Thr Val Val Ile Ala Asp Thr His Glu Asp Ala Val Lys
        835                 840                 845

Arg Tyr Glu Asp Leu Ala Ser Tyr Ala Asp Leu Glu Gly Ala Gln Ala
    850                 855                 860

Leu Phe Ser Gly Trp Thr Gly Ile Asp Ile Gly Lys Tyr Gly Glu Asp
865                 870                 875                 880

Glu Pro Leu Glu His Val Glu Ser Asn Ala Ile Lys Ser His Val Lys
                885                 890                 895

Asn Trp Thr Lys Phe Lys Asp Asn Lys Pro Arg Ala Arg Lys Asp Ile
            900                 905                 910

Ala Lys Gln Ile Gly Val Gly Gly Ser Gly Pro Leu Leu Val Gly Ser
        915                 920                 925

Val Gln Glu Ile Ala Asp Glu Leu Glu Arg Trp Ala Glu Val Ser Asp
    930                 935                 940

Leu Asp Gly Phe Asn Phe Ala Tyr Ala Asp Tyr Pro Gln Thr Phe Asp
945                 950                 955                 960

Asp Ile Ile Glu Lys Leu Leu Pro Glu Leu Asn Lys Arg Gly Val Phe
                965                 970                 975

Trp Asp Asp Tyr Lys Ile Pro Gly Gly Thr Phe Arg Glu Ser Val Phe
            980                 985                 990

Gly Arg Lys Phe Val Asp Lys Asp His Pro Ala Tyr Asp Leu Arg Trp
        995                 1000                1005

Arg Ser Asp Gln Thr Arg Glu Glu Phe Glu Lys Lys Leu Ala Glu
        1010                1015                1020

Leu Glu Lys Lys
        1025

<210> SEQ ID NO 7
<211> LENGTH: 546
<212> TYPE: PRT
<213> ORGANISM: Pichia pastoris

<400> SEQUENCE: 7

Met Ser His Leu Leu Arg Asp Ser Phe Trp Gly Arg Thr Ile Tyr
1               5                   10                  15

His Leu Ser Lys His Arg Tyr Phe Ser Phe Pro Glu Glu Lys Asp Gly
            20                  25                  30

Phe Ile Ala Pro Glu Lys Tyr Tyr Leu Asn Met Asp Gln Val Ser Ile
        35                  40                  45

His Ala Glu Ser Glu Lys Asn Ile Val Glu Gly Leu Val Asp Thr Ser
    50                  55                  60

-continued

```
Asn Ser Ser Leu Glu Glu Val Lys Thr Thr Arg Val Ile Val Asp Trp
 65                  70                  75                  80

Asp Glu Tyr Asp Gln Lys Glu Asn Pro Gln Asn Trp Ser Ser Leu Leu
                 85                  90                  95

Lys Cys Phe Val Val Phe Glu Val Gly Ile Leu Thr Val Ala Val Tyr
            100                 105                 110

Met Gly Ser Ala Ile Tyr Thr Pro Gly Ile Glu Asp Ile Met Arg Asp
        115                 120                 125

Leu Asn Val Ser Arg Thr Val Ala Thr Leu Pro Leu Thr Leu Phe Val
130                 135                 140

Ile Gly Tyr Ala Val Gly Pro Met Ile Phe Ser Pro Met Ser Glu His
145                 150                 155                 160

Pro Ala Ile Gly Arg Thr Thr Ile Tyr Val Trp Thr Leu Phe Ile Phe
                165                 170                 175

Ala Ile Leu Gln Ile Pro Thr Ala Leu Thr Thr Asn Ile Ala Gly Phe
            180                 185                 190

Cys Ile Leu Arg Phe Ile Gly Gly Phe Ala Ser Pro Ala Leu Ala
        195                 200                 205

Thr Gly Pro Ala Ser Val Gly Asp Val Ile Ala Ile Pro His Leu Pro
210                 215                 220

Val Gly Leu Gly Leu Trp Ser Ile Cys Ala Val Cys Gly Pro Ser Leu
225                 230                 235                 240

Gly Pro Leu Phe Gly Ala Ile Phe Ser Gln Leu Val Ser Trp Arg Trp
                245                 250                 255

Cys Phe Trp Phe Leu Leu Ile Thr Ser Gly Thr Leu Phe Ile Val Leu
            260                 265                 270

Gly Phe Thr Leu Pro Glu Thr Tyr Val Pro Thr Leu Leu Tyr Arg Lys
        275                 280                 285

Ala Arg Arg Leu Arg Ala Leu Thr Lys Asn Glu Leu Ile Ile Ser Lys
290                 295                 300

Gly Glu Leu Asp Ile Gln Asp Arg Thr Ala Lys Glu Val Leu Ile Glu
305                 310                 315                 320

Cys Leu Trp Arg Pro Val Asp Ile Ser Phe Arg Asp Pro Val Val Leu
                325                 330                 335

Met Ile Asn Leu Tyr Ile Ser Met Val Tyr Ser Ile Trp Tyr Ile Trp
            340                 345                 350

Phe Glu Ala Phe Pro Ile Val Phe Leu Glu Ile Tyr Gly Phe Ser Leu
        355                 360                 365

Ile Gly Met Gly Ala Ser Phe Ala Gly Ile Leu Ile Gly Val Leu Ile
370                 375                 380

Cys Ser Ala Cys Tyr Cys Tyr Ala Cys His Val Thr Phe Ala Arg Arg
385                 390                 395                 400

Ile Ile Ala Asn Glu Thr Ile His Pro Glu Phe Phe Val Pro Gly Ala
                405                 410                 415

Ile Ile Gly Gly Cys Ile Met Pro Thr Gly Ile Phe Ile Leu Gly Trp
            420                 425                 430

Thr Ala Thr Lys Ser Val His Trp Ile Val Pro Ile Ile Gly Ser Gly
        435                 440                 445

Leu Phe Ala Ala Gly Gly Tyr Leu Ile Phe Gln Thr Leu Phe Asn Tyr
450                 455                 460

Leu Ala Met Ser Phe Pro Arg Tyr Met Ala Ser Ala Phe Ala Gly Asn
465                 470                 475                 480
```

Asp Leu Phe Arg Ser Phe Ser Ala Ser Val Phe Pro Leu Phe Gly His
                485                 490                 495

Ala Leu Tyr Ala Asn Leu Gly Ser Glu Lys Phe Pro Val Gly Trp Gly
            500                 505                 510

Ser Ser Val Leu Gly Phe Ile Thr Val Ala Met Ile Ala Ile Pro Val
        515                 520                 525

Thr Phe Met Arg Tyr Gly Pro Arg Leu Arg Ala Asn Ser Arg Tyr Ala
    530                 535                 540

Gly Pro
545

<210> SEQ ID NO 8
<211> LENGTH: 355
<212> TYPE: PRT
<213> ORGANISM: Pichia pastoris

<400> SEQUENCE: 8

Met Thr Asp Tyr Val Thr Ser Lys Arg Pro Asp Asn Val Leu Asn Trp
1               5                   10                  15

Thr Ser Ile His Val Ser Ser Trp Ile Gly Glu Thr Ile Pro Glu Ile
            20                  25                  30

Asp Pro Ser Leu Leu Gln Asn Phe Leu Glu His Asp Ile Ala Gly Asp
        35                  40                  45

Val Leu Pro Tyr Leu Lys Ser Glu Asp Leu Lys Glu Ile Gly Ile Asn
    50                  55                  60

Glu Leu Lys His Arg Ile Ser Ile Lys Lys Asn Ile His Glu Leu Leu
65                  70                  75                  80

Val Ser Asn Glu Lys His Ile Asp Thr Ser Ile Leu Ser Asp Thr Ala
                85                  90                  95

Thr Glu Leu Gly Thr Leu Ile Leu Thr Asn Lys Phe Ile Thr Gln Met
            100                 105                 110

Ala Asn Arg Lys Asn Val Val Asp Asp Ser Thr His His Ser Asn Asn
        115                 120                 125

Arg Arg Leu Thr Glu Gln Phe Asn Lys Leu Arg Lys Asp Leu Leu Pro
    130                 135                 140

Ile Phe Lys Trp Ile Lys Glu Thr Gln Pro Leu Pro Thr Pro Glu Asn
145                 150                 155                 160

Thr His Phe Ala Asn Met Gly Ser Val Pro Ala Ser Pro Val Glu His
                165                 170                 175

Thr Ser Gly Glu Ser Thr Leu Ser Asn Pro Ser Leu Ser Thr Ile Asn
            180                 185                 190

Ala Gly Glu Gly Val Asn Ser Ala Val Ala Gly Gln Ser Leu Gly Arg
        195                 200                 205

Lys Pro Thr Leu Ser Ser Arg Arg Gln Ser His Ala Leu Ser Pro Thr
    210                 215                 220

Gly Glu His Leu Asn Val Ser Ser Ser Pro Ser Thr Gly Asn Phe
225                 230                 235                 240

Glu Thr Leu Asn Gly Glu Arg Pro Asn Leu Arg Ser Ala Ser Ser Gly
                245                 250                 255

Ser Gln Glu His Thr Glu Asn Glu Leu Leu Lys Pro Leu Arg Val Lys
            260                 265                 270

Ala Asp Glu Pro Cys Tyr Lys Val Ile Gln Asn Ala Met Lys Arg His
        275                 280                 285

Gly Leu Ser Val Asp Asp Trp Arg Lys Tyr Ala Leu Val Ile Cys Tyr
    290                 295                 300

```
Gly Asp Glu Glu Arg Val Leu Gly Leu His Glu Lys Pro Gly Ser Ile
305                 310                 315                 320

Phe Lys Glu Leu Lys Asp Gln Lys Gln Asn Pro Ala Ile Met Leu Arg
                325                 330                 335

Gln Ile Asp Thr Asn Asn Asp Asp Gln Asn His Ile Glu Thr Pro Gly
            340                 345                 350

Gly Arg Leu
        355

<210> SEQ ID NO 9
<211> LENGTH: 194
<212> TYPE: PRT
<213> ORGANISM: Pichia pastoris

<400> SEQUENCE: 9

Met Arg Phe Ser Asn Val Val Leu Thr Ala Ile Ala Ala Ala Gly Val
1               5                   10                  15

Gln Ala Asp Glu Ala Leu Tyr Thr Val Phe Tyr Asn Asp Val Thr Glu
                20                  25                  30

Asn Ala Gln Glu Tyr Leu Ser Tyr Ile Gln Ala Asn Thr Ala Ala Gly
            35                  40                  45

Phe Thr Asp Leu Leu Ser Leu Tyr Thr Glu Leu Ala Thr Tyr Thr Asp
50                  55                  60

Asp Ser Tyr Thr Ser Ile Phe Thr Glu Glu Asp Phe Pro Ala Ser Glu
65                  70                  75                  80

Leu Ser Ser Phe Val Val Asn Leu Pro Trp Tyr Ser Ser Arg Ile Glu
                85                  90                  95

Pro Gln Val Ala Ala Ala Glu Thr Gly Glu Ser Glu Glu Glu Ser Glu
            100                 105                 110

Thr Gly Glu Ser Glu Glu Ser Glu Thr Gly Glu Glu Thr Glu Thr
        115                 120                 125

Glu Thr Gly Ser Glu Ser Glu Ser Glu Ser Glu Ser Thr Ser Ala
    130                 135                 140

Thr Gly Thr Gly Thr Gly Thr Ser Ala Ser Glu Ser Ala Glu Thr Glu
145                 150                 155                 160

Thr Ser Thr Asp Ala Ala Val Ser Ile Asp His Pro Lys Ser Thr Leu
                165                 170                 175

Leu Met Gly Leu Thr Ala Ala Val Val Ser Ile Thr Phe Gly Val Phe
                180                 185                 190

Ala Leu

<210> SEQ ID NO 10
<211> LENGTH: 806
<212> TYPE: PRT
<213> ORGANISM: Pichia pastoris

<400> SEQUENCE: 10

Met Asn Lys Pro Asn Gly Ser Glu Gln Gln Pro Ser Arg Gly Met
1               5                   10                  15

Lys Gln Glu Ser Gly Gly Pro Val Thr Ser Ser Thr Thr Pro Gly Thr
                20                  25                  30

Asn Thr Gly Leu Glu Asn Ser His Ser Met Gly Ala Asp Met Glu Pro
            35                  40                  45

Asp Val Gly Ala Thr Ser Pro Arg His Leu Leu Asn Gly Tyr Ile Tyr
50                  55                  60
```

```
Asp Tyr Leu Val Lys Ser Asn Met Gln Asn Leu Ala Asp Gln Phe Ala
 65                  70                  75                  80

Gln Glu Thr Glu Leu Leu Glu Thr Asp Leu Thr Val Pro Met Asp Thr
                 85                  90                  95

Pro Ser Gly Tyr Leu Leu Glu Trp Trp Met Val Phe Trp Asp Leu Phe
                100                 105                 110

Asn Ala Arg Leu Lys Gln Arg Gly Ser Gln Lys Ala His Gln Tyr Ile
                115                 120                 125

Gln Leu Asn Met Leu Arg Gln Gln Gln Arg Thr Met Arg Asn Thr
            130                 135                 140

Ala Arg Val Gln Lys Val Pro Leu Arg Pro His Thr Gln Ser Ser Pro
145                 150                 155                 160

Ser Met Ser Gln Thr Phe Ile Pro Gln Gln Pro Gln Gln Gln Ala Gln
                165                 170                 175

Gly Gln Gln His Ala Gln Ala Gln Ala Gln Val Gln Ala His Gln Gln
                180                 185                 190

Ala Gln His His Ala Gln Ala Gln Val Pro Val Gln Pro Gln Gln His
                195                 200                 205

Gln Leu Gly Gly Gln Thr Gln Gln Gln Ser Ile Asn Thr Gly Ser
            210                 215                 220

Pro Ala Gly Pro Asn Ala Ile Asn Ser Arg Val Gln His Leu Ala Gln
225                 230                 235                 240

Gln Gln Met Asn His Leu Arg Gln Gln Ala Thr Ala Thr Gln Gln
                245                 250                 255

Pro Ile Pro Gln Gln Asn Ile Pro Ser Asn Gln Gln Gly Pro Thr Gly
                260                 265                 270

Pro Tyr Pro Thr Ser Pro Ser Arg Arg Pro Arg Leu Leu Ser Asn Glu
                275                 280                 285

Ser Gly Ala Ser Ala Pro Ser Val Met Thr Lys Ser Gln Leu Gln Gly
            290                 295                 300

Val Pro Pro Ser Gln Gln Pro His Gln Gln Gly Gln Gln Val Gly
305                 310                 315                 320

Pro Pro Asn Gln His Gln Gly Gln Ser Ser Phe Tyr Ser Gly Met
                325                 330                 335

Pro Pro Gln Gly Val Val Val Pro His Gln Phe Asn Pro Gln Gln Tyr
                340                 345                 350

Ala Asn Met Leu Ala Arg Gln Gln His Val Gln Ala Gln Gln Gln Val
                355                 360                 365

Gln Leu Gln Gln Val Gln His Val Gln Arg Gln Gln Gln Asp Gln
            370                 375                 380

Gln Gln His Arg Leu Ser Ala Gly Ser Pro Gly His Pro Ser Phe Gly
385                 390                 395                 400

Val Phe Gln Gln Pro Pro Met Ser Asn His Asn Gln Val Met Ile
                405                 410                 415

Asn Gln Gln Gly Glu Thr Phe Phe Asp Pro His Ser Pro Tyr Ala Gln
                420                 425                 430

Pro Asn Gly Tyr Pro Gln Pro Gln Gln Gln Gln Gln Gln Gln Gln
                435                 440                 445

Gln Gln Gln Gln Gln Pro Gln Gln Gln Gln Gln Gln Gln Gln Gln
            450                 455                 460

Gln Lys Gln Gln Pro Pro Pro Pro Arg Gln Pro Gln Arg Gln Gln
465                 470                 475                 480

Ala Met Ala Met Ala Pro Leu Pro His Ser Thr Ser Ala Ala Gly Thr
```

```
                485                 490                 495
Pro His Ser Ser Thr Thr Pro Arg Phe Ser Gln Pro Gly Pro Val Tyr
            500                 505                 510

Gln Gln Pro Leu Pro Ala Ser Gln Pro Gln His Ser Pro Pro Ser Ser
            515                 520                 525

Ile Gln Gln Pro Glu Leu Val Pro Thr Pro Gly Ser Gln His Gln Gln
            530                 535                 540

Ile Ala Gln Pro Gln Ser Gln Ser Gln His Gln Gln Ser Gln Gln Ser
545                 550                 555                 560

Gln Ser Ser Ala Ser Lys Ile Val Gly Ile Gln Glu Tyr Gln Lys Glu
                565                 570                 575

Leu Met Met Leu Glu Lys Gln Asn Lys Gln Arg His Asp Met Ala Cys
            580                 585                 590

Lys Lys Gly Ser Gly His Phe Ser Asn Phe Asp Pro Ile Pro Glu His
            595                 600                 605

Thr Pro Pro Glu Pro Lys Phe Asn Val Asn Val Met Leu Pro Pro Gln
            610                 615                 620

Asn Ser Ala Val Val Thr Lys Asn Thr Pro Gly Thr Ser Pro Gly Thr
625                 630                 635                 640

Gln Thr Gln Asn Thr Ala His Ser Thr Gly Asn Thr Ser Ala Gly Ser
                645                 650                 655

Thr Pro Asn Asn Val Ala Pro Val Arg Lys Lys Lys Glu Pro Ala Lys
            660                 665                 670

Lys Lys Ala Lys Lys Ala Thr Glu Pro Pro Thr Pro Thr Thr Pro Gln
            675                 680                 685

Thr Pro Ile Ala Ala Arg Thr His Gln Asn Ser Thr Gly Gly Ile Pro
            690                 695                 700

Gly Asn Asn Ala Ala Thr Lys Arg Arg Lys Arg Glu Pro Leu Val Asp
705                 710                 715                 720

Gln Thr Val Ser Pro Asn Leu Asn Glu Ala Ser Lys Ser Thr Lys Thr
                725                 730                 735

Gly Lys Ile Ser Ser Gln Thr Asp Phe Thr Gly Ser Asp Asn Gly Phe
            740                 745                 750

Leu Gln Asp Phe Gly Asp Gly Thr Gly Pro Pro Thr Gly Thr Asp Asp
            755                 760                 765

Met Glu Phe Asp Phe Asn Ser Phe Leu Asn Asn Glu Thr Gly Glu Pro
            770                 775                 780

Asn Ser Ser Thr Ile His Phe Asp Asn Val Phe Asn Trp Gly Glu Gly
785                 790                 795                 800

Thr Glu Ala Gly Asp Leu
                805

<210> SEQ ID NO 11
<211> LENGTH: 149
<212> TYPE: PRT
<213> ORGANISM: Pichia pastoris

<400> SEQUENCE: 11

Met Val Val His Asn Pro Asn Asn Trp His Trp Val Asp Lys Asn Cys
1               5                   10                  15

Leu Pro Trp Ala Lys Ser Tyr Phe Gln Glu Val Leu Pro Asn Thr Thr
            20                  25                  30

Gln Lys Asn Asp Ala Tyr Glu Ile Val Val Thr Ser Val Asp Leu Val
        35                  40                  45
```

```
Asp Gly Asp Cys Asp Val Thr Gln Arg Lys Gly Val Thr Lys Cys Ile
    50                  55                  60

Phe Asp Leu Lys Ile Gln Val Ser Ala Thr Val Lys Val Asn Thr Asn
 65                  70                  75                  80

Ser Glu Val Glu Ile Ser Tyr Thr Val Thr Leu Pro Glu Leu Val
                 85                  90                  95

His Asp Gln Asp Glu Asp Glu Tyr Glu Tyr Val Ile Glu Gly Asn Leu
                100                 105                 110

Asp His Lys Ser Gln Ile Arg Lys Leu Leu Thr Pro Leu Leu Thr Glu
            115                 120                 125

Lys Leu Ser Lys Phe Gln Gln Ala Leu Ile Asp Ala His Thr Gln Asp
130                 135                 140

Val Gln His Ser Thr
145

<210> SEQ ID NO 12
<211> LENGTH: 354
<212> TYPE: PRT
<213> ORGANISM: Pichia pastoris

<400> SEQUENCE: 12

Met Lys Ile Trp Leu Val Leu Leu Leu Val Phe Ala Thr Val Phe Ala
 1               5                  10                  15

Glu Thr Asp Tyr Tyr Lys Val Leu Gly Val Ala Lys Asn Ala Asp Glu
                20                  25                  30

Lys Asp Ile Lys Lys Ala Tyr Arg Ser Leu Ser Lys Lys Phe His Pro
            35                  40                  45

Asp Lys Asn Pro Gly Asp Asp Glu Ala Ala Gln Lys Phe Ile Gln Val
 50                  55                  60

Gly Glu Ala Tyr Asp Val Leu Gly Asp Pro Glu Lys Arg Gln Arg Tyr
 65                  70                  75                  80

Asp Arg Phe Gly Ala Glu Gly Leu Asp Ser Arg Gln Glu Gln Phe His
                 85                  90                  95

Asp Pro Phe Asp Met Phe Gln Gln Phe Phe Gly Gly Gly Gln Gln
                100                 105                 110

His Arg Gly Lys Pro Lys Gly Lys Ser Ser Leu Leu His Leu Glu Phe
            115                 120                 125

Ser Leu Gln Asp Phe Tyr Asn Gly Ala Ser Asn Asp Phe Arg Ile Glu
130                 135                 140

Met Gln Asn Ile Cys Glu Thr Cys Ser Gly Ser Gln Asp Gly
145                 150                 155                 160

Lys Val His Gln Cys Asp Thr Cys Lys Gly His Gly Arg Val Val Gln
                165                 170                 175

Thr Arg Gln Phe Gly Gly Met Gln Gln Arg Phe Glu Thr Ile Cys
                180                 185                 190

Pro Lys Cys Ser Gly Thr Gly Asn Leu Ile Thr His Lys Cys Lys Lys
            195                 200                 205

Cys Gln Gly Asn Arg Val Val Arg Gly Pro Arg Ile His Asn Val His
210                 215                 220

Leu Gly Ala Gly Thr Ser Arg Asn His Val Glu Ile Leu Glu Gly Gln
225                 230                 235                 240

Gly Asp Gln Ser Pro Asp Trp Ile Ala Gly Asp Leu Gln Ile Met Phe
                245                 250                 255

Lys Glu Lys Ala Glu Gly Asn Met Gly Tyr Arg Arg Ile Gly Asn Asn
                260                 265                 270
```

Leu Tyr Arg Asp Glu Ala Leu Thr Leu Lys Glu Ala Leu His Gly Gly
        275                 280                 285

Trp Glu Arg Gln Ile Ala Phe Leu Asp Lys Ile Glu Asn Thr Ile Thr
    290                 295                 300

Leu Ser Lys Lys Lys Gly Glu Val Val Asp Gly Gln Val Asp Thr
305                 310                 315                 320

Ile Lys Gly Arg Gly Met Pro Leu His Asp His Tyr Asp Glu His Gly
                325                 330                 335

Asp Leu Phe Ile Lys Tyr His Ile Ile Tyr Pro Gln Gln Ile Arg Asp
            340                 345                 350

Glu Leu

<210> SEQ ID NO 13
<211> LENGTH: 288
<212> TYPE: DNA
<213> ORGANISM: Pichia pastoris

<400> SEQUENCE: 13
atgttaaaca agctgttcat tgcaatactc atagtcatca ctgctgtcat aggcgagacg        60
actacgtcat ctaccactgc cagtctctcc gaaagcccta ctctggtttg ggtgactggc       120
actgatgcaa gtgggagatt ggcaactaca cagtctgctt acactcaaca gttttcacag       180
ttatactcat ccatagcatc tccatcaagt ggtagcatag gctgggtac tatccagggg        240 actgttggaa ttgtcagaac atatgagaca attacccttg ccagctaa                    288

<210> SEQ ID NO 14
<211> LENGTH: 261
<212> TYPE: DNA
<213> ORGANISM: Pichia pastoris

<400> SEQUENCE: 14
atgtctacag caattccagg aggacagaga acgttagcta aagaagagc agcaaacttg         60 gataagaaac aggatgaacc aacctccgcc agatctgccg gtgctggagg ttcttcgtct       120
accatgctaa agttgtacac agacgaggcc caaggtttga agttgatcc tttaattgtt       180 cttgttcttg ctgttggttt catttcagt gtcattggtt tgcacgttgt tgctaagctg       240
acaggaaagt tgatcaacta a                                                 261

<210> SEQ ID NO 15
<211> LENGTH: 1086
<212> TYPE: DNA
<213> ORGANISM: Pichia pastoris

<400> SEQUENCE: 15
atgactcccc gttctcatat tttctttgac atctccatca caaccagcc agctggcaga         60 ataatctttg agctcttcaa tgacattgtt cctaagacag cagagaattt tagagcttta       120
tctactggtg agaaaggtat aggtaagtct gggaaaccat gcactacaa gggttctact        180 ttccatagga tcattaagga ttttatggta caaggtggtg actttaccaa cggtaacggt       240 actgaggcg aatccatata tggagaaaaa tttgaagatg aaaatttcca attgactcat        300
gacaaaccgt tccttctctc tatggcaaac gctggaccag aactaatgg atcccagttt       360 tttatcacca ccgttcctac tcctcatctg gataacaagc atgtagtgtt tggaaaagta      420
attgctggta agccacagt tagaaagatt gaaagaaact ccgaaggtga agctccaatt       480
gaacccgttg tcattgagga ctgtggtgaa cttccagaag acgcagattt gaccatctcc      540

```
gacgagactg gagacaagta tgaggaagtt ctgaaagata atgagaacat agacatcgat      600
gactttgaac aggtctacca ggccatcact gaaatcaaag aattgggtac aaagtatttc      660
aaaaatggtg acaccaaaat cgccttcgaa aagtatcaaa aggctgctaa ttatttgctg      720
gaatacatac catcagattt atcagaggaa cagagctcta agttggagct gctaaaaaca      780
tctgtcttct ccaacgtggc attggctgga ctgaaagttt ccaagttcaa agacacgatt      840
aagtatgcca cattggtcat tgaggatgaa tctgcggatg caaaggccaa gtccaaaggc      900
tactaccgta gaggaagtgc ttacagctca ctgaaagacg aagattcagc catctcagat      960
ttccagaaag cacttgaatt atccccaggt gatcctgcaa ttagccaatc tctacaaaga     1020
accacgaagg ccagaaaaga ccgtcttgcc aaagagaaag ctgctttgtc taagttcttt     1080
gagtag                                                                1086

<210> SEQ ID NO 16
<211> LENGTH: 825
<212> TYPE: DNA
<213> ORGANISM: Pichia pastoris

<400> SEQUENCE: 16
atgtcgtctg atgctgtgga gcaacttgaa aacttccagt tgatcaagtt cgacagattc       60
gatccttcaa cgcaatcgac tatcagaata gcgcgatctc ccaaaccaat tccagtcaag      120
gttgtgatag tgggagatgg tggatgtgga aagacatgtc ttctcaatgt ctttgccact      180
ggaacgtttc ctgaggcgta tgtccccaca atcatagaaa atgtggttat tacattggtg      240
accccaactg gccagatagc tgccgttact ctgtgggata ctgcagggca agaagagtac      300
gacagattga ccccctaag ctactccgac gttgacgtgg tcttgctgtg ctacagcata      360
gacaatctgt ccacctttca taatgtggcc gacaaatggt acccagaagt ggcacatttt      420
tgtccaaaca caccgatcat cttggtaggt accaaatctg atatgcggcg tcatcagaag      480
agtcagccgc actttgtatc tccccaggat tcgtcgcagt tggcaaggca gatgggggca      540
gtgatgaaca tcgagtgttc tgcgaaggag gtttcaaacg tcaatatcgt ttttgatgct      600
gctgtgtcgt actgtttgag taacagcagg cccaagacca gagggataa tgacaacaat      660 aggagtaaca gacggctaag tagagccaag cgagccagca tgtttataag gggtaaggat      720
gttagctcaa cgtcaggaaa ctctcgggaa gaacttgttg aatacgatca agatgggttg      780
gcaataatac cggacagaaa gaaacgcaaa tgtagcatta tttga                     825

<210> SEQ ID NO 17
<211> LENGTH: 384
<212> TYPE: DNA
<213> ORGANISM: Pichia pastoris

<400> SEQUENCE: 17
atgactaact ggaaagcgat attgactccc gctcaatacc aagtcctccg tttgggcgga       60
acagaaagac cgtataccgg acagtatgtg aacttcaaga aaaatggaac ctacttgtgt      120
agtgggtgtc aaactccgct ttacaaaagt ggcacaaaat ttgattcatc ttgtggttgg      180
cctgcattct atgaagcatt acctggagca gttaaacgaa tagaagacaa ttcgcttgga      240
atgcgaagaa tagaaatcag atgctccaaa tgtgatggac atcttggcca tgttttttgag      300 ggtgagggat ttgacactcc aacagattcc agacattgtg tcaacagcat cagcctaaaa      360
tttcaaggtg aagaagagaa ctaa                                             384
```

<210> SEQ ID NO 18
<211> LENGTH: 3084
<212> TYPE: DNA
<213> ORGANISM: Pichia pastoris

<400> SEQUENCE: 18

| | | | | | | |
|---|---|---|---|---|---|---|
| atgactacaa | acggccagaa | agacaaaaa | actcgcaaac | cacttttgat | caacgcattt | 60 |
| gtcatgggat | gtgctgggtt | acagaatcct | ggtttatgga | agcatcccaa | ggactcatcc | 120 |
| catagattta | atcagattga | tcactggact | tatttggcca | agttagccga | aaaggggaag | 180 |
| tttaatgcgc | tcttcattgc | cgacgtcttg | ggtggctatg | atgtctacaa | aggacctgag | 240 |
| aatttagcca | ctcctgctgt | ggctggagcc | cagtggcctg | tcaccgagcc | cagtgctgtg | 300 |
| gtctccgcca | tggctgcagt | cacaactaac | ttggcgtttg | gagtgacgtt | ctctactatc | 360 |
| agcgaagccc | cctatcattt | tgccagaaga | ctgtccactt | tagaccactt | gaccaagggt | 420 |
| agaataggat | ggaatgttgt | ttcatcttac | ttggagagtg | ctgctcgtaa | cctcttgaat | 480 |
| ggtgaaaaat | tggacgagca | tgaccaagga | tacttgaaag | ctgaagagta | cattcaaata | 540 |
| gtttatgagc | tgttgttatc | gtcttggaga | gatgatgcag | tagttttaga | caagaaagct | 600 |
| ggtgtttata | ctgacccaac | aagatttcga | aagatcaact | tgaaggtaa | attttttcaaa | 660 |
| gttccgggac | acatattgt | tgaccccacc | cctcaaagac | tgcctgtgat | tcttcaagct | 720 |
| ggtacttcta | agttggtaa | ggagtttgct | gctaagcatg | ccgagattgt | gtttgtcatt | 780 |
| tcattttctc | cagatgattt | gaaacccaag | attgcagaag | ttcgtcaact | ggccaaagaa | 840 |
| aagtttggta | gaaaccacga | cgatattaag | tttgttgccc | ttgcaacccc | tgttattgga | 900 |
| gccacacatg | aactagctga | agaaaagtac | caagagttac | taagttatgg | tgatattgaa | 960 |
| ggtgctcaag | cctatttgg | agggtggact | ggcattgacc | tctctcaata | tggcgaagat | 1020 |
| gaagaactag | gaaatgttag | ttccaatgct | atgcgtggcg | ctgtacaaaa | ctggactaaa | 1080 |
| gcaattccaa | atgagaagcg | ttggacacgt | aaggttattg | ctaaacagat | taccgttggt | 1140 |
| ggtctaggtc | cagcttctcgt | tggaaccccca | aagaaatcg | ccgatgagct | ggaacactgg | 1200 |
| tccgaccacg | ctggtttgga | cggattcaac | ttcacttatg | ctgtcaaccc | gctttctttc | 1260 |
| gaagagatag | tggaagactt | gattccagtt | cttcagcgaa | gagggttggc | ccaaaaggaa | 1320 |
| tacccaaatc | cagaaactgg | aagcacattc | cgtaaaaacc | ttttttggaac | agactttgta | 1380 |
| ccatctaccc | acccagctta | taacttaaga | tggagggctg | gtgtgtccaa | ggaagaattc | 1440 |
| gaaaagtccc | taaacgccac | aacaaattgg | tattccagtt | tcgctaggtc | aggtgctcta | 1500 |
| ggtgaattgc | ataatacatg | caggattctc | tatctccaaa | tagtgaaata | aaatatagg | 1560 |
| cttcgagtcc | gttcagaagg | gaatagcatc | cccttcgcca | aaatgaccaa | ggaaaatgaa | 1620 |
| gccaagaggc | agaaaacctc | tcaaccaaaa | gcgaagaagc | aattgattat | caatgctttc | 1680 |
| atgtcaggct | cttcgggtaa | ccaatcgcca | ggactgtggt | cgtaccctgg | agacaaatca | 1740 |
| acagagtata | ctaccctaga | ttactgggtg | gagttagctc | aaaagctgga | aaaggccaaa | 1800 |
| ttccattcta | tcttcattgc | cgatgttctg | ggtggatatg | acgtttacaa | tggacctgga | 1860 |
| aactacagtg | ctgctgcaaa | atctggtgcc | caatttccaa | tgattgaacc | aagtgctgca | 1920 |
| gttactgcca | tggctgctgc | taccaagtca | ataacgttcg | gagtgacttt | ttccactata | 1980 |
| agtgaggcac | cttatcattt | tgcaagaaga | ttgggaactt | tagatctgct | gacaaacgga | 2040 |
| agagtcggct | ggaatatcgt | ctcttcgtat | cttgacagtg | ccgccagaaa | tcttttgaat | 2100 |
| ggagaaccac | tccctctcca | tgcagaccgt | tataagagag | ccgaagaatt | cctacaagtt | 2160 |

```
gtatatcggt tattcctttc ttcatggaga gacgatgctt ataaattgga taagaaaacc    2220
agaacctttg ctgacccaaa acttattaga actatcgacc acgttggaga gttcttcaat    2280
gtcccaggcc cccagttcct accacccact cctcagagac taccgctgat tttgcaggct    2340
ggtacttcca aggttggtat ggattatgct gcaaaacatg cagaggttgt cttttttagct   2400 tcatttgacc cagagtcact ccaagaaaaa atcaaaacag tgagagatat cgctgaaacc    2460
aagtacaaca gaccaagaga ttcaatcaaa ttcttaattt tgataacagt agtcatagct    2520
gatacacacg aagatgccgt gaagagatac gaagatctcg ccagttatgc tgatctggaa    2580 gggcccaag cactgttcag tggttggact ggaatagata ttggaaagta tggtgaagat     2640
gaacctcttg agcatgtgga atctaacgct attaagagcc atgttaagaa ctggactaag    2700
ttcaaggaca ataagcctag agccagaaaa gatatcgcta acagattgg agttggaggc    2760 tcaggtccct tacttgttgg atctgtacaa gagatagccg acgagcttga gagatgggca    2820
gaagtctctg acctcgatgg ctttaacttc gcttacgcag attacccca aacttttgat     2880 gatatcattg aaaaactgct tccagagttg aacaagagag tgtgttctg ggatgattat      2940 aaaattccag gtggaacctt cagagagagc gtgtttggaa gaaagttcgt tgataaggat    3000
catcctgctt atgatctgag atggagaagt gaccaaacta gggaggagtt tgaaaagaaa    3060
ctggctgaat tggagaaaaa ataa                                           3084
```

<210> SEQ ID NO 19
<211> LENGTH: 1641
<212> TYPE: DNA
<213> ORGANISM: Pichia pastoris

<400> SEQUENCE: 19

```
atgtctcatc tattactgcg tgacagcttt tggggaagga ccatctacca tctgagtaaa     60
cacaggtatt tctctttttcc tgaagagaaa gatggtttca ttgctcctga aaagtactac    120
ctgaatatgg accaagtatc gatacatgct gaatctgaga aaaatatagt ggaaggtttg    180
gtagacactt caaattcttc gttggaggaa gtaaagacca ctagagtcat agtcgactgg    240
gatgaatatg atcagaaaga aaatccccaa actggagct cgcttttaaa gtgcttcgtt    300 gttttttgaag tgggaatctt aaccgtagct gtttatatgg gatctgcaat ttacactccc    360
ggtatagaag atattatgag agatctcaat gttagcagaa cggtggcaac acttccatta    420
accttgtttg tgattggata cgctgtgggt ccaatgatat tctcccccat gtctgagcat    480
cccgctatcg gaaggacaac gatatatgtg tggaccctgt tcatatttgc tatactacaa    540
atcccaacgg ccctgaccac taacattgct ggatttttgca ttttgaggtt tattggaggg   600
ttttttgcgt caccagcatt agctacaggt ccagcttctg taggtgatgt tattgcaatc    660
ccgcacttgc ctgtagggtt aggcctttgg agtatctgtg ctgtttgtgg tccttctcta    720
ggaccacttt ttggagccat attttcccaa cttgtgagtt ggaggtggtg cttcggttt     780 ctgttaatta cctctgggac actatttata gttcttggct tcactttacc agaaacgtat    840
gtaccaaccc ttctttacag aaaggctagg aggctacgag cattaacaaa aaacgaactg    900
attatcagca aagggagtt agatattcag gacagaactg ccaaggaagt tttgattgaa    960
tgcttatgga ggccagtcga catatcattc agagaccccg ttgtcttgat gataaatctt    1020
tacatttcaa tggtttattc tatttggtac atttggtttg aagcgtttcc tattgtattc    1080
ttagagatat atggattcag ccttattgga atgggagcta gttttgccgg aatcttaatt    1140
```

```
ggtgtcttaa tatgctctgc gtgctattgc tatgcgtgtc atgttacttt tgcaagaaga    1200
ataattgcaa acgaaaccat tcatcctgag ttctttgtac cgggcgctat tattggaggt    1260
tgcataatgc ccactggaat ctttattttg ggatggactg ccaccaaaag tgtccactgg    1320
attgtaccta taataggtag cggtttattt gctgctggtg gttatctcat tttccagaca    1380
ctcttcaact accttgcaat gtctttccct agatacatgg catcagcttt tgccggaaat    1440
gatcttttca ggtccttttc tgccagtgtt ttcccactgt ttggacatgc actatatgcc    1500
aacttgggat ccgaaaagtt ccctgttggt tggggttctt ctgtactggg gttcatcact    1560
gttgcaatga tcgcaattcc agtaactttc atgagatatg gtccaagatt gcgtgcaaat    1620
tctagatatg ccgggccatg a                                              1641
```

<210> SEQ ID NO 20
<211> LENGTH: 1068
<212> TYPE: DNA
<213> ORGANISM: Pichia pastoris

<400> SEQUENCE: 20

```
atgacggact atgtcacttc taagcggcca gataacgtgc tcaattggac aagtattcat     60
gtatcgtcct ggatagggga gactattcct gagatcgatc caagtctact ccaaaatttt    120
ttagaacatg acattgcggg agatgttcta ccctacttga agtctgaaga tctgaaggaa    180
attgggatca acgagctcaa gcacagaatc tctataaaaa agaacattca tgaacttctt    240
gtgagcaatg aaaagcacat tgataccagt attctatcag acaccgctac cgagctagga    300
actttgatac tgactaataa attcataacc cagatggcga acagaaagaa tgttgtagat    360
gattccactc atcattcgaa taacagaagg ctcactgaac agtttaataa gcttcgcaaa    420
gatcttttgc cgatattcaa atggatcaag agacccaac cattaccac tccagagaat     480 acacatttcg caaatatggg ttcagtacca gcatctcctg tggagcatac ttcaggtgag    540
tcaacattgt ctaaccccag tctaagcacc atcaatgctg cgaaggagt gaactctgca    600 gttgcagggc aatctctcgg gaggaaacct acattatcct ccagaagaca atcacatgct    660
ttgtctccaa ctggtgaaca cctgaatgtg tcatcatcat ctccttcgac ggggaattt    720 gaaactctga atggagaaag acccaatctt agatctgctt cgtcaggatc acaggaacat    780
actgagaacg aactattgaa gccgttgaga gttaaagcag atgagccttg ctataaggtg    840
attcagaatg ccatgaaaag acatggctta tcggtagatg attggcgcaa gtatgctttg    900
gtcatctgct atgagatga agaacgagta ctaggcttac atgaaaaacc tgggagtatc     960
ttcaaggaac tcaaagatca gaaacagaat cctgcaatca tgcttcgtca aattgacact    1020
aataatgacg atcagaacca tattgaaacc cctggaggga gattatga                 1068
```

<210> SEQ ID NO 21
<211> LENGTH: 585
<212> TYPE: DNA
<213> ORGANISM: Pichia pastoris

<400> SEQUENCE: 21

```
atgagatttt ctaacgtcgt tttaactgca attgccgctg ccggcgtaca ggcagatgaa     60
gccctttaca ctgtgttcta caatgatgtc actgagaacg cccaagagta tctgtcttac    120
atccaggcca atactgcggc tggtttcact gacctcttga gtctgtacac tgaactggcc    180
acttacaccg acgattctta cacaagtatc tttactgagg aggatttccc tgcgagcgaa    240
cttttcatcg tctcgttgtt aacctgccat ggtattcctc ca gaattgagcc acaagttgcg    300
```

```
gctgctgaaa ctggtgaaag tgaggaggaa tcagagactg gtgaaagtga ggaagaatca      360
gagactggtg aggagacaga aactgagact ggatctgagt ctgaatctga gtctgaatcg      420
gagacctccg ctactggcac tggcactggc acctccgcct ctgagagcgc ggagactgaa      480
acttctaccg acgctgctgt gtctatcgat cacccaaagt ccaccttatt gatgggtttg      540
actgccgcag ttgtcagtat cactttcgga gtctttgcct tgtaa                     585
```

<210> SEQ ID NO 22
<211> LENGTH: 2421
<212> TYPE: DNA
<213> ORGANISM: Pichia pastoris

<400> SEQUENCE: 22

```
atgaacaagc caaacgggtc tgaacaacaa ccaccgtcac gcggaatgaa gcaagagtca       60
ggaggcccag ttacttcatc tacgacgccg ggtaccaata ctggcctaga aaactctcat      120
tccatggggg cggatatgga gcctgatgtt ggtgctacct ctcctcgcca tcttcttaat      180
gggtacattt acgattattt agtcaaatct aacatgcaaa atttggctga tcaatttgcc      240
caagagacga agctcttaga aacagacttg acagtaccaa tggatacgcc ttcaggctat      300
cttctagaat ggtggatggt attctgggac cttttcaatg cccgcctaaa gcaacggggt      360
tcacagaagg cccaccagta tattcagttg aacatgctac gacaacagca acagaggacc      420
atgcgaaata cagcccgtgt tcaaaaagtc ccgttgaggc cacacaccca atcatctcct      480
tcaatgtcac agacttttat tccacagcag cctcaacagc aagcacaggg acaacagcac      540
gcccaggctc aagcccaagt gcaagcacat cagcaagccc aacaccacgc gcaggcacaa      600
gtgccagtgc aaccgcaaca gcaccagcta ggaggccaaa ctcaacagca gcaatccatt      660
aacactgggt ctcctgcggg tccaaatgct atcaactcgc gtgttcaaca cttagcacaa      720
caacagatga atcaccttcg ccagcaggcg actgccacta cgcaacaacc tatcccgcaa      780
cagaatatcc catcaaacca acagggtcct acaggcccct atcctacttc cccttcaaga      840
agaccgagat tactgtctaa cgaatcgggt gcaagtgcac cctctgtaat gacaaagtca      900
cagctccaag gagtccctcc ctcacaacaa ccacaccagc agcaaggtca gcaggtaggc      960 cccctaatc aacatcaagg tcaatcttct tcctttatt cgggcatgcc tcctcaaggg       1020
gtcgtggttc ctcatcagtt caatcctcag cagtatgcca atatgctagc aagacaacag     1080
catgtacaag ctcaacaaca ggttcagtta caacaggtcc aacatgtaca acagagacaa     1140
cagcaagacc aacaacaaca ccgcctgtcc gccggttcac cggggcaccc ttcatttggc     1200 gttttcaac aacctcctcc gatgtcaaac cataatcagg tcatgatcaa tcagcaggga     1260 gaaactttt ttgatccaca ttctccatat gctcaaccta cgggtaccc ccagccacag      1320 caacaacaac aacaacagca caacaacaa caacagcagc aaccgcaaca gcagcagcag     1380
cagcagcagc aacagaagca gcaaccacca ccaccaccac gacagcctca cgccaacaa     1440 gcgatggcca tggctcctct gcctcactct acttctgccg ccggtactcc tcactcgtcc     1500
accacaccta gattctcgca acctggtcct gtttatcagc agcctttacc tgcatctcaa     1560
ccgcaacatt ctccgccttc ttctattcag cagccggagc tagttccaac tccagggtca     1620
caacatcagc aaatagcaca accacaatca cagagccaac accagcaatc gcaacagtct     1680
caatcaagtg cttctaaaat tgtaggtata caggagtatc agaaagagct aatgatgctt     1740
gagaaacaga acaaacagcg tcatgacatg gcatgtaaga agggaagcgg gcatttttct     1800
```

```
aactttgatc caattccaga gcacacaccg cccgaaccaa aatttaatgt gaatgtaatg    1860
ctccctcccc agaactctgc agtggtcacg aagaatactc ccggaacttc acctggtaca    1920
caaactcaaa acactgcaca tagtactggt aacacttctg cggggtctac accaaataat    1980
gtcgcacctg tacgaaagaa aaaggagcca gctaaaaaga aggcaaagaa agctactgag    2040
cccccgactc ccactactcc acagactcca attgcagcta ggacacatca aaactctaca    2100
ggcggcattc ctggtaataa tgctgctact aagcgacgaa aacgggagcc gctggttgat    2160
caaactgttt cacctaacct taacgaagct tccaagtcaa caaagaccgg aaaaatttca    2220
tctcaaactg actttacagg ttctgacaat ggattcttac aggattttgg cgatggaact    2280
ggtcctccca ctggaaccga tgatatggaa tttgatttta acagtttttct taataacgaa    2340 actggcgaac ctaatagttc aaccattcat tttgacaatg tattcaattg gggagaaggt    2400
accgaagccg gagatttata g                                              2421

<210> SEQ ID NO 23
<211> LENGTH: 450
<212> TYPE: DNA
<213> ORGANISM: Pichia pastoris

<400> SEQUENCE: 23
atggtggtgc acaaccctaa taactggcac tgggtcgaca agaactgcct tccttgggcc    60
aaaagctact ttcaggaagt ccttccaaac accactcaga gaatgacgc ctatgaaata    120 gtggtaacat ctgtggacct tgtagatgga gactgcgatg tcactcaacg taaaggtgtt    180
accaaatgta tttttgatct gaagatacag gtatctgcaa ccgtcaaagt caacacgaac    240
agtgaagtag aggagatcag ttatacagtg acattacctg aactggtgca cgaccaggac    300
gaggatgaat atgaatacgt aatagaggga aatttgatc acaagtctca aattagaaag    360
ctactcactc ctctgttgac cgagaagtta tcaaagtttc aacaagcttt gatagacgct    420
catactcagg atgttcagca tagtacctag                                     450

<210> SEQ ID NO 24
<211> LENGTH: 1065
<212> TYPE: DNA
<213> ORGANISM: Pichia pastoris

<400> SEQUENCE: 24
atgaagatat ggctggtact tcttttagtt tttgccacgg tgtttgccga cagagattat    60
tataaagttc ttggagtagc taaaaatgcg gatgaaaaag atatcaagaa ggcctacaga    120
tcgttgagta agaagtttca tccagataag aacccgggtg atgatgaagc cgctcaaaag    180
ttcattcaag ttggagaagc ttatgatgtg cttggtgatc ccgagaagcg tcaaaggtat    240
gacagatttg gagcagaagg actggactca agacaggaac aattccatga tccatttgac    300
atgtttcaac agttcttcgg aggaggtgga cagcaacaca gaggcaaacc aaagggtaag    360
agttccttgt tacatttaga attcagtcta caagactttt acaatggtgc tagtaacgac    420
tttagaatcg aaatgcagaa tatctgtgaa acttgttctg gatcaggttc acaagacggg    480
aaagttcatc aatgtgacac ttgcaaaggg cacgggcgtt tgttcaaac gagacagttt    540 ggtggtggca tgcaacagag gtttgaaaca atttgcccaa aatgttcagg aacaggaaat    600
ctgatcactc acaagtgtaa gaaatgccaa ggaaaccgtg tagttagagg acccagaatt    660
cacaatgtgc atttgggggc gggaactagt aggaaccatg ttgagatcct ggaaggtcag    720
ggagaccagt ctccagactg gattgcaggt gatctacaaa tcatgttcaa ggagaaagcc    780
```

```
gaaggcaaca tggggtatag aagaatagga acaaacctgt acagagacga agcattaacg    840
ctgaaagagg cattgcatgg tggctgggag agacaaattg cgttttgga taaaatagag     900 aacacgatta ctctttccaa gaagaaagga gaggtggtag ttgacggcca agtagacacc    960 atcaaggta gagggatgcc attacatgac cactatgacg aacatggtga tctctttatc    1020
aagtaccata tcatttaccc gcaacaaatt agagacgaat tgtga                   1065
```

<210> SEQ ID NO 25
<211> LENGTH: 312
<212> TYPE: PRT
<213> ORGANISM: artificial
<220> FEATURE:
<223> OTHER INFORMATION: Synthetic Construct

<400> SEQUENCE: 25

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Val Gln Leu Val Gln Ser Gly Gly Gly Leu
                85                  90                  95

Val Gln Pro Gly Gly Ser Leu Arg Leu Ser Cys Ala Ala Ser Gly Phe
            100                 105                 110

Thr Phe Ser His Tyr Trp Met Ser Trp Val Arg Gln Ala Pro Gly Lys
        115                 120                 125

Gly Leu Glu Trp Val Ala Asn Ile Glu Gln Asp Gly Ser Glu Lys Tyr
    130                 135                 140

Tyr Val Asp Ser Val Lys Gly Arg Phe Thr Ile Ser Arg Asp Asn Ala
145                 150                 155                 160

Lys Asn Ser Leu Tyr Leu Gln Met Asn Ser Leu Arg Ala Glu Asp Thr
                165                 170                 175

Ala Val Tyr Phe Cys Ala Arg Asp Leu Glu Gly Leu His Gly Asp Gly
            180                 185                 190

Tyr Phe Asp Leu Trp Gly Arg Gly Thr Leu Val Thr Val Ser Ser Ala
        195                 200                 205

Ser Thr Lys Gly Pro Ser Val Phe Pro Leu Ala Pro Cys Ser Arg Ser
    210                 215                 220

Thr Ser Glu Ser Thr Ala Ala Leu Gly Cys Leu Val Lys Asp Tyr Phe
225                 230                 235                 240

Pro Glu Pro Val Thr Val Ser Trp Asn Ser Gly Ala Leu Thr Ser Gly
                245                 250                 255

Val His Thr Phe Pro Ala Val Leu Gln Ser Ser Gly Leu Tyr Ser Leu
            260                 265                 270

Ser Ser Val Val Thr Val Pro Ser Ser Ser Leu Gly Thr Lys Thr Tyr
        275                 280                 285

Thr Cys Asn Val Asp His Lys Pro Ser Asn Thr Lys Val Asp Lys Arg
    290                 295                 300

Val Glu Ser Lys Tyr Gly Pro Pro
```

<210> SEQ ID NO 26
<211> LENGTH: 299
<212> TYPE: PRT
<213> ORGANISM: artificial
<220> FEATURE:
<223> OTHER INFORMATION: Synthetic Construct

<400> SEQUENCE: 26

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Ala Ile Gln Leu Thr Gln Ser Pro Ser Ser Leu
                85                  90                  95

Ser Ala Ser Val Gly Asp Arg Val Ile Leu Thr Cys Arg Ala Ser Gln
            100                 105                 110

Gly Val Ser Ser Ala Leu Ala Trp Tyr Gln Gln Lys Pro Gly Lys Ala
        115                 120                 125

Pro Lys Leu Leu Ile Tyr Asp Ala Ser Ser Leu Glu Ser Gly Val Pro
    130                 135                 140

Ser Arg Phe Ser Gly Ser Gly Ser Gly Pro Asp Phe Thr Leu Thr Ile
145                 150                 155                 160

Ser Ser Leu Gln Pro Glu Asp Phe Ala Thr Tyr Phe Cys Gln Gln Phe
                165                 170                 175

Asn Ser Tyr Pro Leu Thr Phe Gly Gly Gly Thr Lys Leu Glu Ile Lys
            180                 185                 190

Arg Thr Val Ala Ala Pro Ser Val Phe Ile Phe Pro Pro Ser Asp Glu
        195                 200                 205

Gln Leu Lys Ser Gly Thr Ala Ser Val Val Cys Leu Leu Asn Asn Phe
    210                 215                 220

Tyr Pro Arg Glu Ala Lys Val Gln Trp Lys Val Asp Asn Ala Leu Gln
225                 230                 235                 240

Ser Gly Asn Ser Gln Glu Ser Val Thr Glu Gln Asp Ser Lys Asp Ser
                245                 250                 255

Thr Tyr Ser Leu Ser Ser Thr Leu Thr Leu Ser Lys Ala Asp Tyr Glu
            260                 265                 270

Lys His Lys Val Tyr Ala Cys Glu Val Thr His Gln Gly Leu Ser Ser
        275                 280                 285

Pro Val Thr Lys Ser Phe Asn Arg Gly Glu Cys
    290                 295

<210> SEQ ID NO 27
<211> LENGTH: 939
<212> TYPE: DNA
<213> ORGANISM: artificial
<220> FEATURE:
<223> OTHER INFORMATION: Synthetic Construct

<400> SEQUENCE: 27

```
atgagattcc catctatttt caccgctgtc ttgttcgctg cctcctctgc attggctgcc    60
cctgttaaca ctaccactga agacgagact gctcaaattc cagctgaagc agttatcggt   120
tactctgacc ttgagggtga tttcgacgtc gctgttttgc ctttctctaa ctccactaac   180
aacggtttgt tgttcattaa caccactatc gcttccattg ctgctaagga agagggtgtc   240
tctctcgaga agagagaggt ccaattggtc aatctggtg gaggattggt tcaaccaggt    300
ggatctctga gattgtcttg tgctgcttct ggtttcacct ctctcacta ctggatgtca    360
tgggttagac aagctcctgg taagggtttg gaatgggttg ctaacatcga gcaagatgga   420
tcagagaagt actacgttga ctctgttaag gaagattca ctatttcccg tgataacgcc    480
aagaactcct tgtacctgca aatgaactcc cttagagctg aggatactgc tgtctacttc   540
tgtgctagag acttggaagg tttgcatggt gatggttact tcgacttatg gggtagaggt   600
actcttgtca ccgtttcatc tgcctctacc aaaggacctt ctgtgttccc attagctcca   660
tgttccagat ccacctccga atctactgca gctttgggtt gtttggtgaa ggactacttt   720
cctgaaccag tgactgtctc ttggaactct ggtgctttga cttctggtgt tcacacctt   780
cctgcagttt tgcagtcatc tggtctgtac tctctgtcct cagttgtcac tgttccttcc   840
tcatctcttg gtaccaagac ctacacttgc aacgttgacc ataagccatc caataccaag   900
gttgacaaga gagttgagtc caagtatggt ccaccttaa                          939
```

<210> SEQ ID NO 28
<211> LENGTH: 900
<212> TYPE: DNA
<213> ORGANISM: artificial
<220> FEATURE:
<223> OTHER INFORMATION: Synthetic Construct

<400> SEQUENCE: 28

```
atgagattcc catctatttt caccgctgtc ttgttcgctg cctcctctgc attggctgcc    60
cctgttaaca ctaccactga agacgagact gctcaaattc cagctgaagc agttatcggt   120
tactctgacc ttgagggtga tttcgacgtc gctgttttgc ctttctctaa ctccactaac   180
aacggtttgt tgttcattaa caccactatc gcttccattg ctgctaagga agagggtgtc   240
tctctcgaga agagagctat ccagttgact caatcaccat cctctttgtc tgcttctgtt   300
ggtgatagag tcatcctgac ttgtcgtgca tctcaaggtg tttcctcagc tttagcttgg   360
taccaacaaa agccaggtaa agctccaaag ttgctgatct acgacgcttc atcccttgaa   420
tctggtgttc cttcacgttt ctctggatct ggatcaggtc ctgatttcac tctgactatc   480
tcatcccttc aaccagaaga ctttgctacc tacttctgtc aacagttcaa ctcttaccct   540
ttgacctttg gaggtggaac taagttggag atcaagagaa ctgttgctgc accatcagtg   600
ttcatctttc ctccatctga tgagcaactg aagtctggta ctgcatctgt tgtctgctta   660
ctgaacaact tctacccaag agaagctaag gtccaatgga aggttgacaa tgccttgcaa   720
tctggtaact ctcaagagtc tgttactgag caagactcta aggactctac ttactcccct   780
tcttccaccc tgactttgtc taaggctgat tacgagaagc acaaggttta cgcttgtgag   840
gttactcacc aaggttttgtc ttctcctgtt accaagtctt tcaacagagg tgaatgctaa    900
```

<210> SEQ ID NO 29
<211> LENGTH: 303
<212> TYPE: PRT
<213> ORGANISM: artificial
<220> FEATURE:
<223> OTHER INFORMATION: Synthetic Construct

<400> SEQUENCE: 29

Met Arg Phe Pro Ser Ile Phe Thr Ala Val Leu Phe Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
50                      55                  60

Phe Ile Asn Thr Thr Ile Ala Ser Ile Ala Ala Lys Glu Glu Gly Val
65                  70                  75                  80

Ser Leu Glu Lys Arg Asp Val Gln Leu Gln Glu Ser Gly Pro Ser Leu
                85                  90                  95

Val Lys Pro Ser Gln Thr Leu Ser Leu Thr Cys Ser Val Thr Gly Asp
            100                 105                 110

Ser Ile Thr Ser Asp Tyr Trp Ser Trp Ile Arg Lys Phe Pro Gly Asn
            115                 120                 125

Arg Leu Glu Tyr Met Gly Tyr Val Ser Tyr Ser Gly Ser Thr Tyr Tyr
130                 135                 140

Asn Pro Ser Leu Lys Ser Arg Ile Ser Ile Thr Arg Asp Thr Ser Lys
145                 150                 155                 160

Asn Gln Tyr Tyr Leu Asp Leu Asn Ser Val Thr Thr Glu Asp Thr Ala
                165                 170                 175

Thr Tyr Tyr Cys Ala Asn Trp Asp Gly Asp Tyr Trp Gly Gln Gly Thr
            180                 185                 190

Leu Val Thr Val Ser Ser Ala Ser Thr Lys Gly Pro Ser Val Phe Pro
            195                 200                 205

Leu Ala Pro Ser Ser Lys Ser Thr Ser Gly Gly Thr Ala Ala Leu Gly
210                 215                 220

Cys Leu Val Lys Asp Tyr Phe Pro Glu Pro Val Thr Val Ser Trp Asn
225                 230                 235                 240

Ser Gly Ala Leu Thr Ser Gly Val His Thr Phe Pro Ala Val Leu Gln
                245                 250                 255

Ser Ser Gly Leu Tyr Ser Leu Ser Ser Val Val Thr Val Pro Ser Ser
            260                 265                 270

Ser Leu Gly Thr Gln Thr Tyr Ile Cys Asn Val Asn His Lys Pro Ser
            275                 280                 285

Asn Thr Lys Val Asp Lys Arg Val Glu Pro Lys Ser Cys Asp Lys
290                 295                 300

<210> SEQ ID NO 30
<211> LENGTH: 299
<212> TYPE: PRT
<213> ORGANISM: artificial
<220> FEATURE:
<223> OTHER INFORMATION: Synthetic Construct

<400> SEQUENCE: 30

Met Arg Phe Pro Ser Ile Phe Thr Ala Val Leu Phe Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Asp Ile Val Leu Thr Gln Ser Pro Ala Thr Leu
                85                  90                  95

Ser Val Thr Pro Gly Asn Ser Val Ser Leu Ser Cys Arg Ala Ser Gln
            100                 105                 110

Ser Ile Gly Asn Asn Leu His Trp Tyr Gln Lys Ser His Glu Ser
            115                 120                 125

Pro Arg Leu Leu Ile Lys Tyr Ala Ser Gln Ser Ile Ser Gly Ile Pro
        130                 135                 140

Ser Arg Phe Ser Gly Ser Gly Ser Gly Thr Asp Phe Thr Leu Ser Ile
145                 150                 155                 160

Asn Ser Val Glu Thr Glu Asp Phe Gly Met Tyr Phe Cys Gln Gln Ser
                165                 170                 175

Asn Ser Trp Pro Tyr Thr Phe Gly Gly Gly Thr Lys Leu Glu Ile Lys
            180                 185                 190

Arg Thr Val Ala Ala Pro Ser Val Phe Ile Phe Pro Pro Ser Asp Glu
        195                 200                 205

Gln Leu Lys Ser Gly Thr Ala Ser Val Val Cys Leu Leu Asn Asn Phe
    210                 215                 220

Tyr Pro Arg Glu Ala Lys Val Gln Trp Lys Val Asp Asn Ala Leu Gln
225                 230                 235                 240

Ser Gly Asn Ser Gln Glu Ser Val Thr Glu Gln Asp Ser Lys Asp Ser
                245                 250                 255

Thr Tyr Ser Leu Ser Ser Thr Leu Thr Leu Ser Lys Ala Asp Tyr Glu
            260                 265                 270

Lys His Lys Val Tyr Ala Cys Glu Val Thr His Gln Gly Leu Ser Ser
        275                 280                 285

Pro Val Thr Lys Ser Phe Asn Arg Gly Glu Cys
    290                 295

<210> SEQ ID NO 31
<211> LENGTH: 915
<212> TYPE: DNA
<213> ORGANISM: artificial
<220> FEATURE:
<223> OTHER INFORMATION: Synthetic Construct

<400> SEQUENCE: 31
atgagattcc catctatttt caccgctgtc ttgttcgctg cctcctctgc attggctgcc      60
cctgttaaca ctaccactga agacgagact gctcaaattc cagctgaagc agttatcggt     120
tactctgacc ttgagggtga tttcgacgtc gctgttttgc ctttctctaa ctccactaac     180
aacggtttgt tgttcattaa caccactatc gcttccattg ctgctaagga agagggtgtc     240
tctctcgaga gagagacgt tcaattgcaa gaatctggtc catccttggt taagccatcc      300
cagactttgt ccttgacttg ttccgttact ggtgactcca tcacttctga ctactggtcc     360
tggatcagaa agttcccagg taacagattg gagtacatgg gttacgtttc ttactccggt     420
tccacttact acaacccatc cttgaagtcc agaatctcca tcactagaga cacttccaag     480
aaccagtact acttggactt gaactccgtt actactgagg acactgctac ttactactgt     540
gctaactggg acggtgacta ttggggtcaa ggtactttgg ttactgtttc ctccgcttcc     600
actaagggtc catctgtttt tccattggct ccatcctcca gtctacttc aggtggtact      660

```
gctgctttgg gttgtttggt taaggactac ttcccagagc cagttactgt ttcttggaac    720
tccggtgctt tgacttccgg tgttcacact ttcccagctg tcttgcaatc ctccggtctg    780
tactccttgt cctccgttgt tactgttcct tcttcctcct tgggtactca aacttacatc    840
tgtaacgtta accacaagcc atccaacact aaggttgaca agagagttga gccaaagtcc    900
tgtgacaagt aatag                                                     915

<210> SEQ ID NO 32
<211> LENGTH: 903
<212> TYPE: DNA
<213> ORGANISM: artificial
<220> FEATURE:
<223> OTHER INFORMATION: Synthetic Construct

<400> SEQUENCE: 32
atgagattcc catctatttt caccgctgtc ttgttcgctg cctcctctgc attggctgcc     60
cctgttaaca ctaccactga agacgagact gctcaaattc cagctgaagc agttatcggt    120
tactctgacc ttgagggtga tttcgacgtc gctgttttgc ctttctctaa ctccactaac    180
aacggtttgt tgttcattaa caccactatc gcttccattg ctgctaagga agagggtgtc    240
tctctcgaga agagagacat cgttttgact caatccccag ctactttgtc cgttactcca    300
ggtaactccg tttccttgtc ctgtagagct tcccagtcca tcggtaacaa cttgcactgg    360
tatcagcaga agtctcacga gtccccaaga ctgttgatca agtacgcttc ccaatccatc    420
tccggtatcc catctagatt ctctggttct ggttccggta ctgacttcac tttgtccatc    480
aactccgttg agactgagga cttcggtatg tacttctgtc agcaatccaa ctcctggcca    540
tacacttttg gtggtggtac taagttggag atcaagagaa ctgttgctgc tccatccgtt    600
ttcatcttcc caccatctga cgagcagttg aagtctggta ctgcttccgt tgtttgtttg    660
ttgaacaact ctacccaag agaagctaag gttcagtgga aggttgacaa cgccttgcaa    720
tccggtaact cccaagagtc cgttactgaa caagactcca aggactctac ttactccttg    780
tcctccactt tgactttgtc caaggctgac tacgagaagc acaaggttta cgcttgtgag    840
gttactcacc agggtttgtc ctccccagtt actaagtcct caacagagg tgagtgttaa    900 tag                                                                  903

<210> SEQ ID NO 33
<211> LENGTH: 33
<212> TYPE: DNA
<213> ORGANISM: artificial
<220> FEATURE:
<223> OTHER INFORMATION: Synthetic Construct

<400> SEQUENCE: 33
actacctgca ggcgaaacga tgagattccc atc                                  33

<210> SEQ ID NO 34
<211> LENGTH: 44
<212> TYPE: DNA
<213> ORGANISM: artificial
<220> FEATURE:
<223> OTHER INFORMATION: Synthetic Construct

<400> SEQUENCE: 34
tcatggccga ggcggcccta ttacttgtca caggactttg gctc                      44

<210> SEQ ID NO 35
```

```
<211> LENGTH: 39
<212> TYPE: DNA
<213> ORGANISM: artificial
<220> FEATURE:
<223> OTHER INFORMATION: Synthetic Construct

<400> SEQUENCE: 35
ctatggccga ggcggcccta ttaacactca cctctgttg                        39

<210> SEQ ID NO 36
<211> LENGTH: 39
<212> TYPE: DNA
<213> ORGANISM: artificial
<220> FEATURE:
<223> OTHER INFORMATION: Synthetic Construct

<400> SEQUENCE: 36
tatcggccga ggcggcccta ttacttacct ggggacaag                        39

<210> SEQ ID NO 37
<211> LENGTH: 39
<212> TYPE: DNA
<213> ORGANISM: artificial
<220> FEATURE:
<223> OTHER INFORMATION: Synthetic Construct

<400> SEQUENCE: 37
ctatggccga ggcggcccta ttaacactca cctctgttg                        39

<210> SEQ ID NO 38
<211> LENGTH: 32
<212> TYPE: DNA
<213> ORGANISM: artificial
<220> FEATURE:
<223> OTHER INFORMATION: Synthetic Construct

<400> SEQUENCE: 38
cttgcctgca ggatgctaac ggccagttgg tc                               32

<210> SEQ ID NO 39
<211> LENGTH: 40
<212> TYPE: DNA
<213> ORGANISM: artificial
<220> FEATURE:
<223> OTHER INFORMATION: Synthetic Construct

<400> SEQUENCE: 39
gatcggccga ggcggcctca gcagtattcc caccagaatc                       40

<210> SEQ ID NO 40
<211> LENGTH: 38
<212> TYPE: DNA
<213> ORGANISM: artificial
<220> FEATURE:
<223> OTHER INFORMATION: Synthetic Construct

<400> SEQUENCE: 40
cttgcctgca ggatgtcagt tcatttcgtt atagcagc                         38

<210> SEQ ID NO 41
<211> LENGTH: 52
<212> TYPE: DNA
<213> ORGANISM: artificial
<220> FEATURE:
<223> OTHER INFORMATION: Synthetic Construct

<400> SEQUENCE: 41
```
gatcggccga ggcggcctca tataaaaggt ttatcataat tctcatcctc ag          52

<210> SEQ ID NO 42
<211> LENGTH: 43
<212> TYPE: DNA
<213> ORGANISM: artificial
<220> FEATURE:
<223> OTHER INFORMATION: Synthetic Construct

<400> SEQUENCE: 42
gaaacctgca ggatgtctga atttgttgct aaaattaaca ttc                   43

<210> SEQ ID NO 43
<211> LENGTH: 36
<212> TYPE: DNA
<213> ORGANISM: artificial
<220> FEATURE:
<223> OTHER INFORMATION: Synthetic Construct

<400> SEQUENCE: 43
gatcggccga ggcggcctta ggcggttgga acgttc                           36

<210> SEQ ID NO 44
<211> LENGTH: 39
<212> TYPE: DNA
<213> ORGANISM: artificial
<220> FEATURE:
<223> OTHER INFORMATION: Synthetic Construct

<400> SEQUENCE: 44
gaaacctgca ggatgtctca tctattactg cgtgacagc                        39

<210> SEQ ID NO 45
<211> LENGTH: 37
<212> TYPE: DNA
<213> ORGANISM: artificial
<220> FEATURE:
<223> OTHER INFORMATION: Synthetic Construct

<400> SEQUENCE: 45
gatcggccga ggcggcctca tggcccggca tatctag                          37

<210> SEQ ID NO 46
<211> LENGTH: 43
<212> TYPE: DNA
<213> ORGANISM: artificial
<220> FEATURE:
<223> OTHER INFORMATION: Synthetic Construct

<400> SEQUENCE: 46
gacacctgca ggatgtctga atcctccagt atctctctag ttg                   43

<210> SEQ ID NO 47
<211> LENGTH: 42
<212> TYPE: DNA
<213> ORGANISM: artificial
<220> FEATURE:
<223> OTHER INFORMATION: Synthetic Construct

<400> SEQUENCE: 47
gatcggccga ggcggcccta gatacatccc aaaagtgcac cg                    42

<210> SEQ ID NO 48
<211> LENGTH: 34
<212> TYPE: DNA

```
<213> ORGANISM: artificial
<220> FEATURE:
<223> OTHER INFORMATION: Synthetic Construct

<400> SEQUENCE: 48
gatacctgca ggatgatcct gggttcagtt tggg                              34

<210> SEQ ID NO 49
<211> LENGTH: 43
<212> TYPE: DNA
<213> ORGANISM: artificial
<220> FEATURE:
<223> OTHER INFORMATION: Synthetic Construct

<400> SEQUENCE: 49
gatcggccga ggcggcccta aaagtttgct gcagcatttg aag                    43

<210> SEQ ID NO 50
<211> LENGTH: 37
<212> TYPE: DNA
<213> ORGANISM: artificial
<220> FEATURE:
<223> OTHER INFORMATION: Synthetic Construct

<400> SEQUENCE: 50
cttgcctgca ggatgggttg ctttagattt tgtctgg                           37

<210> SEQ ID NO 51
<211> LENGTH: 42
<212> TYPE: DNA
<213> ORGANISM: artificial
<220> FEATURE:
<223> OTHER INFORMATION: Synthetic Construct

<400> SEQUENCE: 51
gatcggccga ggcggcccta tttgtatacg tgctgtggag cc                     42

<210> SEQ ID NO 52
<211> LENGTH: 42
<212> TYPE: DNA
<213> ORGANISM: artificial
<220> FEATURE:
<223> OTHER INFORMATION: Synthetic Construct

<400> SEQUENCE: 52
cttgcctgca ggatgttaaa caagctgttc attgcaatac tc                     42

<210> SEQ ID NO 53
<211> LENGTH: 41
<212> TYPE: DNA
<213> ORGANISM: artificial
<220> FEATURE:
<223> OTHER INFORMATION: Synthetic Construct

<400> SEQUENCE: 53
gatcggccga ggcggcctta gctggcaagg gtaattgtct c                      41

<210> SEQ ID NO 54
<211> LENGTH: 33
<212> TYPE: DNA
<213> ORGANISM: artificial
<220> FEATURE:
<223> OTHER INFORMATION: Synthetic Construct

<400> SEQUENCE: 54
gacacctgca ggatggctcc tcaaacacca agg                               33
```

<210> SEQ ID NO 55
<211> LENGTH: 44
<212> TYPE: DNA
<213> ORGANISM: artificial
<220> FEATURE:
<223> OTHER INFORMATION: Synthetic Construct

<400> SEQUENCE: 55
gatcggccga ggcggcctca aaaaaacaat ctcaaaatct ccag            44

<210> SEQ ID NO 56
<211> LENGTH: 33
<212> TYPE: DNA
<213> ORGANISM: artificial
<220> FEATURE:
<223> OTHER INFORMATION: Synthetic Construct

<400> SEQUENCE: 56
gtaccctgca ggatgaccaa ggaaaatgaa gcc                         33

<210> SEQ ID NO 57
<211> LENGTH: 41
<212> TYPE: DNA
<213> ORGANISM: artificial
<220> FEATURE:
<223> OTHER INFORMATION: Synthetic Construct

<400> SEQUENCE: 57
gatcggccga ggcggcctta tttttctcc aattcagcca g                 41

<210> SEQ ID NO 58
<211> LENGTH: 40
<212> TYPE: DNA
<213> ORGANISM: artificial
<220> FEATURE:
<223> OTHER INFORMATION: Synthetic Construct

<400> SEQUENCE: 58
gaaacctgca ggatgctgtt gtcacatacc atgatacttc                  40

<210> SEQ ID NO 59
<211> LENGTH: 43
<212> TYPE: DNA
<213> ORGANISM: artificial
<220> FEATURE:
<223> OTHER INFORMATION: Synthetic Construct

<400> SEQUENCE: 59
gatcggccga ggcggcctta agattgcttc tttttgagat tgg              43

<210> SEQ ID NO 60
<211> LENGTH: 38
<212> TYPE: DNA
<213> ORGANISM: artificial
<220> FEATURE:
<223> OTHER INFORMATION: Synthetic Construct

<400> SEQUENCE: 60
gaaacctgca ggatgacgga ctatgtcact tctaagcg                    38

<210> SEQ ID NO 61
<211> LENGTH: 37
<212> TYPE: DNA
<213> ORGANISM: artificial
<220> FEATURE:

<223> OTHER INFORMATION: Synthetic Construct

<400> SEQUENCE: 61
gatcggccga ggcggcctca taatctccct ccagggg                    37

<210> SEQ ID NO 62
<211> LENGTH: 33
<212> TYPE: DNA
<213> ORGANISM: artificial
<220> FEATURE:
<223> OTHER INFORMATION: Synthetic Construct

<400> SEQUENCE: 62
gaaacctgca ggatgtcgtc tgatgctgtg gag                        33

<210> SEQ ID NO 63
<211> LENGTH: 46
<212> TYPE: DNA
<213> ORGANISM: artificial
<220> FEATURE:
<223> OTHER INFORMATION: Synthetic Construct

<400> SEQUENCE: 63
gatcggccga ggcggcctca aataatgcta catttgcgtt tctttc          46

<210> SEQ ID NO 64
<211> LENGTH: 39
<212> TYPE: DNA
<213> ORGANISM: artificial
<220> FEATURE:
<223> OTHER INFORMATION: Synthetic Construct

<400> SEQUENCE: 64
cttgcctgca ggatgtctta tacgtcggac aacaaagag                  39

<210> SEQ ID NO 65
<211> LENGTH: 42
<212> TYPE: DNA
<213> ORGANISM: artificial
<220> FEATURE:
<223> OTHER INFORMATION: Synthetic Construct

<400> SEQUENCE: 65
gatcggccga ggcggcctta cgtgtatccg cttcctctgt ac              42

<210> SEQ ID NO 66
<211> LENGTH: 44
<212> TYPE: DNA
<213> ORGANISM: artificial
<220> FEATURE:
<223> OTHER INFORMATION: Synthetic Construct

<400> SEQUENCE: 66
gatacctgca ggatgaactt gtacctaatt acattactat tcgc            44

<210> SEQ ID NO 67
<211> LENGTH: 44
<212> TYPE: DNA
<213> ORGANISM: artificial
<220> FEATURE:
<223> OTHER INFORMATION: Synthetic Construct

<400> SEQUENCE: 67
gatcggccga ggcggcctta gaacccacat tgatttggat actg            44

```
<210> SEQ ID NO 68
<211> LENGTH: 37
<212> TYPE: DNA
<213> ORGANISM: artificial
<220> FEATURE:
<223> OTHER INFORMATION: Synthetic Construct

<400> SEQUENCE: 68
gaaacctgca ggatgtcgtt atcaaccttt ctaggcg                              37

<210> SEQ ID NO 69
<211> LENGTH: 47
<212> TYPE: DNA
<213> ORGANISM: artificial
<220> FEATURE:
<223> OTHER INFORMATION: Synthetic Construct

<400> SEQUENCE: 69
gatcggccga ggcggcctca gactctactc atcattttgt cttcctc                   47

<210> SEQ ID NO 70
<211> LENGTH: 44
<212> TYPE: DNA
<213> ORGANISM: artificial
<220> FEATURE:
<223> OTHER INFORMATION: Synthetic Construct

<400> SEQUENCE: 70
gaaacctgca ggatgatgta caggaactta ataattgcta ctgc                      44

<210> SEQ ID NO 71
<211> LENGTH: 48
<212> TYPE: DNA
<213> ORGANISM: artificial
<220> FEATURE:
<223> OTHER INFORMATION: Synthetic Construct

<400> SEQUENCE: 71
gatcggccga ggcggcccta acactctatg aggtctacaa tgtccaac                  48

<210> SEQ ID NO 72
<211> LENGTH: 37
<212> TYPE: DNA
<213> ORGANISM: artificial
<220> FEATURE:
<223> OTHER INFORMATION: Synthetic Construct

<400> SEQUENCE: 72
catgcctgca ggatgtctac agcaattcca ggaggac                              37

<210> SEQ ID NO 73
<211> LENGTH: 46
<212> TYPE: DNA
<213> ORGANISM: artificial
<220> FEATURE:
<223> OTHER INFORMATION: Synthetic Construct

<400> SEQUENCE: 73
gatcggccga ggcggcctta gttgatcaac tttcctgtca gcttag                    46

<210> SEQ ID NO 74
<211> LENGTH: 39
<212> TYPE: DNA
<213> ORGANISM: artificial
<220> FEATURE:
<223> OTHER INFORMATION: Synthetic Construct
```

<400> SEQUENCE: 74
gacacctgca ggatgagtgg tgaccataag agctttacg                    39

<210> SEQ ID NO 75
<211> LENGTH: 44
<212> TYPE: DNA
<213> ORGANISM: artificial
<220> FEATURE:
<223> OTHER INFORMATION: Synthetic Construct

<400> SEQUENCE: 75
gatcggccga ggcggcctta ctgtgtacca taccgatcca atcc              44

<210> SEQ ID NO 76
<211> LENGTH: 41
<212> TYPE: DNA
<213> ORGANISM: artificial
<220> FEATURE:
<223> OTHER INFORMATION: Synthetic Construct

<400> SEQUENCE: 76
cttgcctgca ggatgactaa ctggaaagcg atattgactc c                 41

<210> SEQ ID NO 77
<211> LENGTH: 49
<212> TYPE: DNA
<213> ORGANISM: artificial
<220> FEATURE:
<223> OTHER INFORMATION: Synthetic Construct

<400> SEQUENCE: 77
gatcggccga ggcggcctta gttctcttct tcaccttgaa attttaggc         49

<210> SEQ ID NO 78
<211> LENGTH: 37
<212> TYPE: DNA
<213> ORGANISM: artificial
<220> FEATURE:
<223> OTHER INFORMATION: Synthetic Construct

<400> SEQUENCE: 78
gcaacctgca ggatgtctta tcgccctcag tttcaac                      37

<210> SEQ ID NO 79
<211> LENGTH: 51
<212> TYPE: DNA
<213> ORGANISM: artificial
<220> FEATURE:
<223> OTHER INFORMATION: Synthetic Construct

<400> SEQUENCE: 79
gatcggccga ggcggcctca atagatcttt ttcttttcat caaaactcaa c      51

<210> SEQ ID NO 80
<211> LENGTH: 36
<212> TYPE: DNA
<213> ORGANISM: artificial
<220> FEATURE:
<223> OTHER INFORMATION: Synthetic Construct

<400> SEQUENCE: 80
gatacctgca ggatggtggt gcacaaccct aataac                       36

<210> SEQ ID NO 81
<211> LENGTH: 49

```
<212> TYPE: DNA
<213> ORGANISM: artificial
<220> FEATURE:
<223> OTHER INFORMATION: Synthetic Construct

<400> SEQUENCE: 81
gatcggccga ggcggcccta ggtactatgc tgaacatcct gagtatgag          49

<210> SEQ ID NO 82
<211> LENGTH: 41
<212> TYPE: DNA
<213> ORGANISM: artificial
<220> FEATURE:
<223> OTHER INFORMATION: Synthetic Construct

<400> SEQUENCE: 82
gaaacctgca ggatgagatt ttctaacgtc gttttaactg c                  41

<210> SEQ ID NO 83
<211> LENGTH: 42
<212> TYPE: DNA
<213> ORGANISM: artificial
<220> FEATURE:
<223> OTHER INFORMATION: Synthetic Construct

<400> SEQUENCE: 83
gatcggccga ggcggcctta caaggcaaag actccgaaag tg                 42

<210> SEQ ID NO 84
<211> LENGTH: 38
<212> TYPE: DNA
<213> ORGANISM: artificial
<220> FEATURE:
<223> OTHER INFORMATION: Synthetic Construct

<400> SEQUENCE: 84
gacacctgca ggatgactgt gcctgatctg aaagaaac                      38

<210> SEQ ID NO 85
<211> LENGTH: 33
<212> TYPE: DNA
<213> ORGANISM: artificial
<220> FEATURE:
<223> OTHER INFORMATION: Synthetic Construct

<400> SEQUENCE: 85
gatcggccga ggcggcctca ggccagcgca acg                           33

<210> SEQ ID NO 86
<211> LENGTH: 46
<212> TYPE: DNA
<213> ORGANISM: artificial
<220> FEATURE:
<223> OTHER INFORMATION: Synthetic Construct

<400> SEQUENCE: 86
cttgcctgca ggatgaagat atggctggta cttcttttag tttttg             46

<210> SEQ ID NO 87
<211> LENGTH: 43
<212> TYPE: DNA
<213> ORGANISM: artificial
<220> FEATURE:
<223> OTHER INFORMATION: Synthetic Construct

<400> SEQUENCE: 87
```
gatcggccga ggcggcctca caattcgtct ctaatttgtt gcg          43

<210> SEQ ID NO 88
<211> LENGTH: 31
<212> TYPE: DNA
<213> ORGANISM: artificial
<220> FEATURE:
<223> OTHER INFORMATION: Synthetic Construct

<400> SEQUENCE: 88
cttgcctgca ggatggagca ggttccagtc g                        31

<210> SEQ ID NO 89
<211> LENGTH: 47
<212> TYPE: DNA
<213> ORGANISM: artificial
<220> FEATURE:
<223> OTHER INFORMATION: Synthetic Construct

<400> SEQUENCE: 89
gatcggccga ggcggcctta ttcatcataa acttcttcta tggtggc      47

<210> SEQ ID NO 90
<211> LENGTH: 38
<212> TYPE: DNA
<213> ORGANISM: artificial
<220> FEATURE:
<223> OTHER INFORMATION: Synthetic Construct

<400> SEQUENCE: 90
cttgcctgca ggatggatcc ttttcaatt cttctcac                  38

<210> SEQ ID NO 91
<211> LENGTH: 47
<212> TYPE: DNA
<213> ORGANISM: artificial
<220> FEATURE:
<223> OTHER INFORMATION: Synthetic Construct

<400> SEQUENCE: 91
gatcggccga ggcggcccta ctttggagac agatcttcca ccttaac      47

<210> SEQ ID NO 92
<211> LENGTH: 37
<212> TYPE: DNA
<213> ORGANISM: artificial
<220> FEATURE:
<223> OTHER INFORMATION: Synthetic Construct

<400> SEQUENCE: 92
gaaacctgca ggatgaccag tcaaggattt ttggatc                  37

<210> SEQ ID NO 93
<211> LENGTH: 49
<212> TYPE: DNA
<213> ORGANISM: artificial
<220> FEATURE:
<223> OTHER INFORMATION: Synthetic Construct

<400> SEQUENCE: 93
gatcggccga ggcggcccta tatgctatca accatctcca tcaaataac    49

<210> SEQ ID NO 94
<211> LENGTH: 36
<212> TYPE: DNA
<213> ORGANISM: artificial

```
<220> FEATURE:
<223> OTHER INFORMATION: Synthetic Construct

<400> SEQUENCE: 94
gacacctgca ggatgactcc ccgttctcat attttc                                    36

<210> SEQ ID NO 95
<211> LENGTH: 50
<212> TYPE: DNA
<213> ORGANISM: artificial
<220> FEATURE:
<223> OTHER INFORMATION: Synthetic Construct

<400> SEQUENCE: 95
gatcggccga ggcggcccta ctcaaagaac ttagacaaag cagctttctc                     50

<210> SEQ ID NO 96
<211> LENGTH: 29
<212> TYPE: DNA
<213> ORGANISM: artificial
<220> FEATURE:
<223> OTHER INFORMATION: Synthetic Construct

<400> SEQUENCE: 96
gatccctgca ggatggcaga agaagaacc                                            29

<210> SEQ ID NO 97
<211> LENGTH: 54
<212> TYPE: DNA
<213> ORGANISM: artificial
<220> FEATURE:
<223> OTHER INFORMATION: Synthetic Construct

<400> SEQUENCE: 97
gatcggccga ggcggcccta attagtaata cttgcttcta tttcctggta caac               54

<210> SEQ ID NO 98
<211> LENGTH: 40
<212> TYPE: DNA
<213> ORGANISM: artificial
<220> FEATURE:
<223> OTHER INFORMATION: Synthetic Construct

<400> SEQUENCE: 98
gaaccctgca ggatgatttt gagcaagctg tcgtttagac                                40

<210> SEQ ID NO 99
<211> LENGTH: 51
<212> TYPE: DNA
<213> ORGANISM: artificial
<220> FEATURE:
<223> OTHER INFORMATION: Synthetic Construct

<400> SEQUENCE: 99
gatcggccga ggcggcctta tttattaaca atgacatcat cttcaaactc g                   51

<210> SEQ ID NO 100
<211> LENGTH: 30
<212> TYPE: DNA
<213> ORGANISM: artificial
<220> FEATURE:
<223> OTHER INFORMATION: Synthetic Construct

<400> SEQUENCE: 100
cttgcctgca ggatgggtgc cattggaatg                                           30
```

<210> SEQ ID NO 101
<211> LENGTH: 44
<212> TYPE: DNA
<213> ORGANISM: artificial
<220> FEATURE:
<223> OTHER INFORMATION: Synthetic Construct

<400> SEQUENCE: 101
gatcggccga ggcggcccta ttgcagaaca ttcgatatcc aatc          44

<210> SEQ ID NO 102
<211> LENGTH: 36
<212> TYPE: DNA
<213> ORGANISM: artificial
<220> FEATURE:
<223> OTHER INFORMATION: Synthetic Construct

<400> SEQUENCE: 102
gatacctgca ggatgctacc attttcgtac gacgtg                  36

<210> SEQ ID NO 103
<211> LENGTH: 45
<212> TYPE: DNA
<213> ORGANISM: artificial
<220> FEATURE:
<223> OTHER INFORMATION: Synthetic Construct

<400> SEQUENCE: 103
gatcggccga ggcggcccta taactctcca ttctcctcgt cgatc         45

<210> SEQ ID NO 104
<211> LENGTH: 47
<212> TYPE: DNA
<213> ORGANISM: artificial
<220> FEATURE:
<223> OTHER INFORMATION: Synthetic Construct

<400> SEQUENCE: 104
gatccctgca ggatgaaaat attaagtgca ttgcttcttc ttttac        47

<210> SEQ ID NO 105
<211> LENGTH: 44
<212> TYPE: DNA
<213> ORGANISM: artificial
<220> FEATURE:
<223> OTHER INFORMATION: Synthetic Construct

<400> SEQUENCE: 105
gatcggccga ggcggcctta tagctcttgg tgtaataact gggg          44

<210> SEQ ID NO 106
<211> LENGTH: 42
<212> TYPE: DNA
<213> ORGANISM: artificial
<220> FEATURE:
<223> OTHER INFORMATION: Synthetic Construct

<400> SEQUENCE: 106
cttgcctgca ggatgtctaa accctacaag ctgataggtg ag            42

<210> SEQ ID NO 107
<211> LENGTH: 45
<212> TYPE: DNA
<213> ORGANISM: artificial
<220> FEATURE:
<223> OTHER INFORMATION: Synthetic Construct

```
<400> SEQUENCE: 107
gatcggccga ggcggcctta atcttctcca gcaggtatct catcc            45

<210> SEQ ID NO 108
<211> LENGTH: 45
<212> TYPE: DNA
<213> ORGANISM: artificial
<220> FEATURE:
<223> OTHER INFORMATION: Synthetic Construct

<400> SEQUENCE: 108
cttgcctgca ggatgaatca attttctcta gcttcacaag taaac            45

<210> SEQ ID NO 109
<211> LENGTH: 41
<212> TYPE: DNA
<213> ORGANISM: artificial
<220> FEATURE:
<223> OTHER INFORMATION: Synthetic Construct

<400> SEQUENCE: 109
gatcggccga ggcggcccta ctcggttaat ggtccgagtg c                 41

<210> SEQ ID NO 110
<211> LENGTH: 42
<212> TYPE: DNA
<213> ORGANISM: artificial
<220> FEATURE:
<223> OTHER INFORMATION: Synthetic Construct

<400> SEQUENCE: 110
gacacctgca ggatgagtta taggaaagac aacaaacaaa ag               42

<210> SEQ ID NO 111
<211> LENGTH: 39
<212> TYPE: DNA
<213> ORGANISM: artificial
<220> FEATURE:
<223> OTHER INFORMATION: Synthetic Construct

<400> SEQUENCE: 111
gatcggccga ggcggcctta gaaggcagct tcatcatcg                   39

<210> SEQ ID NO 112
<211> LENGTH: 40
<212> TYPE: DNA
<213> ORGANISM: artificial
<220> FEATURE:
<223> OTHER INFORMATION: Synthetic Construct

<400> SEQUENCE: 112
cttgcctgca ggatgagcag cttcagagtt ctagacttgg                  40

<210> SEQ ID NO 113
<211> LENGTH: 35
<212> TYPE: DNA
<213> ORGANISM: artificial
<220> FEATURE:
<223> OTHER INFORMATION: Synthetic Construct

<400> SEQUENCE: 113
gatcggccga ggcggcctta cagatcaacg aatcc                       35

<210> SEQ ID NO 114
```

```
<211> LENGTH: 44
<212> TYPE: DNA
<213> ORGANISM: artificial
<220> FEATURE:
<223> OTHER INFORMATION: Synthetic Construct

<400> SEQUENCE: 114
gatacctgca ggatgaacat ctttagaatc ctaggtaagt ttcc              44

<210> SEQ ID NO 115
<211> LENGTH: 39
<212> TYPE: DNA
<213> ORGANISM: artificial
<220> FEATURE:
<223> OTHER INFORMATION: Synthetic Construct

<400> SEQUENCE: 115
gatcggccga ggcggcctca ttctggcagc ttgaatttc                    39

<210> SEQ ID NO 116
<211> LENGTH: 45
<212> TYPE: DNA
<213> ORGANISM: artificial
<220> FEATURE:
<223> OTHER INFORMATION: Synthetic Construct

<400> SEQUENCE: 116
cttgcctgca ggatgtccac aactactaag aaaaacaaga acagg             45

<210> SEQ ID NO 117
<211> LENGTH: 39
<212> TYPE: DNA
<213> ORGANISM: artificial
<220> FEATURE:
<223> OTHER INFORMATION: Synthetic Construct

<400> SEQUENCE: 117
gatcggccga ggcggcctta ccatgcaccc tttcctctc                    39

<210> SEQ ID NO 118
<211> LENGTH: 40
<212> TYPE: DNA
<213> ORGANISM: artificial
<220> FEATURE:
<223> OTHER INFORMATION: Synthetic Construct

<400> SEQUENCE: 118
cttgcctgca ggatgtcaga ggagtaagaa ccacaaacag                   40

<210> SEQ ID NO 119
<211> LENGTH: 45
<212> TYPE: DNA
<213> ORGANISM: artificial
<220> FEATURE:
<223> OTHER INFORMATION: Synthetic Construct

<400> SEQUENCE: 119
gatcggccga ggcggcctca atttattcta ggttttttgg ttcgg             45

<210> SEQ ID NO 120
<211> LENGTH: 31
<212> TYPE: DNA
<213> ORGANISM: artificial
<220> FEATURE:
<223> OTHER INFORMATION: Synthetic Construct

<400> SEQUENCE: 120
```

```
gtaccctgca ggatgatggc aagtccaacc g                                          31
```

<210> SEQ ID NO 121
<211> LENGTH: 34
<212> TYPE: DNA
<213> ORGANISM: artificial
<220> FEATURE:
<223> OTHER INFORMATION: Synthetic Construct

<400> SEQUENCE: 121

```
gatcggccga ggcggcccgc aacaacgctg gttg                                       34
```

<210> SEQ ID NO 122
<211> LENGTH: 42
<212> TYPE: DNA
<213> ORGANISM: artificial
<220> FEATURE:
<223> OTHER INFORMATION: Synthetic Construct

<400> SEQUENCE: 122

```
cttgcctgca ggatgagtaa ccagtataat ccgtatgagc ag                              42
```

<210> SEQ ID NO 123
<211> LENGTH: 40
<212> TYPE: DNA
<213> ORGANISM: artificial
<220> FEATURE:
<223> OTHER INFORMATION: Synthetic Construct

<400> SEQUENCE: 123

```
gatcggccga ggcggcccta tcttccccag tttccgacac                                 40
```

<210> SEQ ID NO 124
<211> LENGTH: 43
<212> TYPE: DNA
<213> ORGANISM: artificial
<220> FEATURE:
<223> OTHER INFORMATION: Synthetic Construct

<400> SEQUENCE: 124

```
gttacctgca ggatgtctac agagaacaaa gcagagacaa aac                             43
```

<210> SEQ ID NO 125
<211> LENGTH: 41
<212> TYPE: DNA
<213> ORGANISM: artificial
<220> FEATURE:
<223> OTHER INFORMATION: Synthetic Construct

<400> SEQUENCE: 125

```
gatcggccga ggcggcccta tttctttgct tcagcgtttg c                               41
```

<210> SEQ ID NO 126
<211> LENGTH: 44
<212> TYPE: DNA
<213> ORGANISM: artificial
<220> FEATURE:
<223> OTHER INFORMATION: Synthetic Construct

<400> SEQUENCE: 126

```
cttgcctgca ggatgttaaa cttaatatcc acaataagtg ggtg                            44
```

<210> SEQ ID NO 127
<211> LENGTH: 41
<212> TYPE: DNA

<213> ORGANISM: artificial
<220> FEATURE:
<223> OTHER INFORMATION: Synthetic Construct

<400> SEQUENCE: 127
gatcggccga ggcggcctta agcaggagca gataaccaag c                                    41

<210> SEQ ID NO 128
<211> LENGTH: 42
<212> TYPE: DNA
<213> ORGANISM: artificial
<220> FEATURE:
<223> OTHER INFORMATION: Synthetic Construct

<400> SEQUENCE: 128
cttgcctgca ggatgggtag aaggaaaata gagataaatc cg                                   42

<210> SEQ ID NO 129
<211> LENGTH: 43
<212> TYPE: DNA
<213> ORGANISM: artificial
<220> FEATURE:
<223> OTHER INFORMATION: Synthetic Construct

<400> SEQUENCE: 129
gatcggccga ggcggcctca gctcttctta gtcacactgc ttg                                  43

<210> SEQ ID NO 130
<211> LENGTH: 40
<212> TYPE: DNA
<213> ORGANISM: artificial
<220> FEATURE:
<223> OTHER INFORMATION: Synthetic Construct

<400> SEQUENCE: 130
cttgcctgca ggatgtcact tcaactgtcc attatcttcg                                      40

<210> SEQ ID NO 131
<211> LENGTH: 44
<212> TYPE: DNA
<213> ORGANISM: artificial
<220> FEATURE:
<223> OTHER INFORMATION: Synthetic Construct

<400> SEQUENCE: 131
gatcggccga ggcggcccta ctcgtccttc ttgttgctct tctc                                 44

<210> SEQ ID NO 132
<211> LENGTH: 22
<212> TYPE: DNA
<213> ORGANISM: artificial
<220> FEATURE:
<223> OTHER INFORMATION: Synthetic Construct

<400> SEQUENCE: 132
cgaacatcca tcaccaaaac ac                                                         22

<210> SEQ ID NO 133
<211> LENGTH: 37
<212> TYPE: DNA
<213> ORGANISM: artificial
<220> FEATURE:
<223> OTHER INFORMATION: Synthetic Construct

<400> SEQUENCE: 133
gttgtcgacc tgcagcgtac ggtgttgccg cgaaatg                                         37

<210> SEQ ID NO 134
<211> LENGTH: 37
<212> TYPE: DNA
<213> ORGANISM: artificial
<220> FEATURE:
<223> OTHER INFORMATION: Synthetic Construct

<400> SEQUENCE: 134
catttcgcgg caacaccgta cgctgcaggt cgacaac                37

<210> SEQ ID NO 135
<211> LENGTH: 24
<212> TYPE: DNA
<213> ORGANISM: artificial
<220> FEATURE:
<223> OTHER INFORMATION: Synthetic Construct

<400> SEQUENCE: 135
cggtgagaat ggcaaaagct tatg                             24

<210> SEQ ID NO 136
<211> LENGTH: 21
<212> TYPE: DNA
<213> ORGANISM: artificial
<220> FEATURE:
<223> OTHER INFORMATION: Synthetic Construct

<400> SEQUENCE: 136
aagcccgatg cgccagagtt g                                21

<210> SEQ ID NO 137
<211> LENGTH: 41
<212> TYPE: DNA
<213> ORGANISM: artificial
<220> FEATURE:
<223> OTHER INFORMATION: Synthetic Construct

<400> SEQUENCE: 137
cgtctcttgg gcaaattgat cagtggatct gatatcacct a          41

<210> SEQ ID NO 138
<211> LENGTH: 41
<212> TYPE: DNA
<213> ORGANISM: artificial
<220> FEATURE:
<223> OTHER INFORMATION: Synthetic Construct

<400> SEQUENCE: 138
taggtgatat cagatccact gatcaatttg cccaagagac g          41

<210> SEQ ID NO 139
<211> LENGTH: 20
<212> TYPE: DNA
<213> ORGANISM: artificial
<220> FEATURE:
<223> OTHER INFORMATION: Synthetic Construct

<400> SEQUENCE: 139
gactgttgcg attgctggtg                                  20

<210> SEQ ID NO 140
<211> LENGTH: 21
<212> TYPE: DNA
<213> ORGANISM: artificial
<220> FEATURE:

<223> OTHER INFORMATION: Synthetic Construct

<400> SEQUENCE: 140
atccaggaca cgctcatcaa g                                          21

<210> SEQ ID NO 141
<211> LENGTH: 22
<212> TYPE: DNA
<213> ORGANISM: artificial
<220> FEATURE:
<223> OTHER INFORMATION: Synthetic Construct

<400> SEQUENCE: 141
gtgtgtgctc tggaattgga tc                                         22

<210> SEQ ID NO 142
<211> LENGTH: 23
<212> TYPE: DNA
<213> ORGANISM: artificial
<220> FEATURE:
<223> OTHER INFORMATION: Synthetic Construct

<400> SEQUENCE: 142
agaggaggtt gaatgcgaag aag                                        23

<210> SEQ ID NO 143
<211> LENGTH: 49
<212> TYPE: DNA
<213> ORGANISM: artificial
<220> FEATURE:
<223> OTHER INFORMATION: Synthetic Construct

<400> SEQUENCE: 143
gttgtcgacc tgcagcgtac ttctggtgag cttatatggc agtagttac             49

<210> SEQ ID NO 144
<211> LENGTH: 49
<212> TYPE: DNA
<213> ORGANISM: artificial
<220> FEATURE:
<223> OTHER INFORMATION: Synthetic Construct

<400> SEQUENCE: 144
gtaactactg ccatataagc tcaccagaag tacgctgcag gtcgacaac             49

<210> SEQ ID NO 145
<211> LENGTH: 24
<212> TYPE: DNA
<213> ORGANISM: artificial
<220> FEATURE:
<223> OTHER INFORMATION: Synthetic Construct

<400> SEQUENCE: 145
cggtgagaat ggcaaaagct tatg                                       24

<210> SEQ ID NO 146
<211> LENGTH: 21
<212> TYPE: DNA
<213> ORGANISM: artificial
<220> FEATURE:
<223> OTHER INFORMATION: Synthetic Construct

<400> SEQUENCE: 146
aagcccgatg cgccagagtt g                                          21

```
<210> SEQ ID NO 147
<211> LENGTH: 39
<212> TYPE: DNA
<213> ORGANISM: artificial
<220> FEATURE:
<223> OTHER INFORMATION: Synthetic Construct

<400> SEQUENCE: 147
ctcgggatca ccaagcacaa gtggatctga tatcaccta                              39

<210> SEQ ID NO 148
<211> LENGTH: 39
<212> TYPE: DNA
<213> ORGANISM: artificial
<220> FEATURE:
<223> OTHER INFORMATION: Synthetic Construct

<400> SEQUENCE: 148
taggtgatat cagatccact tgtgcttggt gatcccgag                              39

<210> SEQ ID NO 149
<211> LENGTH: 23
<212> TYPE: DNA
<213> ORGANISM: artificial
<220> FEATURE:
<223> OTHER INFORMATION: Synthetic Construct

<400> SEQUENCE: 149
tcaaagtatg ctgggaagaa tgg                                              23

<210> SEQ ID NO 150
<211> LENGTH: 18
<212> TYPE: DNA
<213> ORGANISM: artificial
<220> FEATURE:
<223> OTHER INFORMATION: Synthetic Construct

<400> SEQUENCE: 150
tggattgtct cggaggcg                                                    18

<210> SEQ ID NO 151
<211> LENGTH: 26
<212> TYPE: DNA
<213> ORGANISM: artificial
<220> FEATURE:
<223> OTHER INFORMATION: Synthetic Construct

<400> SEQUENCE: 151
tactatgact atgggagacc tgggtg                                           26

<210> SEQ ID NO 152
<211> LENGTH: 19
<212> TYPE: DNA
<213> ORGANISM: artificial
<220> FEATURE:
<223> OTHER INFORMATION: Synthetic Construct

<400> SEQUENCE: 152
tgaagcatcc cacccactg                                                   19

<210> SEQ ID NO 153
<211> LENGTH: 44
<212> TYPE: DNA
<213> ORGANISM: artificial
<220> FEATURE:
<223> OTHER INFORMATION: Synthetic Construct
```

```
<400> SEQUENCE: 153
gttgtcgacc tgcagcgtac ccttcgcaga ctgtaattat tggc         44

<210> SEQ ID NO 154
<211> LENGTH: 44
<212> TYPE: DNA
<213> ORGANISM: artificial
<220> FEATURE:
<223> OTHER INFORMATION: Synthetic Construct

<400> SEQUENCE: 154
gccaataatt acagtctgcg aagggtacgc tgcaggtcga caac         44

<210> SEQ ID NO 155
<211> LENGTH: 24
<212> TYPE: DNA
<213> ORGANISM: artificial
<220> FEATURE:
<223> OTHER INFORMATION: Synthetic Construct

<400> SEQUENCE: 155
cggtgagaat ggcaaaagct tatg                              24

<210> SEQ ID NO 156
<211> LENGTH: 21
<212> TYPE: DNA
<213> ORGANISM: artificial
<220> FEATURE:
<223> OTHER INFORMATION: Synthetic Construct

<400> SEQUENCE: 156
aagcccgatg cgccagagtt g                                 21

<210> SEQ ID NO 157
<211> LENGTH: 44
<212> TYPE: DNA
<213> ORGANISM: artificial
<220> FEATURE:
<223> OTHER INFORMATION: Synthetic Construct

<400> SEQUENCE: 157
gttgactttg acggttgcag atacagtgga tctgatatca ccta         44

<210> SEQ ID NO 158
<211> LENGTH: 44
<212> TYPE: DNA
<213> ORGANISM: artificial
<220> FEATURE:
<223> OTHER INFORMATION: Synthetic Construct

<400> SEQUENCE: 158
taggtgatat cagatccact gtatctgcaa ccgtcaaagt caac         44

<210> SEQ ID NO 159
<211> LENGTH: 27
<212> TYPE: DNA
<213> ORGANISM: artificial
<220> FEATURE:
<223> OTHER INFORMATION: Synthetic Construct

<400> SEQUENCE: 159
ttctctcctt gattatcggt ctctttc                           27

<210> SEQ ID NO 160
<211> LENGTH: 21
```

```
<212> TYPE: DNA
<213> ORGANISM: artificial
<220> FEATURE:
<223> OTHER INFORMATION: Synthetic Construct

<400> SEQUENCE: 160
tggcagatga cttcacaaac g                                              21

<210> SEQ ID NO 161
<211> LENGTH: 25
<212> TYPE: DNA
<213> ORGANISM: artificial
<220> FEATURE:
<223> OTHER INFORMATION: Synthetic Construct

<400> SEQUENCE: 161
gtggcatctt tcataacgac atctc                                          25

<210> SEQ ID NO 162
<211> LENGTH: 478
<212> TYPE: PRT
<213> ORGANISM: Pichia pastoris

<400> SEQUENCE: 162
```

Met Ser Ser Phe Arg Val Leu Asp Leu Val Lys Pro Phe Thr Pro Phe
1               5                   10                  15

Leu Pro Glu Val Ile Ser Pro Glu Arg Lys Val Pro Phe Gln Gln Lys
            20                  25                  30

Leu Met Trp Thr Gly Val Thr Leu Leu Ile Phe Leu Val Met Ser Glu
        35                  40                  45

Ile Pro Leu Tyr Gly Ile Thr Ser Ser Asp Ser Ser Asp Pro Leu Phe
    50                  55                  60

Trp Leu Arg Met Met Leu Ala Ser Asn Arg Gly Thr Leu Met Glu Leu
65                  70                  75                  80

Gly Ile Ser Pro Ile Val Thr Ser Gly Met Val Phe Gln Leu Leu Gln
                85                  90                  95

Gly Ile Gln Ile Leu Asp Val Asn Met Glu Asn Lys Ala Asp Arg Glu
            100                 105                 110

Leu Phe Gln Thr Ala Gln Lys Val Phe Ala Ile Leu Leu Ser Ile Gly
        115                 120                 125

Gln Ala Thr Val Tyr Val Leu Thr Gly Met Tyr Gly Pro Pro Gly Glu
    130                 135                 140

Leu Gly Val Gly Val Cys Leu Leu Leu Val Leu Gln Leu Val Phe Ala
145                 150                 155                 160

Gly Ile Val Val Ile Leu Leu Asp Glu Leu Leu Gln Lys Gly Tyr Gly
                165                 170                 175

Leu Gly Ser Gly Ile Ser Leu Phe Met Ala Thr Asn Ile Cys Glu Gln
            180                 185                 190

Ile Phe Trp Lys Thr Phe Ala Pro Thr Thr Val Asn Arg Gly Arg Gly
        195                 200                 205

Lys Glu Phe Glu Gly Ala Phe Ile Ser Phe Phe His Leu Ile Leu Thr
    210                 215                 220

Lys Lys Asp Lys Lys Arg Ala Leu Leu Glu Ser Phe Tyr Arg Asp Asn
225                 230                 235                 240

Ala Pro Asn Met Phe Gln Val Ile Ala Thr Leu Val Val Phe Phe Thr
                245                 250                 255

Val Val Tyr Leu Gln Gly Phe Arg Leu Glu Ile Pro Val Lys Ser Thr
            260                 265                 270

Arg Gln Arg Gly Pro Tyr Gly Thr Tyr Pro Ile Arg Leu Phe Tyr Thr
              275                 280                 285

Ser Asn Met Pro Ile Met Leu Gln Ser Ala Leu Thr Ser Asn Ile Phe
          290                 295                 300

Ile Ile Ser Gln Met Leu Tyr Ser His Phe Pro Asp Asn Ala Phe Val
305                 310                 315                 320

Lys Leu Ile Gly Thr Trp Glu Ala Gln Pro Gly Ser Ala Gln Leu Phe
              325                 330                 335

Ala Ala Ser Gly Leu Ala Tyr Tyr Met Gln Pro Pro Met Ser Leu Ser
              340                 345                 350

Gln Ala Leu Leu Asp Pro Ile Lys Thr Val Val Tyr Val Phe Val
              355                 360                 365

Leu Thr Thr Cys Ala Ile Phe Ser Lys Thr Trp Ile Glu Ile Ser Gly
370                 375                 380

Ser Ser Pro Arg Asp Val Ala Lys Gln Phe Lys Asp Gln Gly Leu Val
385                 390                 395                 400

Ile Ala Gly His Arg Asp Ala Thr Val Tyr Lys Glu Leu Lys Lys Ile
                  405                 410                 415

Ile Pro Thr Ala Ala Ala Phe Gly Gly Ala Thr Ile Gly Ala Leu Ser
              420                 425                 430

Val Val Ser Asp Leu Leu Gly Thr Leu Gly Ser Gly Thr Ser Ile Leu
              435                 440                 445

Leu Ala Val Thr Thr Ile Tyr Gly Tyr Tyr Glu Leu Ala Val Lys Glu
              450                 455                 460

Gly Gly Phe Ser Lys Gly Gly Pro Ser Gly Phe Val Asp Leu
465                 470                 475

<210> SEQ ID NO 163
<211> LENGTH: 1437
<212> TYPE: DNA
<213> ORGANISM: Pichia pastoris

<400> SEQUENCE: 163
atgagcagct tcagagttct agacttggta aagccctta ccccatttct gcctgaggtt      60
atctctccag agagaaaggt ccccttcaa cagaagttga tgtggactgg agtcactctt     120
ctgatcttct tggtcatgag tgaaattccc ctgtatggta tcacttcaag tgactcctct     180
gaccctttgt tttggctgcg tatgatgttg gcctctaaca gaggaacgct gatggagtta     240
ggtatctctc ctattgtcac ttctggaatg gtgttccaac tgttgcaggg aatccaaatc     300
ttggacgtga acatggaaaa caaagcagac agagagttgt tccaaactgc tcaaaaagtg     360
ttcgccattt tgctgagtat cggacaagct actgtttatg ttttaactgg aatgtatggc     420 cccctggtg aactaggagt tggtgtctgt cttttgttgg ttcttcaatt ggtgtttgca     480
ggtattgtgg tcatttttgtt ggatgaactc ttacaaaaag ttacggtttt aggaagtgga     540
atttctcttt tcatggccac caacatttgt gagcagattt tttggaagac ttttgctcct     600
accaccgtta accgtggaag aggtaaggaa tttgaaggag ctttcatttc tttctttcac     660
ctgatcttga ccaagaagga caagaagaga gctctgttgg aatcatttta cagagacaac     720
gctccaaaca tgttccaagt tattgctact cttgtcgtct tttttcaccgt tgtctatctt     780 cagggcttcc gtttggagat tccagttaag tctacccgtc aaagaggtcc ttacggaact     840
tacccaatca gattgttcta cacatccaac atgccaatca tgttacaatc cgcttttgacc     900 tcaaacattt tcattatttc ccagatgttg tattcacact ccctgacaa tgcctttgtt     960

```
aagctcattg gaacttggga agctcaacct ggttcagcac aactgtttgc tgcctcggga   1020
ttagcctact acatgcagcc tccaatgtcc ctgagtcaag ctttattaga ccctatcaag   1080
actgtcgtct acgttgtgtt tgttttgacc acttgtgcca tcttctccaa gacatggatt   1140
gagatttcgg gatcttcccc aagagacgtt gctaagcaat tcaaagacca aggattggtt   1200
attgctggac acagagatgc tactgtttac aaggagttga agaagattat accaacagcc   1260
gctgcatttg gaggtgccac aattggtgca ctttccgttg tttccgacct tttgggtact   1320
ttaggttcgg gaacctccat cctttggct gttacaacca tctatggtta ctacgagttg    1380
gctgttaagg aaggtggttt ttcaaagggt ggaccctctg gattcgttga tctgtaa      1437
```

RECOMBINANT HOST CELL FOR EXPRESSING PROTEINS OF INTEREST

CROSS-REFERENCE TO RELATED APPLICATIONS

This application is a 35 USC § 371 National Stage application of International Application No. PCT/EP2015/058225 filed Apr. 16, 2015, now pending; which claims the benefit under 35 USC § 119(a) to EP Application Serial No. 14165188.5 filed Apr. 17, 2014, now expired. The disclosure of each of the prior applications is considered part of and is incorporated by reference in the disclosure of this application.

FIELD OF INVENTION

The present invention is in the field of recombinant biotechnology, in particular in the field of protein expression. The invention generally relates to a method of expressing a protein of interest (POI) from a host cell. The invention relates particularly to improving a host cell's capacity to express and/or secrete a protein of interest and use of the host cell for protein expression. The invention also relates to cell culture technology, and more specifically to culturing cells to produce desired molecules for medical purposes or food products.

BACKGROUND OF THE INVENTION

Successful production of proteins of interest (POI) has been accomplished both with prokaryotic and eukaryotic hosts. The most prominent examples are bacteria like *Escherichia coli*, yeasts like *Saccharomyces cerevisiae*, *Pichia pastoris* or *Hansenula polymorpha*, filamentous fungi like *Aspergillus awamori* or *Trichoderma reesei*, or mammalian cells like CHO cells. While the yield of some proteins is readily achieved at high rates, many other proteins are only produced at comparatively low levels.

To improve the secretion of a recombinant protein, one strategy is to target on the host's secretory pathway involving the folding and processing of proteins.

Co-expression of a cDNA encoding protein disulfide isomerase (PDI) and a cDNA encoding a heterologous disulphide-bonded protein was first suggested in WO 93/25676 as a means to increase the yield of the heterologous protein. WO 93/25676 reported that the recombinant expression of antistasin and tick anticoagulant protein can be increased by co-expression with PDI.

WO 94/08012 provided methods for increasing the secretion of overexpressed protein in yeast by increasing expression of an Hsp70 chaperone protein, i.e. KAR2/BiP, or a PDI chaperone protein.

WO 05/0617818 and WO 06/067511 provided methods for producing a desired heterologous protein in yeast by using a 2 μm-based expression plasmid. It was demonstrated that the yield of a heterologous protein is substantially increased when the genes for one or more chaperone protein(s) and a heterologous protein are co-expressed on the same plasmid.

WO 2008/128701A2 described an expression system to increase the secretion of a POI from a eukaryotic cell by employing one of the following proteins BMH2, BFR2, COG6, COY1, CUP5, IMH 1, KIN2, SEC31, SSA4 and SSE1.

Another approach to increase protein production is based on the overexpression of HAC1, a transcription factor that activates the unfolded protein response (UPR). Transcriptional analyses revealed that more than 330 genes are regulated by HAC1, most of them being involved in secretion or in the biogenesis of secretory organelles. WO 01/72783 describes methods for increasing the amount of a heterologous protein secreted from a eukaryotic cell by inducing an elevated unfolded protein response (UPR), wherein the UPR is modulated by co-expression of a protein selected from the group consisting of HAC1, PTC2 and IRE1.

Wentz et al. employed a *Saccharomyces cerevisiae* yeast surface display gene library to identify improved secretion strains by applying an appropriate selection pressure. The yeast cDNAs CCW12, SED1, CWP2, RPP0 were found to enhance the display of scTCR in a temperature-dependent manner. ERO1 enhanced protein secretion when induced at 20° C. (Wentz et al., Appl. Environ. Microbiol. (2007) 73(4):1189-1198).

Liu et al. (*Biotechnol. Prog.* (2006), 22:1090-1095) showed that co-overexpression of Kar2 in *Pichia pastoris* increases rhG-CSF expression 5.6 fold. Combining KAR2 with Sec63, PDI and YDJ resulted in an increase of 2.8, 6.5 and 5.94 fold. In the experiments performed by Blatt et al, co-overexpression of KAR2 (BiP) increased A33scFv expression in *Pichia pastoris* two-fold. Combining KAR2 with PDI almost eliminated the positive KAR2 effect (Blatt et al., Appl. Microbiol. Biotechnol., 2007, 74:381-389).

Guerfall et al. examined the effect of overexpressing endogenous HAC1 in *P. pastoris*. Furthermore, HAC1 was overexpressed constitutively and inducibly. In all cases, an increased KAR2 expression as a result of induced UPR was identified. Constitutive overexpression of full-length HAC1 had little or no effect, while overexpression of the induced form of HAC1 led to an increase of protein secretion in one out of four cases, and a decrease in three out of four cases (Guerfall et al., Microbial Cell Factories, (2010), 9:49).

Sleep et al. showed that co-overexpression of Lhs1 increases the concentration of rHA. LHS1 was combined with SIL1, JEM1 and SCJ1, but titers were lower than with JEM1 co-overexpressed alone. Co-overexpression of SIL1, LHS1 and JEM1 at the same time increased GM-CSF expression by 1.45 fold and the rHA expression by approximately 1.1 and 2 fold, dependent on the cultivation media (Sleep et al. Applied and Environmental Microbiology, (2008) 74(24):7759-7766).

US 2009221030 A1 described the co-expression of various helper proteins, inter alia, BiP1, alone and in combination with other helper proteins, inter alia, LHS1, in *Trichoderma reesei*. The highest expression values were obtained with BiP1 alone, while the combination of BiP1 and LHS1 lead to 8% lower secreted protein titers.

U.S. Pat. No. 8,440,456 provided the genome sequence of *Pichia pastoris* and disclosed nucleic acid sequences encoding signal peptides, chaperons and promoters. It disclosed expression vectors comprising the nucleic acid sequences and genetically engineered yeast capable of overexpression of 14 chaperones. ROT1, SHR3 and SIL1 were specifically selected for testing, however, no expression was observed for SIL1, and overexpression of ROT1 or SHR3 failed to lead to any significant enhancement of the secretion of heterologous proteins. While overexpression of genes encoding helper proteins is usually applied to enhance expression of a protein of interest, underexpression of a gene encoding a protein or even a knock-out of the gene encoding it is not or only rarely applied.

High level of protein yield in host cells may be limited at one or more different steps, like folding, disulfide bond formation, glycosylation, transport within the cell, or release from the cell. Many of the mechanisms involved are still not fully understood and cannot be predicted on the basis of the current knowledge of the state-of-the-art, even when the DNA sequence of the entire genome of a host organism is available.

There is a constant need for methods to improve a host cell's capacity to produce and/or secret proteins of interest. One object of the invention is to provide new methods to increase the yield of proteins in host cells which are simple and efficient and suitable for use in industrial methods. It is another object to provide host cells to achieve this purpose.

It must be noted that as used herein, the singular forms "a", "an" and "the" include plural references and vice versa unless the context clearly indicates otherwise. Thus, for example, a reference to "a host cell" or "a method" includes one or more of such host cells or methods, respectively, and a reference to "the method" includes equivalent steps and methods that could be modified or substituted known to those of ordinary skill in the art. Similarly, for example, a reference to "methods" or "host cells" includes "a host cell" or "a method", respectively.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term". For example, A, B and/or C means A, B, C, A+B, A+C, B+C and A+B+C.

The term "about" or "approximately" as used herein means within 20%, preferably within 10%, and more preferably within 5% of a given value or range. It includes also the concrete number, e.g., about 20 includes 20.

The term "less than", "more than" or "larger than" includes the concrete number. For example, less than 20 means 20 and more than 20 means 20.

Throughout this specification and the claims or items, unless the context requires otherwise, the word "comprise" and variations such as "comprises" and "comprising" will be understood to imply the inclusion of a stated integer (or step) or group of integers (or steps). It does not exclude any other integer (or step) or group of integers (or steps). When used herein, the term "comprising" can be substituted with "containing", "composed of", "including", "having" or "carrying." When used herein, "consisting of" excludes any integer or step not specified in the claim/item. When used herein, "consisting essentially of" does not exclude integers or steps that do not materially affect the basic and novel characteristics of the claim/item. In each instance herein any of the terms "comprising", "consisting essentially of" and "consisting of" may be replaced with either of the other two terms.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

It should be understood that this invention is not limited to the particular methodology, protocols, material, reagents, and substances, etc., described herein. The terminologies used herein are for the purpose of describing particular embodiments only and are not intended to limit the scope of the present invention, which is defined solely by the claims/items.

All publications and patents cited throughout the text of this specification (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

SUMMARY

The present invention is partly based on the surprising findings of several proteins (herein referred to as knockout (KO) proteins), including KO1, KO2, KO3 (also referred to herein as KO protein 1, KO protein 2, and KO protein 3, respectively) and functional homologues thereof, whose expression was observed to have a negative impact on the yield of POI from a host cell. The meaning of functional homologue is defined in the latter part of the application. Furthermore, it has been discovered that a modification of the genes such as mutation or deletion is able to increase the yield of POI. This disclosure provides methods and materials useful for improving the yield of POI by engineering host cells such that they underexpress the genes identified by the inventors. The term "yield" refers to the amount of POI or model protein(s) as described herein, in particular SDZ-Fab (SEQ ID NO: 25 and 26) and HyHEL-Fab (SEQ ID NO: 29 and 30), respectively, which is, for example, harvested from the engineered host cell, and increased yields can be due to increased amounts of production or secretion of the POI by the host cell. Yield may be presented by mg POI/g biomass (measured as dry cell weight or wet cell weight) of a host cell. The term "titer" when used herein refers similarly to the amount of produced POI or model protein, presented as mg POI/L culture supernatant. An increase in yield can be determined when the yield obtained from an engineered host cell is compared to the yield obtained from a host cell prior to engineering, i.e., from a non-engineered host cell.

Preferably, "yield" when used herein in the context of a model protein as described herein, is determined as described in Example 5c. Accordingly, the "yield" when used herein in the context of a model protein as described herein is also referred to as "Fab yield" or "Fab titer". A Fab titer is given as mg/L and a Fab yield as mg/biomass (measured as dry cell weight or wet cell weight).

Briefly, *P. pastoris* strains CBS7435mut$^s$ pPM2d_pAOX HyHEL and/or CBS7435mut$^s$ pPM2d_pAOX SDZ (see Example 1 for their generation) which express the model protein HyHEL-Fab and SDZ-Fab, respectively, are engineered with a polynucleotide encoding a helper protein or functional homologue thereof as described herein. For co-overexpression, the gene encoding a helper protein is cloned under control of the *P. pastoris* GAP promoter and transformed into the Fab producing strains as described in example 4. For underexpression the gene encoding a KO target or its functional homologue is knocked out from the genome of the Fab producing strain (see example 6). Engineered cells are grown in YP-medium containing 10 g/L glycerol and 50 µg/mL Zeocin overnight at 25° C. (see Example 5a). Aliquots of such a culture (corresponding to a final $OD_{600}$ of 2.0) are transferred to synthetic medium M2 containing 20 g/L glucose and a glucose feed tablet (described in Example 5a) and incubated for 25 h at 25° C. Cultures are washed and resuspended in synthetic medium M2 and aliquots (corresponding to a final $OD_{600}$ of 4.0) are transferred into synthetic medium M2 supplemented with 5 g/L methanol. Methanol (5 g/L) is added 3 more times every 12 hours. After 48 h, cells are harvested by centrifugation. Biomass is determined by measuring the weight of the cell pellet derived from 1 mL cell suspension. The supernatant is used for quantification of SDZ-Fab or HyHEL-Fab, respectively, by ELISA (described in Example 5c). Specifically, an anti-human IgG antibody (e.g. ab7497, Abcam) is used as coating antibody and a e.g. goat anti-human anti-human IgG (Fab specific) antibody (e.g. Sigma A8542, alkaline phosphatase conjugated) is used as detection antibody. Commercial Human Fab/Kappa, IgG fragment is used as standard with a starting concentration of 100 ng/mL, supernatant samples are diluted accordingly. An increase in the yield may be determined based on a comparison of POI yield before and after the cell is engineered to underexpress the polypeptide encoding the KO protein. A standard test as shown in the example may be used to determine the yield difference.

The present invention is partly based on, but not limited to, the following knockout proteins which are discovered by the inventors:

As to the genes that have to be knocked-out—from a chaperone (KO2, KO3) one would have expected that overexpression is beneficial, but it is in fact the deletion that has a positive effect.

KO1 which plays a role in flocculation in baker's yeast, one would not have expected that its deletion enhances protein secretion. Flocculation in baker's yeast is a phenomenon when cells aggregate reversibly in a vegetative growth phase, not related to mating.

In a first aspect, the present invention provides a recombinant host cell for manufacturing a protein of interest, wherein the host cell is engineered to underexpress at least one polynucleotide encoding a KO protein having an amino acid sequence as shown in SEQ ID NO: 10, 11, 12 or a functional homologue thereof, wherein the functional homologue has at least 30%, such as at least 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, sequence identity to an amino acid sequence as shown in SEQ ID NO: 10, 11 or 12.

The recombinant host cell is obtained by first providing a host cell which comprises at least one polynucleotide encoding a KO protein having an amino acid sequence as shown in SEQ ID NO: 10, 11, 12 or a functional homologue thereof, wherein the functional homologue has at least 30%, such as at least 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, sequence identity to an amino acid sequence as shown in SEQ ID NO: 10, 11 or 12, and then engineering the host cell to underexpress the polynucleotide.

TABLE 1

| KO proteins | (Designation (in analogy to S. cerevisiae)) | Amino acid sequences | Polynucleotides | Designation in the Examples (see Table 7) |
|---|---|---|---|---|
| KO1 | FLO8 | SEQ ID NO: 10 | SEQ ID NO: 22 | PP7435_Chr4-0252 |
| KO2 | HCH1 | SEQ ID NO: 11 | SEQ ID NO: 23 | PP7435_Chr3-1062 |
| KO3 | SCJ1 | SEQ ID NO: 12 | SEQ ID NO: 24 | PP7435_Chr1-0176 |

The present invention provides genetically engineered recombinant host cells having one or more underexpressed genes encoding the KO protein. As used herein, "engineered" host cells are host cells which have been manipulated using genetic engineering, i.e. by human intervention. When a host cell is "engineered to underexpress" a given protein, the host cell is manipulated such that the expression level of a functional KO protein is decreased compared to the host cell under the same condition prior to the genetic manipulation to achieve underexpression. The host cell which is to be subjected to genetic engineering comprises at least one, such as at least 2, or at least 3 polynucleotide sequence encoding a KO protein or functional homologues thereof. Genetic engineering results in the underexpression of genes encoding the KO protein. Preferably, the engineering will result in a cell having no detectable level for the KO protein(s). Underexpression can be observed by comparing the engineered host cell with a "corresponding parent strain" which refers to the host cell prior to aforementioned engineering. As used herein, KO proteins are referred to in the present invention interchangeably in plural or singular forms, which however should be understood as in singular form unless expressly stated otherwise.

In a preferred embodiment, the host cell is a yeast cell, preferably a host cell of the genus *Pichia* and more preferably *Pichia pastoris* which does not comprise a KO protein of the present invention and/or which does not comprise a polynucleotide encoding the KO protein(s). In one embodiment, the host cell is one obtained by deleting a polynucleotide sequence as shown in SEQ ID NO: 22, 23, 24, or homologous thereof.

As used herein, a "homologue" or "functional homologue" of a polypeptide shall mean that a polypeptide has the same or conserved residues at a corresponding position in their primary, secondary or tertiary structure. The term also extends to two or more nucleotide sequences encoding homologous polypeptides. In particular, polypeptides homologous to the KO1, KO2 and KO3 described in the examples may have at least about 30%, such as at least 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, amino acid sequence identity with regard to a full-length native sequence or any fragment thereof. Preferably, a homologous polypeptide will have at least about 35% amino acid sequence identity, more preferably at least about 40% amino acid sequence identity, more preferably at least about 45% amino acid sequence identity, more preferably at least about 50% amino acid sequence identity, more preferably at least about 55% amino acid sequence identity, more preferably at least about 60% amino acid sequence identity, more preferably at least about 65% amino acid sequence identity, more preferably at least about 70% amino acid sequence identity, more preferably at least about 75% amino acid sequence identity, more preferably at least about 80% amino acid sequence identity, more preferably at least about 85% amino acid sequence identity, more preferably at least about 90%, such as 91, 92, 93, 94, 95, 96, 97, 98 or 99% amino acid sequence identity, more preferably at least about 95% amino acid sequence identity to a native compound, or any other specifically defined fragment of a full-length compound. When the function as a KO1, KO2, and KO3 protein is proven with such a homologue, the homologue is called "functional homologue". A functional homologue performs the same or substantially the same function as the KO protein or helper protein from which it is derived from, i.e. it increases the yield of the model protein SDZ-Fab and/or HyHEL-Fab as described herein. The function can be tested by assay known in the art or preferably with the assay using the model proteins as described in Example 7 or Example 5c, particularly as described herein above in the context of "Fab titer" or "Fab yield".

The function of a potential functional homologue can be tested by providing expression cassettes into which the functionally equivalent variant sequences have been inserted, transforming host cells that carry the sequence encoding a test protein such as one of the model proteins used in the Example or a specific POI, and determining the difference in the yield of the model protein or POI under identical conditions.

In one embodiment, the host cell is engineered to underexpress KO protein 1. The host cell is preferably engineered to underexpress a polynucleotide encoding a protein having an amino acid sequence as shown in SEQ ID NO: 10 or a functional homologue thereof, wherein the functional homologue has at least 30%, such as at least 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, sequence identity to an amino acid sequence as shown in SEQ ID NO: 10.

In another embodiment, the host cell is engineered to underexpress KO2. The host cell is preferably engineered to underexpress a polynucleotide encoding a protein having an amino acid sequence as shown in SEQ ID NO: 11 or a functional homologue thereof, wherein the functional homologue has at least 30%, such as at least 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, sequence identity to an amino acid sequence as shown in SEQ ID NO: 11.

In a further embodiment, the host cell is engineered to underexpress KO3. The host cell is preferably engineered to underexpress a polynucleotide encoding a protein having an amino acid sequence as shown in SEQ ID NO: 12 or a functional homologue thereof, wherein the functional homologue has at least 30%, such as at least 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, sequence identity to an amino acid sequence as shown in SEQ ID NO: 12.

The present invention provides an isolated polynucleotide sequence comprising, consisting essentially of, or consisting of SEQ ID NO: 22, SEQ ID NO: 23, or SEQ ID NO: 24, Furthermore, the present invention provides an isolated polynucleotide sequence which encodes a polypeptide sequence comprising any one of SEQ ID NO: 10, 11, 12, or functional homologues thereof. In some embodiments, the present invention provides an isolated polynucleotide sequence having at least 30%, such as at least 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% sequence identity to a polynucleotide sequence selected from the group consisting of SEQ ID NO: 22, 23, 24. More preferably, the isolated polynucleotide sequence has 100% sequence identity with SEQ ID NO: 22, SEQ ID NO23, SEQ ID NO: 24.

Furthermore, the present invention provides an isolated polypeptide comprising the polypeptide sequence of any one of SEQ ID NO: 10, 11, 12, or functional homologues thereof. Preferably, the present invention provides an isolated polypeptide comprising the polypeptide sequence of SEQ ID NO: 10 or functional homologues thereof. Preferably, the present invention provides an isolated polypeptide comprising the polypeptide sequence of SEQ ID NO: 11 or functional homologues thereof. Preferably, the present invention provides an isolated polypeptide comprising the polypeptide sequence of SEQ ID NO: 12 or functional homologues thereof. In a further aspect, the present invention provides an isolated polypeptide with a polypeptide sequence having at least 30%, such as at least 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% sequence identity to an amino acid sequence selected from the group consisting of SEQ ID NO: 10, 11, or 12.

The term "nucleotide sequence" or "nucleic acid sequence" used herein refers to either DNA or RNA. "Nucleic acid sequence" or "polynucleotide sequence" or simply "polynucleotide" refers to a single or double-stranded polymer of deoxyribonucleotide or ribonucleotide bases read from the 5' to the 3' end. It includes both self-replicating plasmids, infectious polymers of DNA or RNA, and non-functional DNA or RNA.

The term "expressing a polynucleotide" means when a polynucleotide is transcribed to mRNA and the mRNA is translated to a polypeptide. The term "underexpress" generally refers to any amount less than an expression level exhibited by a reference standard, which is the host cell prior to the engineering to underexpress the KO protein. The terms "underexpress," "underexpressing," "underexpressed" and "underexpression" in the present invention refer an expression of a gene product or a polypeptide at a level less than the expression of the same gene product or polypeptide prior to a genetic alteration of the host cell or in a comparable host which has not been genetically altered. "Less than" includes, e.g., 10%, 20%, 30%, 40%, 50%, 60%, 70%, 80, 90% or more. No expression of the gene product or a polypeptide is also encompassed by the term "underexpression."

The host cell may be obtained by providing a cell which expresses KO protein 1 or functional homologues thereof and engineering the cell to underexpress the gene which encodes KO protein 1. The host cell may also be obtained by providing a cell which expresses KO protein 2 or functional homologues thereof and engineering the cell to underexpress the gene which encodes KO protein 2. Furthermore, the host cell may be obtained by providing a cell which expresses KO protein 3 or functional homologues thereof and engineering the cell to underexpress the gene encoding KO protein 3.

In a preferred embodiment, the KO protein 1, when preferably underexpressed, may increase the production of the model protein SDZ-Fab or HyHEL-Fab in the host cell by at least 1%, such as at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190 or at least 200% or more, compared to the host cell prior to the engineering to underexpress the polynucleotide encoding the KO protein. It has been surprisingly found that exemplary recombinant cells described in the Examples were all able to increase the yield of the model protein SDZ-Fab or HyHEL-Fab by at least 20% (1.2 fold change).

In a preferred embodiment, the KO protein 2, when preferably underexpressed, may increase the yield of the model protein SDZ-Fab or HyHEL-Fab in the host cell by at least 1%, such as at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190 or at least 200% or more, compared to the host cell prior to engineering. It has been surprisingly found that exemplary recombinant cells described in the Examples were all able to increase the yield of the model protein SDZ-Fab or HyHEL-Fab by at least 20% (1.2 fold change).

In a preferred embodiment, the KO protein 3, when preferably underexpressed, may increase the yield of the model protein SDZ-Fab or HyHEL-Fab in the host cell by at least 1%, such as at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190 or at least 200% or more, compared to the host cell prior to engineering. It has been surprisingly found that exemplary recombinant cells described in the Examples were all able to increase the yield of the model protein SDZ-Fab or HyHEL-Fab by at least 20% (1.2 fold change).

In a third aspect, the present invention provides use of any of the recombinant host cells described in the present for manufacturing a protein of interest.

In a fourth aspect, the present invention provides a method of increasing the yield of a protein of interest in a host cell, comprising underexpressing at least one polynucleotide encoding a KO protein having an amino acid sequence as shown in SEQ ID NO: 10, 11, 12 or a functional homologue thereof, wherein the functional homologue has at least 30%, such as at least 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, sequence identity to an amino acid sequence as shown in SEQ ID NO: 10, 11 or 12.

Preferably, the method comprises underexpressing a polynucleotide encoding a KO protein having an amino acid sequence as shown in SEQ ID NO: 10 or a functional homologue thereof, wherein the functional homologue has having at least 30%, such as at least 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, sequence identity to an amino acid sequence as shown in SEQ ID NO: 10.

Preferably, the method comprises underexpressing a polynucleotide encoding a KO protein having an amino acid sequence as shown in SEQ ID NO: 11 or a functional homologue thereof, wherein the functional homologue has at least 30%, such as at least 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, sequence identity to an amino acid sequence as shown in SEQ ID NO: 11.

Preferably, the method comprises underexpressing a polynucleotide encoding a KO protein having an amino acid sequence as shown in SEQ ID NO: 12 or a functional homologue thereof, wherein the functional homologue has at least 30%, such as at least 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, sequence identity to an amino acid sequence as shown in SEQ ID NO: 12.

In a fifth aspect, the present invention provides a method of increasing the yield of a protein of interest in a host cell comprising:

engineering the host cell to underexpress at least one, such as at least 2, or at least 3, polynucleotide encoding a KO protein having an amino acid sequence as shown in SEQ ID NO: 10, 11, 12 or a functional homologue thereof, wherein the functional homologue has at least 30%, such as at least 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, sequence identity to an amino acid sequence as shown in SEQ ID NO: 10, 11 or 12, recombining in said host cell a heterologous polynucleotide encoding a protein of interest, and culturing said host cell under suitable conditions to express the protein of interest.

In the context of methods for increasing the yield of a protein the order of the "engineering step" and "recombining step" can alternatively be reversed such that the "recombining step" precedes the "engineering step". Notably, as described herein, the yield of a protein of interest is increased when a KO protein is underexpressed and/or a helper protein is overexpressed.

It should be noted that the engineering step and the recombining step do not have to be performed in the recited sequence. It is possible to perform the steps in different order.

Preferably, the present invention provides a method of increasing the yield of a protein of interest in a host cell comprising:

engineering the host cell to underexpress at least one polynucleotide encoding a KO protein having an amino acid sequence as shown in SEQ ID NO: 10, 11, 12 or a functional homologue thereof, wherein the functional homologue has at least 30%, such as at least 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, sequence identity to an amino acid sequence as shown in SEQ ID NO: 10, recombining in said host cell a heterologous polynucleotide encoding a protein of interest, and culturing said host cell under suitable conditions to express the protein of interest.

Preferably, the present invention provides a method of increasing the yield of a protein of interest in a host cell comprising:

engineering the host cell to underexpress at least one polynucleotide encoding a KO protein having an amino acid sequence as shown in SEQ ID NO: 10, 11, 12 or a functional homologue thereof, wherein the functional homologue has at least 30%, such as at least 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, sequence identity to an amino acid sequence as shown in SEQ ID NO: 11, recombining in said host cell a heterologous polynucleotide encoding a protein of interest, and culturing said host cell under suitable conditions to express the protein of interest.

Preferably, the present invention provides a method of increasing the yield of a protein of interest in a host cell comprising:

engineering the host cell to underexpress at least one polynucleotide encoding a KO protein having an amino acid sequence as shown in SEQ ID NO: 10, 11, 12 or a functional homologue thereof, wherein the functional homologue has at least 30%, such as at least 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, sequence identity to an amino acid sequence as shown in SEQ ID NO: 12, recombining in said host cell a heterologous polynucleotide encoding a protein of interest, and culturing said host cell under suitable conditions to express the protein of interest.

In a sixth aspect, the present invention provides a method of producing a protein of interest in host cell comprising:

providing a host cell engineered to underexpress at least one, such as at least 2, or at least 3 polynucleotide encoding a KO protein sequence as shown in SEQ ID NO: 10, 11, 12 or a functional homologue thereof, wherein the functional homologue has an amino acid having at least 30%, such as at least 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, sequence identity to an amino acid sequence as shown in SEQ ID NO: 10, 11 or 12, wherein said host cell comprises a heterologous polynucleotide encoding a protein of interest; and culturing the host cell under suitable conditions to express the protein of interest.

Preferably, the present invention provides a method of producing a protein of interest in a host cell comprising:

providing a host cell engineered to underexpress at least one polynucleotide encoding a KO protein having an amino acid sequence as shown in SEQ ID NO: 10, 11, 12 or a functional homologue thereof, wherein the functional homologue has at least 30%, such as at least 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, sequence identity to an amino acid sequence as shown in SEQ ID NO: 10, wherein said host cell comprises a heterologous polynucleotide encoding a protein of interest; and culturing the host cell under suitable conditions to express the protein of interest.

Preferably, the present invention provides a method of producing a protein of interest in a host cell comprising:

providing a host cell engineered to underexpress at least one polynucleotide encoding a KO protein having an amino acid sequence as shown in SEQ ID NO: 10, 11, 12 or a functional homologue thereof, wherein the functional homologue has at least 30%, such as at least 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, sequence identity to an amino acid sequence as shown in SEQ ID NO: 11, wherein said host cell comprises a heterologous polynucleotide encoding a protein of interest; and culturing the host cell under suitable conditions to express the protein of interest.

Preferably, the present invention provides a method of producing a protein of interest in host cell comprising:

providing a host cell engineered to underexpress at least one polynucleotide encoding a KO protein having an amino acid sequence as shown in SEQ ID NO: 10, 11, 12 or a functional homologue thereof, wherein the functional homologue has at least 30%, such as at least 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, sequence identity to an amino acid sequence as shown in SEQ ID NO: 12, wherein said host cell comprises a heterologous polynucleotide encoding a protein of interest; and culturing the host cell under suitable conditions to express the protein of interest.

The present invention encompasses the underexpression of 2 or all of KO1, KO2 and KO3 genes. The present invention also encompasses the recombinant host cell for manufacturing a protein of interest, wherein the host cell is engineered to underexpress at least 2, 3 or more polynucleotide encoding a KO protein having an amino acid sequence as shown in SEQ ID NO: 10, 11, 12 or a functional homologue thereof, wherein the functional homologue has at least 30% sequence identity to an amino acid sequence as shown in SEQ ID NO: 10, 11 or 12. In some embodiments 2, 3, 4, 5, 6 or more of KO proteins selected from SEQ ID NO: 10, 11, 12 or functional homologues thereof are underexpressed in the host cell. A functional homologue may be a biologically active fragment of the KO proteins. Generally, biologically active fragment of a protein shall mean a fragment that exerts a biological effect similar or comparable to that of the full length protein. Such fragments or variants can be produced e.g. by amino- and/or carboxy-terminal deletions as well as by internal deletions.

BRIEF DESCRIPTION OF THE DRAWINGS

FIGS. 1A-1H show the amino acid and polynucleotide sequences of the HP1, HP2, HP 3, HP 4, HP5, HP6, HP7, HP8, HP9, HP10, KO1, KO2 and KO3.

FIGS. 2A-2B show the amino acid and polynucleotide sequences of the heavy chain and light chain of the model proteins SDZ-Fab and HyHEL-Fab, respectively.

ITEMS OF THE INVENTION

1. A recombinant host cell for manufacturing a protein of interest, wherein the host cell is engineered to underexpress at least one polynucleotide encoding a KO protein having an amino acid sequence as shown in SEQ ID NO: 10, 11, 12 or a functional homologue thereof, wherein the functional homologue has at least 30% sequence identity to an amino acid sequence as shown in SEQ ID NO: 10, 11 or 12.
2. The host cell of item 1, wherein said polynucleotide encoding the KO protein or a functional homologue thereof, preferably when underexpressed, increases the yield of the model protein SDZ-Fab (SEQ ID NO: 25 and 26) and/or HyHEL-Fab (SEQ ID NO: 29 and 30), preferably by at least 20% compared to the host cell prior to engineering.
3. The host cell in item 1 or 2, wherein underexpression is achieved by knocking out the polynucleotide encoding the KO protein or a functional homologue thereof from the genome of said the host cell.
4. The host cell in item 1 or 2, wherein underexpression is achieved by disrupting the polynucleotide encoding the KO protein or a functional homologue thereof in the host cell.
5. The host cell in item 1 or 2, wherein underexpression is achieved by disrupting a promoter which is operably linked with said polypeptide encoding the KO protein or a functional homologue thereof.
6. The host cell in item 1 or 2, wherein underexpression is achieved by post-transcriptional gene silencing.
7. The host cell in any one of the preceding items, wherein the host cell is a *Pichia pastoris, Hansenula polymorpha, Trichoderma reesei, Saccharomyces cerevisiae, Kluyveromyces lactis, Yarrowia lipolytica, Pichia methanolica, Candida boidinii,* and *Komagataella,* and *Schizosaccharomyces pombe.*
8. The host cell of any of the preceding items, wherein the protein of interest is an enzyme, a therapeutic protein, a food additive or feed additive, preferably a detoxifying enzyme.
9. The host cell of item 8, wherein the therapeutic protein comprises an antibody or antibody fragment
10. The host cell in any of the preceding items, wherein said polynucleotide encoding the KO protein, preferably when underexpressed, increases the yield of the model protein SDZ-Fab (SEQ ID NO: 25 and 26) and/or HyHEL-Fab (SEQ ID NO: 29 and 30) by preferably at least 20% compared to the host cell prior to engineering.
11. The host cell in any one of the preceding items, wherein the host cell underexpresses said at least one polynucleotide encoding the KO protein or a functional homologue thereof and expresses the protein of interest.
12. The host cell in any one of the preceding items, wherein the host cell comprises at least one polynucleotide encoding a helper protein.
13. The host cell of item 12, wherein the helper protein has an amino acid sequence as shown in SEQ ID NO: 1, 2, 3, 4, 5, 6, 7, 8, 9, or 162 or a functional homologue thereof, wherein the functional homologue has at least 30% sequence identity to an amino acid sequence as shown in SEQ ID NO: 1, 2, 3, 4, 5, 6, 7, 8, 9, or 162.
14. The host cell of item 12 or 13, wherein the host cell is engineered to express or overexpress the helper protein or a functional homologue thereof.
15. The host cell of any one of the preceding claims, wherein the host cell is engineered to
   (i) underexpress a polynucleotide encoding a protein having an amino acid as shown in SEQ ID NO: 10 or a functional homologue thereof and further engineered to overexpress a polynucleotide encoding a helper protein having an amino acid sequence as shown in SEQ ID NO: 1 or a functional homologue thereof and a helper protein having an amino acid sequence as shown in SEQ ID NO: 2 or a functional homologue thereof, or
   (ii) underexpress a polynucleotide encoding a protein having an amino acid as shown in SEQ ID NO: 10 or a functional homologue thereof and further engineered to overexpress a polynucleotide encoding a helper protein having an amino acid sequence as shown in SEQ ID NO: 4 or a functional homologue thereof and SEQ ID NO: 1 or a functional homologue thereof.
16. A host cell obtained by providing a cell which expresses KO protein 1 or functional homologues thereof and engineering the cell to underexpress the gene which encodes KO1.
17. A host cell obtained by providing a cell which expresses KO protein 2 or functional homologues thereof and engineering the cell to underexpress the gene which encodes KO2.
18. A host cell obtained by providing a cell which expresses KO protein 3 or functional homologues thereof and engineering the cell to underexpress the gene encoding KO3.
19. Use of the host cell in any one of the preceding items for manufacturing a protein of interest.
20. A method of increasing the yield of a protein of interest in a host cell, comprising underexpressing at least one polynucleotide encoding a KO protein having an amino acid sequence as shown in SEQ ID NO: 10, 11, 12 or a functional homologue thereof, wherein the functional homologue has at least 30% sequence identity to an amino acid sequence as shown in SEQ ID NO: 10, 11 or 12.
21. A method of increasing the yield of a protein of interest in a host cell comprising:
   engineering the host cell to underexpress at least one polynucleotide encoding a KO protein having an amino acid sequence as shown in SEQ ID NO: 10, 11, 12 or a functional homologue thereof, wherein the functional homologue has at least 30% sequence identity to an amino acid sequence as shown in SEQ ID NO: 10, 11 or 12,
   recombining in said host cell a heterologous polynucleotide encoding a protein of interest, culturing said host cell under suitable conditions to express the protein of interest, and optionally isolating the protein of interest from the cell culture.

22. A method of producing a protein of interest in a host cell comprising:

providing a host cell engineered to underexpress at least one polynucleotide encoding an KO protein having an amino acid sequence as shown in SEQ ID NO: 10, 11, 12 or a functional homologue thereof, wherein the functional homologue has at least 30% sequence identity to an amino acid sequence as shown in SEQ ID NO: 10, 11 or 12, wherein said host cell comprises a heterologous polynucleotide encoding a protein of interest;

culturing the host cell under suitable conditions to express protein of interest, and optionally isolating the protein of interest from the cell culture.

23. The method in any one of items 20-22, wherein underexpression is achieved by knocking out the polynucleotide encoding the KO protein or a functional homologue thereof from the genome of said the host cell.

24. The method in any one of items 20-22, wherein underexpression is achieved by disrupting the polynucleotide encoding the KO protein or a functional homologue thereof in the host cell.

25. The method in any one of items 20-23, wherein underexpression is achieved by disrupting a promoter which is operably linked with said polypeptide encoding the KO protein or a functional homologue thereof.

26. The method in any one of items 20-24, wherein underexpression is achieved by post-transcriptional gene silencing, preferably by expression of a heterologous RNA sequence which binds to transcripts from the polynucleotide encoding the KO protein.

27. The method in any one of items 20-26, wherein the host cell is a *Pichia pastoris, Hansenula polymorpha, Trichoderma reesei, Saccharomyces cerevisiae, Kluyveromyces lactis, Yarrowia lipolytica, Pichia methanolica, Candida boidinii*, and *Komagataella*, and *Schizosaccharomyces pombe*.

28. The method in any of items 20-27, wherein the protein of interest is an enzyme, a therapeutic protein, a food additive or feed additive, preferably a detoxifying enzyme.

29. The method of item 28, wherein the therapeutic protein comprises an antibody, or antibody fragment.

30. The method of any of items 20-29, wherein said polynucleotide encoding the KO protein, preferably when underexpressed, increases the yield of the model protein SDZ-Fab (SEQ ID NO: 25 and 26) and/or HyHEL-Fab (SEQ ID NO: 29 and 30) by preferably at least 20% compared to the host cell prior to engineering 31. The method in any one of items 20-30, wherein the host cell comprises a polynucleotide encoding at least one helper protein.

32. The method of item 31, wherein the helper protein has an amino acid sequence as shown in SEQ ID NO: 1, 2, 3, 4, 5, 6, 7, 8, 9, or 162 or a functional homologue thereof, wherein the functional homologue has at least 30% sequence identity to an amino acid sequence as shown in SEQ ID NO: 1, 2, 3, 4, 5, 6, 7, 8, 9, or 162.

33. The method of any one of items 31 or 32, wherein the host cell is engineered to express or overexpress a helper protein having an amino acid sequence as shown in SEQ ID NO: 1, 2, 3, 4, 5, 6, 7, 8, 9, or 162 or a functional homologue thereof, wherein the functional homologue has at least 30% sequence identity to an amino acid sequence as shown in SEQ ID NO: 1, 2, 3, 4, 5, 6, 7, 8, 9, or 162.

34. A composition comprising at least 10%, 20%, 30%, 40%, or 50% of a protein of interest and a polynucleotide encoding a helper protein as defined in item 13, wherein said polynucleotide is operably linked with a heterologous promoter.

DETAILED DESCRIPTION OF THE INVENTION

The present invention is concerned with the manipulation of KO1, KO2 and/or KO3 genes in host cells. It has been surprisingly found that the manipulated host has an increased capacity to produce an expressed protein of interest.

In a first aspect, the preset invention provides a recombinant host cell for manufacturing a protein of interest, wherein the host cell is engineered to underexpress at least one, such as at least 2, or at least 3, polynucleotide encoding a KO protein having an amino acid sequence as shown in SEQ ID NO: 10, 11, 12 or a functional homologue thereof, wherein the functional homologue has at least 30% sequence identity to an amino acid sequence as shown in SEQ ID NO: 10, 11 or 12.

For the purpose of the present invention the term "KO protein" is also meant to encompass functional homologues of KO1, KO2, or KO3.

KO Proteins 1

The function of FLO8 in baker's yeast is presumably a transcriptional activator that is required for diploid filamentous growth and haploid invasive growth and flocculation. It has never been suggested to lead to an increased yield of protein production in a yeast or other host cell.

KO Protein 2

KO2 encodes in baker's yeast the co-chaperone HCH1. HCH1 in some yeasts were found to regulate Hsp90 function (Armstrong et al., PLoS One. 2012; 7(11):e49322.). It has never been suggested before that the underexpression of this protein leads to an increased yield of POI in a host cell.

KO Protein 3

KO protein 3 encodes in baker's yeast one of several homologs of the bacterial chaperone DnaJ. It has never been suggested before that the underexpression of this protein leads to an increased yield of POI in the host cell.

From a chaperone (KO2, KO3) one would have expected that overexpression is beneficial, but it is in fact the deletion that has a positive effect. For KO1 which plays a role in flocculation in baker's yeast, one would not have expected that its deletion enhances protein secretion. Flocculation in baker's yeast is a phenomenon when cells aggregate reversibly in a vegetative growth phase, not related to mating. However, a skilled person would most likely not have assumed that knocking-out a flocculation gene enhances protein secretion.

"Sequence identity" or "% identity" refers to the percentage of residue matches between at least two polypeptide or polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. For purposes of the present invention, the sequence identity between two amino acid sequences or nucleotide is determined using the NCBI BLAST program version 2.2.29 (Jan. 6, 2014) (Altschul et al., Nucleic Acids Res. (1997) 25:3389-3402). Sequence identity of two amino acid sequences can be determined with blastp set at the following parameters: Matrix: BLOSUM62, Word Size: 3; Expect value: 10; Gap cost: Existence=11, Extension=1; Filter=low complexity activated; Filter String: L; Compositional adjustments: Conditional compositional score matrix adjustment. For purposes of the present invention, the sequence identity between two nucleotide sequences is determined using the NCBI BLAST program version 2.2.29 (Jan. 6, 2014) with blastn set at the following parameters: Word Size: 11; Expect value: 10; Gap costs: Existence=5, Extension=2; Filter=low complexity activated; Match/Mismatch Scores: 2, −3; Filter String: L; m.

Host Cell

As used herein, a "host cell" refers to a cell which is capable of protein expression and optionally protein secretion. Such host cell is applied in the methods of the present invention. For that purpose, for the host cell to express a polypeptide, a nucleotide sequence encoding the polypeptide is present or introduced in the cell. Host cells provided by the present invention can be prokaryotes or eukaryotes. As will be appreciated by one of skill in the art, a prokaryotic cell lacks a membrane-bound nucleus, while a eukaryotic cell has a membrane-bound nucleus. Examples of eukaryotic cells include, but are not limited to, vertebrate cells, mammalian cells, human cells, animal cells, invertebrate cells, plant cells, nematodal cells, insect cells, stem cells, fungal cells or yeast cells.

Examples of yeast cells include but are not limited to the *Saccharomyces* genus (e.g. *Saccharomyces cerevisiae*, *Saccharomyces kluyveri*, *Saccharomyces uvarum*), the *Komagataella* genus (*Komagataella pastoris*, *Komagataella pseudopastoris* or *Komagataella phaffii*), *Kluyveromyces* genus (e.g. *Kluyveromyces lactis*, *Kluyveromyces mandanus*), the *Candida* genus (e.g. *Candida utifis*, *Candida cacaoi*, the *Geotrichum* genus (e.g. *Geotrichum fermentans*), as well as *Hansenula polymorpha* and *Yarrowia fipolytica*.

The genus *Pichia* is of particular interest. *Pichia* comprises a number of species, including the species *Pichia pastoris*, *Pichia methanolica*, *Pichia kluyveri*, and *Pichia angusta*. Most preferred is the species *Pichia pastoris*.

The former species *Pichia pastoris* has been divided and renamed to *Komagataella pastoris* and *Komagataella phaffii*. Therefore *Pichia pastoris* is synonymous for both *Komagataella pastoris* and *Komagataella phaffii*.

Examples for *Pichia pastoris* strains useful in the present invention are X33 and its subtypes GS115, KM71, KM71H; CB57435 (mut+) and its subtypes CB57435 mut$^s$, CBS7435 mut$^s$□ΔArg, CBS7435 mut$^s$□ΔHis, CBS7435 mut$^s$□ΔArg, ΔHis, CBS7435 mut$^s$ PDI$^+$, CBS 704 (=NRRL Y-1603=DSMZ 70382), CBS 2612 (=NRRL Y-7556), CBS 9173-9189 and DSMZ 70877 as well as mutants thereof.

Examples of *E. coli* include those derived from *Escherichia coli* K12 strain, specifically, HMS 174, HMS174 (DE3), NM533, XL1-Blue, C600, DH1, HB101, JM109, as well as those derived from B-strains, specifically BL-21, BL21 (DE3) and the like.

According a further preferred embodiment, the host cell is a *Pichia pastoris*, *Hansenula polymorpha*, *Trichoderma reesei*, *Saccharomyces cerevisiae*, *Kluyveromyces lactis*, *Yarrowia lipolytica*, *Pichia methanolica*, *Candida boidinii*, and *Komagataella*, and *Schizosaccharomyces pombe*. It may also be a host cell from *Ustilago maydis*.

Preferably, the helper proteins expressed by the host cell is from the same cell or recombined from a cell of the same species, genus or family. As used herein, "recombinant" refers to the alteration of genetic material by human intervention. Typically, recombinant refers to the manipulation of DNA or RNA in a virus, cell, plasmid or vector by molecular biology (recombinant DNA technology) methods, including cloning and recombination. A recombinant cell, polypeptide, or nucleic acid can be typically described with reference to how it differs from a naturally occurring counterpart (the "wild-type"). A "recombinant cell" or "recombinant host cell" refers to a cell or host cell that has been genetically altered to comprise a nucleic acid sequence which was not native to said cell.

The term "manufacture" or "manufacturing" as used presently refers to the process in which the protein of interest is expressed. A "host cell for manufacturing a protein of interest" refers to a host cell in which nucleic acid sequences encoding a protein of interest may be introduced. The recombinant host cell within the present invention does not necessarily contain the nucleic acid sequences encoding a protein of interest. It is appreciated by a skilled person in the art that the host cells can be provided for inserting desired nucleotide sequences into the host cell, for example, in a kit.

The terms "polypeptide" and "protein" are interchangeably used. The term "polypeptide" refers to a protein or peptide that contains two or more amino acids, typically at least 3, preferably at least 20, more preferred at least 30, such as at least 50 amino acids. Accordingly, a polypeptide comprises an amino acid sequence, and, thus, sometimes a polypeptide comprising an amino acid sequence is referred to herein as a "polypeptide comprising a polypeptide sequence". Thus, herein the term "polypeptide sequence" is interchangeably used with the term "amino acid sequence".

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

In a preferred embodiment, the present invention provides a host cell engineered to underexpress the polynucleotide encoding a KO protein having an amino acid sequence as shown in SEQ ID NO: 10, 11, 12 or a functional homologue thereof, wherein the functional homologue has at least 30% sequence identity to an amino acid sequence as shown in SEQ ID NO: 10, 11 or 12, wherein when the underexpression takes place, the yield of the model protein SDZ-Fab (SEQ ID NO: 25 for heavy chain and SEQ ID NO: 26 for light chain; FIG. 2) and/or HyHEL-Fab (SEQ ID NO: 29 for heavy chain and SEQ ID NO: 30 for light chain; FIG. 2) is increased by at least 10% compared to the host cell prior to engineering.

As used herein, "engineered" host cells are host cells which have been manipulated using genetic engineering, i.e. by human intervention. When a host cell is "engineered to underexpress" a given protein, the host cell is manipulated such that the host cell has no longer the capability to express a KO protein or functional homologue such as a non-engineered host cell with, thereby expression of a given protein, e.g. POI or model protein is increased compared to the host cell under the same condition prior to manipulation.

"Prior to engineering" when used in the context of host cells of the present invention means that such host cells are not engineered such that a polynucleotide encoding a KO protein or functional homologue thereof is underexpressed. Said term thus also means that host cells do not underexpress a polynucleotide encoding a KO protein or functional homologue thereof or are not engineered to underexpress a polynucleotide encoding a KO protein or functional homologue thereof.

The term "underexpression" includes any method that prevents or reduces the functional expression of one or more of KO1, KO2, KO3 or functional homologues thereof. This results in the incapability or reduction to exert its known function. Means of underexpression may include gene silencing (e.g. RNAi genes antisense), knocking-out, altering expression level, altering expression pattern, by mutagenizing the gene sequence, disrupting the sequence, insertions, additions, mutations, modifying expression control sequences, and the like. As mentioned herein, a host cell of the present invention is preferably engineered to underexpress a polynucleotide encoding a protein having an amino acid as defined herein. This includes that, if a host cell may have more than one copy of such a polynucleotide, also the other copies of such a polynucleotide are underexpressed. For example, a host cell of the present invention may not only be haploid, but it may be diploid, tetraploid or even more -ploid. Accordingly, in a preferred embodiment all copies of such a polynucleotide are underexpressed, such as two, three, four, five, six or even more copies.

Method of Underexpression

Preferably, underexpression is achieved by knocking-out the polynucleotide encoding the KO protein in the host cell. A gene can be knocked out by deleting the entire or partial coding sequence. Methods of making gene knockouts are known in the art, e.g., see Kuhn and Wurst (Eds.) Gene Knockout Protocols (Methods in Molecular Biology) Humana Press (Mar. 27, 2009). A gene can also be knocked out by removing part or all of the gene sequence. Alternatively, a gene can be knocked-out or inactivated by the insertion of a nucleotide sequence, such as a resistance gene. Alternatively, a gene can be knocked-out or inactivated by inactivating its promoter.

In an embodiment, underexpression is achieved by disrupting the polynucleotide encoding the gene in the host cell.

A "disruption" is a change in a nucleotide or amino acid sequence, which resulted in the addition, deleting, or substitution of one or more nucleotides or amino acid residues, as compared to the original sequence prior to the disruption.

An "insertion" or "addition" is a change in a nucleic acid or amino acid sequence in which one or more nucleotides or amino acid residues have been added as compared to the original sequence prior to the disruption.

A "deletion" is defined as a change in either nucleotide or amino acid sequence in which one or more nucleotides or amino acid residues, respectively, have been removed (i.e., are absent). A deletion encompasses deletion of the entire sequence, deletion of part of the coding sequence, or deletion of single nucleotides or amino acid residues.

A "substitution" generally refers to replacement of nucleotides or amino acid residues with other nucleotides or amino acid residues. "Substitution" can be performed by site-directed mutation, generation of random mutations, and gapped-duplex approaches (See e.g., U.S. Pat. No. 4,760, 025; Moring et al., Biotech. (1984) 2:646; and Kramer et al., Nucleic Acids Res., (1984) 12:9441). Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, Proc. Natl. Acad. Sci. USA 76: 4949-4955; and Barton et ai, 1990, Nucleic Acids Res. 18: 7349-4966. Site-directed mutagenesis can also be accomplished in vivo by methods known in the art. See, e.g., U.S. Patent Application Publication No. 2004/0171 154; Storici et ai, 2001, Nature Biotechnol. 19: 773-776; Kren et ai, 1998, Nat. Med. 4: 285-290; and Calissano and Macino, 1996, Fungal Genet. Newslett. 43: 15-16. Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, Nature 432: 1050-1054) and similar technologies wherein oligonucleotides are synthesized and assembled upon photo-programmable microfluidic chips. Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241:53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al, 1991, Biochemistry 30: 10832-10837; U.S. Pat. No. 5,223,409; WO 92/06204) and region-directed mutagenesis (Derbyshire et al., 1986, Gene 46: 145; Ner et al., 1988, DNA 7:127). Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide. Semisynthetic gene construction is accomplished by combining aspects of synthetic gene construction, and/or site-directed mutagenesis, and/or random mutagenesis, and/or shuffling. Semisynthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled. Alternatively, homologues can be obtained from a natural source such as by screening cDNA libraries of closely or distantly related microorganisms.

Preferably, disruption results in a frame shift mutation, early stop codon, point mutations of critical residues, translation of a nonsense or otherwise non-functional protein product.

In another embodiment, underexpression is achieved by disrupting the promoter which is operably linked with said polypeptide encoding the KO protein. A promoter directs the transcription of a downstream gene. The promoter is necessary, together with other expression control sequences such as ribosomal binding sites, transcriptional start and stop sequences, translational start and stop sequences, and enhancer or activator sequences, to express a given gene. Therefore, it is also possible to disrupt any of the expression control sequence to hinder the expression of the polypeptide encoding the KO protein.

A nucleic acid is "operably linked" when it is placed into a functional relationship with another nucleic acid sequence on the same nucleic acid molecule. For example, a promoter is operably linked with a coding sequence of a recombinant gene when it is capable of effecting the expression of that coding sequence.

In another embodiment, underexpression is achieved by post-transcriptional gene silencing (PTGS). A technique commonly used in the art, PTGS reduces the expression level of a gene via expression of a heterologous RNA sequence, frequently antisense to the gene requiring disruption (Lechtreck et al., J. Cell Sci (2002). 115:1511-1522; Smith et al., Nature (2000). 407:319-320; Furhmann et al., J. Cell Sci (2001). 114:3857-3863; Rohr et al., Plant J (2004). 40(4):611-21. Post-transcriptional gene silencing is a biological process in which RNA molecules inhibit gene expression, typically by causing the destruction of specific mRNA molecules using small RNAs including microRNA (miRNA), small interfering RNA (siRNA) siRNA, or antisense RNA. Gene silencing can occur either through the blocking of transcription (in the case of gene-binding), the degradation of the mRNA transcript (e.g. by small interfering RNA (siRNA) or RNase-H dependent antisense), or through the blocking of either mRNA translation, pre-mRNA splicing sites, or nuclease cleavage sites used for maturation of other functional RNAs, including miRNA (e.g. by Morpholino oligos or other RNase-H independent antisense). These small RNAs can bind to other specific messenger RNA (mRNA) molecules and decrease their activity, for example by preventing an mRNA from producing a protein. Exemplary siRNA molecules have a length from about 10-50 or more nucleotides. The small RNA molecules comprise at least one strand that has a sequence that is "sufficiently complementary" to a target mRNA sequence to direct target-specific RNA interference (RNAi). Small interfering RNAs can originate from inside the cell or can be exogenously introduced into the cell. Once introduced into the cell, exogenous siRNAs are processed by the RNA-induced silencing complex (RISC). The siRNA is complementary to the target mRNA to be silenced, and the RISC uses the siRNA as a template for locating the target mRNA. After the RISC localizes to the target mRNA, the RNA can be cleaved by a ribonuclease. The strand has a sequence sufficient to trigger the destruction of the target mRNA by the RNAi machinery or process is commonly referred to as an antisense strand in the context of a ds-siRNA molecule. The siRNA molecule can be designed such that every residue is complementary to a residue in the target molecule. PTGS is found in many organisms. For yeast cells, the fission yeast, *Schizosaccharomyces pombe*, has an active RNAi pathway involved in heterochromatin formation and centromeric silencing (Raponi et al., Nucl. Acids Res. (2003) 31(15): 4481-4489). Some budding yeasts, including *Saccharomyces cerevisiae, Candida albicans* and *Kluyveromyces polysporus* were also found to have such RNAi pathway (Bartel et la., Science Express doi: 10.1126/science.1176945, published online 10 Sep. 2009). "Underexpression" can be achieved with any known techniques in the art which lowers gene expression. For example, the promoter which is operably linked with the polypeptide encoding the KO protein can be replaced with another promoter which has lower promoter activity. Promoter activity may be assessed by its transcriptional efficiency. This may be determined directly by measurement of the amount of mRNA transcription from the promoter, e.g. by Northern Blotting, quantitative PCR or indirectly by measurement of the amount of gene product expressed from the promoter.

Underexpression may in another embodiment be achieved by intervening in the folding of the expressed KO protein so that the KO protein is not properly folded to become functional. For example, mutation can be introduced to remove a disulfide bond formation of the KO protein or to disruption the formation of an alpha helices and beta sheets.

Protein of Interest

The term "protein of interest" (POI) as used herein refers to a protein that is produced by means of recombinant technology in a host cell. More specifically, the protein may either be a polypeptide not naturally occurring in the host cell, i.e. a heterologous protein, or else may be native to the host cell, i.e. a homologous protein to the host cell, but is produced, for example, by transformation with a self-replicating vector containing the nucleic acid sequence encoding the POI, or upon integration by recombinant techniques of one or more copies of the nucleic acid sequence encoding the POI into the genome of the host cell, or by recombinant modification of one or more regulatory sequences controlling the expression of the gene encoding the POI, e.g. of the promoter sequence. In general, the proteins of interest referred to herein may be produced by methods of recombinant expression well known to a person skilled in the art.

There is no limitation with respect to the protein of interest (POI). The POI is usually a eukaryotic or prokaryotic polypeptide, variant or derivative thereof. The POI can be any eukaryotic or prokaryotic protein. The protein can be a naturally secreted protein or an intracellular protein, i.e. a protein which is not naturally secreted. The present invention also includes biologically active fragments of proteins. In another embodiment, a POI may be an amino acid chain or present in a complex, such as a dimer, trimer, heterodimer, multimer or oligomer.

The protein of interest may be a protein used as nutritional, dietary, digestive, supplements, such as in food products, feed products, or cosmetic products. The food products may be, for example, bouillon, desserts, cereal bars, confectionery, sports drinks, dietary products or other nutrition products. Preferably, the protein of interest is a food additive.

In another embodiment, the protein of interest may be used in animal feeds. The POI may be a detoxifying enzyme such as a mycotoxin degrading enzyme. A detoxifying enzyme means an enzyme which breaks down a toxin such to reduce its toxicity. Mycotoxins are toxic secondary metabolites produced by fungi that readily colonize crops and are often characterized by the ability to harm crops and cause health problems for people and animals. Mycotoxin degrading enzymes include aflatoxin detoxizyme, zearalenone esterases, zearalenone lactonases, zearalenone hydrolase, fumonisin carboxylesterases, fumonisin aminotransferases, aminopolyol amine oxidases, deoxynivalenol epoxide hydrolases. The POI may also be an enzyme which degrades ochratoxin derivatives or ergot alkaloid. Ochratoxins are a group of mycotoxins produced as secondary metabolites by several fungi of the *Aspergillus* or *Penicillium* families and are weak organic acids consisting of a derivative of an isocoumarin. There are three generally recognized ochratoxins, designated A, B and C. Ochratoxin A is the most abundant member of the ochratoxin family and hence the most commonly detected, but is also the most toxic. Ochratoxin A (ochratoxin A) is a nephrotoxic, teratogenic, hepatotoxic, and carcinogenic mycotoxin present in cereals and other starch rich foods. Ergot alkaloids are compounds containing amide bonds and include, for example, ergocornine, ergocorninine, ergocristine, ergocristinine, ergocryptine, ergocryptinine, ergometrine, ergosine, ergotamine and ergotaminine. These compounds are toxic to living organisms including humans and farm animals. Examples of such enzymes include ochratoxin amidase, ergotamine hydrolase, ergotamine amylase. Mycotoxin degrading enzymes in animal feed is useful in controlling mycotoxin contamination of feed.

Further examples of POI include anti-microbial proteins, such as lactoferrin, lysozyme, lactoferricin, lactohedrin, kappa-casein, haptocorrin, lactoperoxidase, a milk protein, acute-phase proteins, e.g., proteins that are produced normally in production animals in response to infection, and small anti-microbial proteins such as lysozyme and lactoferrin. Other examples include bactericidal protein, antiviral proteins, acute phase proteins (induced in production animals in response to infection), probiotic proteins, bacteriostatic protein, and cationic antimicrobial proteins.

"Feed" means any natural or artificial diet, meal or the like or components of such meals intended or suitable for being eaten, taken in, digested, by a non-human animal. A "feed additive" generally refers to substances added in a feed. It typically include one or more compounds such as vitamins, minerals, enzymes and suitable carriers and/or excipient. For the present invention, a food additive may be an enzyme or other proteins. Examples of enzymes which can be used as feed additive include phytase, xylanase and β-glucanase. A "food" means any natural or artificial diet meal or the like or components of such meals intended or suitable for being eaten, taken in, digested, by a human being.

A "food additive" is generally refers to substances added in a food. It typically includes one or more compounds such as vitamins, minerals, enzymes and suitable carriers and/or excipient. For the present invention, a food additive may be an enzyme or other proteins. Examples of enzymes which can be used as food additive include protease, lipase, lactase, pectin methyl esterase, pectinase, transglutaminase, amylase, β-glucanase, acetolactate decarboxylase and laccase.

In some embodiments, the food additive is an anti-microbial protein, which includes, for example, (i) anti-microbial milk proteins (either human or non-human) lactoferrin, lysozyme, lactoferricin, lactohedrin, kappa-casein, haptocorrin, lactoperoxidase, alpha-1-antitrypsin, and immunoglobulins, e.g., IgA, (ii) acute-phase proteins, such as C-reactive protein (CRP); lactoferrin; lysozyme; serum amyloid A (SAA); ferritin; haptoglobin (Hp); complements 2-9, in particular complement-3; seromucoid; ceruloplasmin (Cp); 15-keto-13,14-dihydro-prostaglandin F2 alpha (PGFM); fibrinogen (Fb); alpha(1)-acid glycoprotein (AGP); alpha(1)-antitrypsin; mannose binding protein; lipoplysaccharide binding protein; alpha-2 macroglobulin and various defensins, (iii) antimicrobial peptides, such as cecropin, magainin, defensins, tachyplesin, parasin I.buforin I, PMAP-23, moronecidin, anoplin, gambicin, and SAMP-29, and (iv) other anti-microbial protein(s), including CAP37, granulysin, secretory leukocyte protease inhibitor, CAP18, ubiquicidin, bovine antimicrobial protein-1, Ace-AMP1, tachyplesin, big defensin, Ac-AMP2, Ah-AMP1, and CAP18.

A POI may be an enzyme. Preferred enzymes are those which can be used for industrial application, such as in the manufacturing of a detergent, starch, fuel, textile, pulp and paper, oil, personal care products, or such as for baking, organic synthesis, and the like. Examples of such enzymes include protease, amylase, lipase, mannanase and cellulose for stain removal and cleaning; pullulanase amylase and amyloglucosidase for starch liquefaction and saccharification; glucose isomerase for glucose to fructose conversion; cyclodextrin-glycosyltransferase for cyclodextrin production; xylanase for xiscosity reduction in fuel and starch; amylase, xylanase, lipase, phospholipase, glucose, oxidase, lipoxygenase, transglutaminase for dough stability and conditioning in baking; cellulase in textile manufacturing for denim finishing and cotton softening; amylase for de-sizing of texile; pectate lyase for scouring; catalase for bleach termination; laccase for bleaching; peroxidase for excess dye removal; lipase, protease, amylase, xylanase, cellulose, in pulp and paper production; lipase for transesterification and phospholipase for de-gumming in fat processing fats and oils; lipase for resolution of chiral alcohols and amides in organic synthesis; acylase for synthesis of semisynthetic penicillin, nitrilase for the synthesis of enantiopure carboxylic acids; protease and lipase for leather production; amyloglucosidase, glucose oxidase, and peroxidase for the making personal care products (see Kirk et al., Current Opinion in Biotechnology (2002) 13:345-351)

Therapeutic Protein

A POI may be a therapeutic protein. A POI may be but is not limited to a protein suitable as a biopharmaceutical substance like an antibody or antibody fragment, growth factor, hormone, enzyme, vaccine, or.

The POI may be a naturally secreted protein or an intracellular protein, i.e. a protein which is not naturally secreted. The present invention also provides for the recombinant production of functional homologues, functional equivalent variants, derivatives and biologically active fragments of naturally secreted or not naturally secreted proteins. Functional homologues are preferably identical with or correspond to and have the functional characteristics of a sequence.

The POI may be structurally similar to the native protein and may be derived from the native protein by addition of one or more amino acids to either or both the C- and N-terminal end or the side-chain of the native protein, substitution of one or more amino acids at one or a number of different sites in the native amino acid sequence, deletion of one or more amino acids at either or both ends of the native protein or at one or several sites in the amino acid sequence, or insertion of one or more amino acids at one or more sites in the native amino acid sequence. Such modifications are well known for several of the proteins mentioned above.

Preferably, the protein of interest is a mammalian polypeptide or even more preferably a human polypeptide. Especially preferred therapeutic proteins, which refer to any polypeptide, protein, protein variant, fusion protein and/or fragment thereof which may be administered to a mammal. It is envisioned but not required that therapeutic protein according to the present invention is heterologous to the cell. Examples of proteins that can be produced by the cell of the present invention are, without limitation, enzymes, regulatory proteins, receptors, peptide hormones, growth factors, cytokines, scaffold binding proteins (e.g. anticalins), structural proteins, lymphokines, adhesion molecules, receptors, membrane or transport proteins, and any other polypeptides that can serve as agonists or antagonists and/or have therapeutic or diagnostic use. Moreover, the proteins of interest may be antigens as used for vaccination, vaccines, antigen-binding proteins, immune stimulatory proteins. It may also be an antigen-binding fragment of an antibody, which can include any suitable antigen-binding antibody fragment known in the art. For example, an antibody fragment may include but not limited to Fv (a molecule comprising the VL and VH), single-chain Fv (scFV) (a molecule comprising the VL and VH connected with by peptide linker), Fab, Fab', F(ab')$_2$, single domain antibody (sdAb) (molecules comprising a single variable domain and 3 CDR), and multivalent presentations thereof. The antibody or fragments thereof may be murine, human, humanized or chimeric antibody or fragments thereof. Examples of therapeutic proteins include an antibody, polyclonal antibody, monoclonal antibody, recombinant antibody, antibody fragments, such as Fab', F(ab')$_2$, Fv, scFv, di-scFvs, bi-scFvs, tandem scFvs, bispecific tandem scFvs, sdAb, nanobodies, V$_H$, and V$_L$, or human antibody, humanized antibody, chimeric antibody, IgA antibody, IgD antibody, IgE antibody, IgG antibody, IgM antibody, intrabody, minibody or monobody.

Such therapeutic proteins include, but are not limited to, insulin, insulin-like growth factor, hGH, tPA, cytokines, e.g. interleukines such as IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN) alpha, IFN beta, IFN gamma, IFN omega or IFN tau, tumor necrosisfactor (TNF) TNF alpha and TNF beta, TRAIL; G-CSF, GM-CSF, M-CSF, MCP-1 and VEGF.

In a preferred embodiment, the protein is an antibody. The term "antibody" is intended to include any polypeptide chain-containing molecular structure with a specific shape that fits to and recognizes an epitope, where one or more non-covalent binding interactions stabilize the complex between the molecular structure and the epitope. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammals, chicken, other avians, etc., are considered to be "antibodies." Numerous antibody coding sequences have been described; and others may be raised by methods well-known in the art.

For example, antibodies or antigen binding fragments may be produced by methods known in the art. Generally, antibody-producing cells are sensitized to the desired antigen or immunogen. The messenger RNA isolated from antibody producing cells is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host cell. When antibody gene synthesis is induced in the transfected host, the heavy and light chain proteins self-assemble to produce active antibodies that can be detected by screening with the antigen or immunogen.

Antibody coding sequences of interest include those encoded by native sequences, as well as nucleic acids that, by virtue of the degeneracy of the genetic code, are not identical in sequence to the disclosed nucleic acids, and variants thereof. Variant polypeptides can include amino acid (aa) substitutions, additions or deletions. The amino acid substitutions can be conservative amino acid substitutions or substitutions to eliminate non-essential amino acids, such as to alter a glycosylation site, or to minimize misfolding by substitution or deletion of one or more cysteine residues that are not necessary for function. Variants can be designed so as to retain or have enhanced biological activity of a particular region of the protein (e.g., a functional domain, catalytic amino acid residues, etc). Variants also include fragments of the polypeptides disclosed herein, particularly biologically active fragments and/or fragments corresponding to functional domains. Techniques for in vitro mutagenesis of cloned genes are known. Also included in the subject invention are polypeptides that have been modified using ordinary molecular biological techniques so as to improve their resistance to proteolytic degradation or to optimize solubility properties or to render them more suitable as a therapeutic agent.

Chimeric antibodies may be made by recombinant means by combining the variable light and heavy chain regions (VK and VH), obtained from antibody producing cells of one species with the constant light and heavy chain regions from another. Typically, chimeric antibodies utilize rodent or rabbit variable regions and human constant regions, in order to produce an antibody with predominantly human domains. The production of such chimeric antibodies is well known in the art, and may be achieved by standard means (as described, e.g., in U.S. Pat. No. 5,624,659).

Humanized antibodies are engineered to contain even more human-like immunoglobulin domains, and incorporate only the complementarity-determining regions of the animal-derived antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287.

In addition to entire immunoglobulins (or their recombinant counterparts), immunoglobulin fragments comprising the epitope binding site (e.g., Fab', F(ab')2, or other fragments) may be synthesized. "Fragment" or minimal immunoglobulins may be designed utilizing recombinant immunoglobulin techniques. For instance "Fv" immunoglobulins for use in the present invention may be produced by synthesizing a variable light chain region and a variable heavy chain region. Combinations of antibodies are also of interest, e.g. diabodies, which comprise two distinct Fv specificities.

Immunoglobulins may be modified post-translationally, e.g. to add chemical linkers, detectable moieties, such as fluorescent dyes, enzymes, substrates, chemiluminescent moieties and the like, or specific binding moieties, such as streptavidin, avidin, or biotin, and the like may be utilized in the methods and compositions of the present invention.

Further examples of therapeutic proteins include blood coagulation factors (VII, VIII, IX), alkaline protease from Fusarium, calcitonin, CD4 receptor darbepoetin, DNase (cystic fibrosis), erythropoetin, eutropin (human growth hormone derivative), follicle stimulating hormone (follitropin), gelatin, glucagon, glucocerebrosidase (Gaucher disease), glucosamylase from *A. niger*, glucose oxidase from *A. niger*, gonadotropin, growth factors (GCSF, GMCSF), growth hormones (somatotropines), hepatitis B vaccine, hirudin, human antibody fragment, human apolipoprotein AI, human calcitonin precursor, human collagenase IV, human epidermal growth factor, human insulin-like growth factor, human interleukin 6, human laminin, human proapolipoprotein AI, human serum albumininsulin, insulin and muteins, insulin, interferon alpha and muteins, interferon beta, interferon gamma (mutein), interleukin 2, luteinization hormone, monoclonal antibody 5T4, mouse collagen, OP-1 (osteogenic, neuroprotective factor), oprelvekin (interleukin 11-agonist), organophosphohydrolase, PDGF-agonist, phytase, platelet derived growth factor (PDGF), recombinant plasminogen-activator G, staphylokinase, stem cell factor, tetanus toxin fragment C, tissue plasminogen-activator, and tumor necrosis factor (see Schmidt, Appl Microbiol Biotechnol (2004) 65:363-372).

Leader Sequence

The protein of interest may be linked with a leader sequence which causes secretion of the POI from the host cell. The presence of such a secretion leader sequence in the expression vector is required when the POI intended for recombinant expression and secretion is a protein which is not naturally secreted and therefore lacks a natural secretion leader sequence, or its nucleotide sequence has been cloned without its natural secretion leader sequence. In general, any secretion leader sequence effective to cause secretion of the POI from the host cell may be used in the present invention. The secretion leader sequence may originate from yeast source, e.g. from yeast α-factor such as MFa of Saccharomyces cerevisiae, or yeast phosphatase, from mammalian or plant source, or others. The selection of the appropriate secretion leader sequence is apparent to a skilled person. Alternatively, the secretion leader sequence can be fused to the nucleotide sequence encoding a POI intended for recombinant expression by conventional cloning techniques known to a skilled person prior to cloning of the nucleotide sequence in the expression vector or the nucleotide sequence encoding a POI comprising a natural secretion leader sequence is cloned in the expression vector. In these cases the presence of a secretion leader sequence in the expression vector is not required.

Promoter

The sequence encoding POI may be operably linked to a promoter. The term "promoter" as used herein refers to a region that facilitates the transcription of a particular gene. A promoter typically increases the amount of recombinant product expressed from a nucleotide sequence as compared to the amount of the expressed recombinant product when no promoter exists. A promoter from one organism can be utilized to enhance recombinant product expression from a sequence that originates from another organism. The promoter can be integrated into a host cell chromosome by homologous recombination using methods known in the art (e.g. Datsenko et al, Proc. Natl. Acad. Sci. U.S.A., 97(12): 6640-6645 (2000)). In addition, one promoter element can increase the amount of products expressed for multiple sequences attached in tandem. Hence, one promoter element can enhance the expression of one or more recombinant products.

The promoter could be an "inducible promoter" or "constitutive promoter." "Inducible promoter" refers to a promoter which can be induced by the presence or absence of certain factors, and "constitutive promoter" refers to an unregulated promoter that allows for continuous transcription of its associated gene or genes.

In a preferred embodiment, the nucleotide sequences encoding the POI is driven by an inducible promoter.

Many inducible promoters are known in the art. Many are described in a review by Gatz, Curr. Op. Biotech., 7: 168 (1996) (see also Gatz, Ann. Rev. Plant. Physiol. Plant Mol. Biol., 48:89 (1997)). Examples include tetracycline repressor system, Lac repressor system, copper-inducible systems, salicylate-inducible systems (such as the PR1 a system), glucocorticoid-inducible (Aoyama et al., 1997), alcohol-inducible systems, e.g., AOX promoters, and ecdysome-inducible systems. Also included are the benzene sulphonamide-inducible (U.S. Pat. No. 5,364,780) and alcohol-inducible (WO 97/06269 and WO 97/06268) inducible systems and glutathione S-transferase promoters.

Suitable promoter sequences for use with yeast host cells are described in Mattanovich et al., Methods Mol. Biol. (2012) 824:329-58 and include glycolytic enzymes like triosephosphate isomerase (TPI), phosphoglycerate kinase (PGK), glyceraldehyde-3-phosphate dehydrogenase (GAPDH or GAP) and variants thereof, lactase (LAC) and galactosidase (GAL), P. pastoris glucose-6-phosphate isomerase promoter (PPGI), the 3-phosphoglycerate kinase promoter (PPGK), the glycerol aldehyde phosphate dehydrogenase promoter (PGAP), translation elongation factor promoter (PTEF), and the promoters of P. pastoris enolase 1 (PENO1), triose phosphate isomerase (PTPI), ribosomal subunit proteins (PRPS2, PRPS7, PRPS31, PRPL1), alcohol oxidase promoter (PAOX) or variants thereof with modified characteristics, the formaldehyde dehydrogenase promoter (PFLD), isocitrate lyase promoter (PICL), alpha-ketoisocaproate decarboxylase promoter (PTHI), the promoters of heat shock protein family members (PSSA1, PHSP90, PKAR2), 6-Phosphogluconate dehydrogenase (PGND1), phosphoglycerate mutase (PGPM1), transketolase (PTKL1), phosphatidylinositol synthase (PPIS1), ferro-O2-oxidoreductase (PFET3), high affinity iron permease (PFTR1), repressible alkaline phosphatase (PPHO8), N-myristoyl transferase (PNMT1), pheromone response transcription factor (PMCM1), ubiquitin (PUBI4), single-stranded DNA endonuclease (PRAD2), the promoter of the major ADP/ATP carrier of the mitochondrial inner membrane (PPET9) (WO2008/128701) and the formate dehydrogenase (FMD) promoter. The GAP promoter, AOX promoter or a promoter derived from GAP or AOX promoter is particularly preferred. AOX promoters can be induced by methanol and are repressed by glucose.

Further examples of suitable promoters include Saccharomyces cerevisiae enolase (ENO-1), Saccharomyces cerevisiae galactokinase (GAL1), Saccharomyces cerevisiae alcohol dehydrogenase/glyceraldehyde-3-phosphate dehydrogenase (ADH1, ADH2/GAP), Saccharomyces cerevisiae triose phosphate isomerase (TPI), Saccharomyces cerevisiae metallothionein (CUP1), and Saccharomyces cerevisiae 3-phosphoglycerate kinase (PGK), and the maltase gene promoter (MAL).

Other useful promoters for yeast host cells are described by Romanos et al, 1992, Yeast 8:423-488.

Suitable promoter sequences for use with E. coli include T7 promoter, T5 promoter, tryptophan (trp) promoter, lactose (lac) promoter, tryptophan/lactose (tac) promoter, lipoprotein (lpp) promoter, and λ phage PL promoter in plasmids.

As shown in the examples, the inventors have discovered that when the genes are underexpressed, the yield of the POI (SDZ-Fab or HyHEL-Fab) by at least 20% compared to the host cell without the underexpression.

In a preferred embodiment, underexpression of KO1 gene increases the yield of the model protein SDZ-Fab or HyHEL-Fab in the host cell by at least 1%, such as at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190 or at least 200% or more, compared to the host cell prior to engineering.

In a preferred embodiment, underexpression of KO2 gene increases the yield of the model protein SDZ-Fab or HyHEL-Fab in the host cell by at least 1%, such as at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190 or at least 200% or more, compared to the host cell prior to engineering.

In a preferred embodiment, underexpression of KO3 gene increases the yield of the model protein SDZ-Fab or HyHEL-Fab in the host cell by at least 1%, such as at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190 or at least 200% or more, compared to the host cell prior to engineering.

It is envisioned that in preferred embodiments, when the host cell are cultured to produce the protein of interest, the cell underexpresses at least one the polynucleotide encoding a KO protein having an amino acid sequence as shown in SEQ ID NO: 10, 11, 12 or a functional homologue thereof, wherein the functional homologue has at least 30% sequence identity to an amino acid sequence as shown in SEQ ID NO: 10, 11 or 12 and expresses the protein of interest.

In a further aspect, the present invention provides the use of the engineered host cell for manufacturing a protein of interest. The host cells can be advantageously used for introducing polynucleotides encoding one or more POI(s), and thereafter can be cultured under suitable conditions to express the POI. Details of such use are described in the later section concerning methods of the present invention.

The POI encoding polynucleotide may be recombined in to the host cell by ligating the relevant genes into a vector, and transforming the host cell with the vectors. More teaching can be found in the following sections of the application.

Generally, proteins of interest can be produced by culturing the host cell in an appropriate medium, isolating the expressed POI from the culture, and purifying it by a method appropriate for the expressed product, in particular to separate the POI from the cell.

In another aspect, the present invention provides a method of increasing the yield of a protein of interest in a host cell, comprising underexpressing at least one polynucleotide encoding a KO protein having an amino acid sequence as shown in SEQ ID NO: 10, 11, 12 or a functional homologue thereof, wherein the functional homologue has at least 30% sequence identity to an amino acid sequence as shown in SEQ ID NO: 10, 11 or 12.

As used herein, the term "increasing the yield of a protein of interest in a host cell" means that the yield of the protein of interest is increased when compared to the same cell expressing the same POI under the same culturing conditions, however, without the underexpression of the knockout protein(s).

As will be appreciated by a skilled person in the art, the underexpression of the present KO protein(s) have been shown to increase product yield of POI. Therefore, for a given host cell which expressed a POI with a level that should be increased, it is possible to apply the present invention by underexpressing the present KO protein(s).

In yet a further aspect, the present invention provides a method of increasing the yield of a protein of interest in a host cell. The method comprises (i) engineering the host cell to underexpress at least one, polynucleotide encoding a KO protein having an amino acid sequence as shown in SEQ ID NO: 10, 11, 12 or a functional homologue thereof, wherein the functional homologue has at least 30% sequence identity to an amino acid sequence as shown in SEQ ID NO: 10, 11 or 12, (ii) recombining in said host cell a heterologous polynucleotide encoding a protein of interest, and (iii) culturing said host cell under suitable conditions to express the protein of interest.

As used herein, the term "recombining" as used herein means that a host cell of the present invention is equipped with a heterologous polynucleotide encoding a protein of interest, i.e., a host cell of the present invention is engineered to contain a heterologous polynucleotide encoding a protein of interest. This can be achieved, e.g., by transformation or transfection or any other suitable technique known in the art for the introduction of a polynucleotide into a host cell.

Procedures used to manipulate polynucleotide sequences, e.g. coding for the POI, the promoter, enhancers, leaders, etc., are well known to persons skilled in the art, e.g. described by J. Sambrook et al., Molecular Cloning: A Laboratory Manual (3rd edition), Cold Spring Harbor Laboratory, Cold Spring Harbor Laboratory Press, New York (2001).

A foreign or target polynucleotide such as the polynucleotides encoding the POI or helper protein can be inserted into the chromosome by various means, e.g., by homologous recombination or by using a hybrid recombinase that specifically targets sequences at the integration sites. The foreign or target polynucleotide described above is typically present in a vector ("inserting vector"). These vectors are typically circular and linearized before used for homologous recombination. As an alternative, the foreign or target polynucleotides may be DNA fragments joined by fusion PCR or synthetically constructed DNA fragments which are then recombined into the host cell. In addition to the homology arms, the vectors may also contain markers suitable for selection or screening, an origin of replication, and other elements Polynucleotides encoding the target sequence may also be present on an expression vector. Such vectors are known in the art and already described above. In expression vectors, a promoter is placed upstream of the gene encoding the heterologous protein and regulates the expression of the gene. Multi-cloning vectors are especially useful due to their multi-cloning site. For expression, a promoter is generally placed upstream of the multi-cloning site. A vector for integration of the polynucleotides encoding the POI may be constructed either by first preparing a DNA construct containing the entire DNA sequence coding for the POI and subsequently inserting this construct into a suitable expression vector, or by sequentially inserting DNA fragments containing genetic information for the individual elements, such as the leader sequence, the target DNA sequence, followed by ligation. As an alternative to restriction and ligation of fragments, recombination methods based on attachment (att) sites and recombination enzymes may be used to insert DNA sequences into a vector. Such methods are described, for example, by Landy (1989) Ann. Rev. Biochem. 58:913-949; and are known to those of skill in the art.

Host cells according to the present invention can be obtained by introducing a vector or plasmid comprising the target polynucleotide sequences into the cells. Techniques for transfecting or transforming eukaryotic cells or transforming prokaryotic cells are well known in the art. These can include lipid vesicle mediated uptake, heat shock mediated uptake, calcium phosphate mediated transfection (calcium phosphate/DNA co-precipitation), viral infection, particularly using modified viruses such as, for example, modified adenoviruses, microinjection and electroporation. For prokaryotic transformation, techniques can include heat shock mediated uptake, bacterial protoplast fusion with intact cells, microinjection and electroporation. Techniques for plant transformation include *Agrobacterium* mediated transfer, such as by *A. tumefaciens*, rapidly propelled tungsten or gold microprojectiles, electroporation, microinjection and polyethylyne glycol mediated uptake. The DNA can be single or double stranded, linear or circular, relaxed or supercoiled DNA. For various techniques for transfecting mammalian cells, see, for example, Keown et al. (1990) Processes in Enzymology 185:527-537.

In a further aspect, the present invention provides a method of manufacturing a protein of interest in a host cell comprising (i) providing a host cell engineered to underexpress at least one polynucleotide encoding a protein having an amino acid sequence as shown in SEQ ID NO: 10, 11, 12 or a functional homologue thereof, wherein the functional homologue has at least 30% sequence identity to an amino acid sequence as shown in SEQ ID NO: 10, 11, 12, wherein said host cell comprises a heterologous polynucleotide encoding a protein of interest; and (ii) culturing the host cell under suitable conditions to express the protein of interest. It is understood that the methods disclosed herein may further include cultivating said recombinant host cells under conditions permitting the expression of the POI. A recombinantly produced POI can then be isolated from the cell or the cell culture medium, depending on the nature of the expression system and the expressed protein, e.g. whether the protein is fused to a signal peptide and whether the protein is soluble or membrane-bound. As will be understood by the skilled artisan, cultivation conditions will vary according to factors that include the type of host cell, in particular the expression vector employed. Signal peptides generally contain a positively charged N-terminus followed by a hydrophobic core, followed by a recognition site for an enzyme known as signal peptidase. This enzyme cleaves the signal peptide from the protein during translocation. The protein is transported from the endoplasmic reticulum to the Golgi apparatus, and then follows one of a number of routes in the secretory pathway, depending on the nature of the protein. The protein may be secreted into the culture medium or may be retained on the cell surface, for example. Certain receptors that comprise extracellular, transmembrane, and cytoplasmic domains are examples of proteins that may be retained on the cell membrane, with only the extracellular domain located outside the cell. The leader sequences of certain secreted proteins comprise peptides that are located C-terminal to the signal peptide and are processed from the mature protein of interest subsequent to cleavage of the signal peptide. Such leaders often are referred to as prepro peptides, wherein the pre region is the signal sequence and the pro region designates the remainder of the leader.

One example is the yeast α-factor leader, which contains a signal peptide (including a C-terminal signal peptidase recognition site AlaLeuAla) followed by a pro region containing a basic amino acid pair LysArg that constitutes a KEX2 protease processing site, immediately followed by a peptide GluAlaGluAla at the C-terminus of the pro region. Processing of this leader involves removal of the signal peptide by signal peptidase, followed by cleavage between the Lys and Arg residues by KEX2 protease. The GluAla-GluAla residues are subsequently removed by a peptidase that is the product of the STE13 gene (Julius et al., Cell (1983) 32:839). The yeast α-factor leader is described in U.S. Pat. No. 4,546,082. Signal peptides derived from proteins naturally secreted by yeast cells have been employed in recombinant expression systems for production of heterologous proteins in yeast. The use of mammalian signal peptides in yeast expression systems also has been reported, although certain of the mammalian signal peptides were not effective in promoting secretion of heterologous proteins in yeast.

The phrase culturing under "suitable conditions such that a desired polypeptide is expressed" refers to maintaining and/or growing microorganisms under conditions (e.g., temperature, pressure, pH, duration, etc.) appropriate or sufficient to obtain the desired compound or to obtain desired polypeptide.

In preferred embodiments the host cell also expresses a helper protein. Helper proteins are described in later sections of the application. Using different promoters and/or copies and/or integration sites for the helper gene(s) and/or the POI(s), the expression of the helper genes can be controlled with respect to time point and strength of induction in relation to the expression of the POI(s). For example, prior to induction of POI expression, the helper protein(s) may be first expressed. This has the advantage that the helper protein(s) are already present at the beginning of POI translation. Alternatively, the helper protein(s) and POI(s) can be induced at the same time.

A host cell according to the invention obtained by transformation with the POI genes may preferably first be cultivated at conditions to grow efficiently to a large cell number without the burden of expressing a heterologous protein. When the cells are prepared for POI expression, suitable cultivation conditions are selected and optimized to produce the POI.

An inducible promoter may be used that becomes activated as soon as an inductive stimulus is applied, to direct transcription of the gene under its control. Under growth conditions with an inductive stimulus, the cells usually grow more slowly than under normal conditions, but since the culture has already grown to a high cell number in the previous stage, the culture system as a whole produces a large amount of the heterologous protein. An inductive stimulus is preferably the addition of an appropriate agents (e.g.: methanol for the AOX-promoter) or the depletion of an appropriate nutrient (e.g., methionine for the MET3-promoter). Also, the addition of ethanol, methylamine, cadmium or copper as well as heat or an osmotic pressure increasing agent can induce the expression.

It is preferred to cultivate the hosts according to the invention in a bioreactor under optimized growth conditions to obtain a cell density of at least 1 g/L, preferably at least 10 g/L cell dry weight, more preferably at least 50 g/L cell dry weight. It is advantageous to achieve such yields of POI not only on a laboratory scale, but also on a pilot or industrial scale.

According to the present invention, due to underexpression of the KO protein, the POI is obtainable in high yields, which can be measured in mg POI/g dry biomass, in the range of 1 to 200, such as 50-200, such as 100-200 in the laboratory, pilot and industrial scale is feasible. The specific yield of a production host according to the invention preferably provides for an increase of at least 1.1 fold, more preferably at least 1.2 fold, at least 1.3 or at least 1.4 fold, in some cases an increase of more than 2 fold can be shown, when compared to the expression of the product without the underexpression of helper proteins.

The host cell according to the invention may be tested for its expression/secretion capacity or yield by standard tests, e.g. ELISA, activity assays, HPLC, Surface Plasmon Resonance (Biacore), Western Blot, capillary electrophoresis (Caliper) or SDS-Page.

Preferably, the cells are cultivated in a mineral medium with a suitable carbon source, thereby further simplifying the isolation process significantly. By way of example, the mineral medium contains an utilizable carbon source (e.g. glucose, glycerol or methanol), salts containing the macro elements (potassium, magnesium, calcium, ammonium, chloride, sulphate, phosphate) and trace elements (copper, iodide, manganese, molybdate, cobalt, zinc, and iron salts, and boric acid).

In the case of yeast cells, the cells may be transformed with one or more of the above-described expression vector(s) or plasmid(s), mated to form diploid strains, and cultured in conventional nutrient media modified as appropriate for inducing promoters, selecting transformants or amplifying the genes encoding the desired sequences. A number of minimal media suitable for the growth of yeast are known in the art. Any of these media may be supplemented as necessary with salts (such as sodium chloride, calcium, magnesium, and phosphate), buffers (such as HEPES, citric acid and phosphate buffer), nucleosides (such as adenosine and thymidine), antibiotics, trace elements, vitamins, and glucose or an equivalent energy source. Any other necessary supplements may also be included at appropriate concentrations that would be known to those skilled in the art. The culture conditions, such as temperature, pH and the like, are those previously used with the host cell selected for expression and are known to the ordinarily skilled artisan. Cell culture conditions for other type of host cells are also known and can be readily determined by the artisan. Descriptions of culture media for various microorganisms are for example contained in the handbook "Manual of Methods for General Bacteriology" of the American Society for Bacteriology (Washington D.C., USA, 1981).

Cells can be cultured (e.g., maintained and/or grown) in liquid media and preferably are cultured, either continuously or intermittently, by conventional culturing methods such as standing culture, test tube culture, shaking culture (e.g., rotary shaking culture, shake flask culture, etc.), aeration spinner culture, or fermentation. In some embodiments, cells are cultured in shake flasks or deep well plates. In yet other embodiments, cells are cultured in a bioreactor (e.g., in a bioreactor cultivation process). Cultivation processes include, but are not limited to, batch, fed-batch and continuous methods of cultivation. The terms "batch process" and "batch cultivation" refer to a closed system in which the composition of media, nutrients, supplemental additives and the like is set at the beginning of the cultivation and not subject to alteration during the cultivation; however, attempts may be made to control such factors as pH and oxygen concentration to prevent excess media acidification and/or cell death. The terms "fed-batch process" and "fed-batch cultivation" refer to a batch cultivation with the exception that one or more substrates or supplements are added (e.g., added in increments or continuously) as the cultivation progresses. The terms "continuous process" and "continuous cultivation" refer to a system in which a defined cultivation media is added continuously to a bioreactor and an equal amount of used or "conditioned" media is simultaneously removed, for example, for recovery of the desired product. A variety of such processes has been developed and is well-known in the art.

In some embodiments, cells are cultured for about 12 to 24 hours, in other embodiments, cells are cultured for about 24 to 36 hours, about 36 to 48 hours, about 48 to 72 hours, about 72 to 96 hours, about 96 to 120 hours, about 120 to 144 hours, or for a duration greater than 144 hours. In yet other embodiments, culturing is continued for a time sufficient to reach desirable production yields of POI.

The above mentioned methods may further comprise a step of isolating the expressed POI. If the POI is secreted from the cells, it can be isolated and purified from the culture medium using state of the art techniques. Secretion of the POI from the cells is generally preferred, since the products are recovered from the culture supernatant rather than from the complex mixture of proteins that results when cells are disrupted to release intracellular proteins. A protease inhibitor, such as phenyl methyl sulfonyl fluoride (PMSF) may be useful to inhibit proteolytic degradation during purification, and antibiotics may be included to prevent the growth of adventitious contaminants. The composition may be concentrated, filtered, dialyzed, etc., using methods known in the art. Alternatively, cultured host cells may also be ruptured sonically or mechanically, enzymatically or chemically to obtain a cell extract containing the desired POI, from which the POI may be isolated and purified.

As isolation and purification methods for obtaining the POI may be based on methods utilizing difference in solubility, such as salting out and solvent precipitation, methods utilizing difference in molecular weight, such as ultrafiltration and gel electrophoresis, methods utilizing difference in electric charge, such as ion-exchange chromatography, methods utilizing specific affinity, such as affinity chromatography, methods utilizing difference in hydrophobicity, such as reverse phase high performance liquid chromatography, and methods utilizing difference in isoelectric point, such as isoelectric focusing may be used. Specific purification steps are preferably employed to remove any helper protein that is also expressed and would contaminate the POI preparation.

The isolated and purified POI can be identified by conventional methods such as Western Blotting or specific assays for its activity. The structure of the purified POI can be defined by amino acid analysis, amino-terminal analysis, primary structure analysis, and the like. It is preferred that the POI is obtainable in large amounts and in a high purity level, thus meeting the necessary requirements for being used as an active ingredient in pharmaceutical compositions or as feed or food additive.

Helper Proteins

The host cell of the present invention may additionally comprise at least one polynucleotide encoding a helper protein. Any helper protein known in the art can be used.

A "helper proteins" as used in the present invention means a protein which enhances the expression and/or secretion of a protein of interest. This term should be understand broadly and should not be limited to chaperons or chaperon-like proteins.

A helper protein may for example be a chaperone. A chaperone generally has the function of binding to and stabilising an otherwise unstable conformer of another protein. By controlled binding and release, a chaperone facilitates its correct fate in vivo, be it folding, oligomeric assembly, transport to a particular subcellular compartment, or disposal by degradation. Chaperone proteins of this type are known in the art, for example in the Stanford Genome Database (SGD), http://db.yeastgenome.org or http://www-.yeastgenome.org. Preferred chaperones are eukaryotic chaperones, especially preferred chaperones are yeast chaperones, including AHA1, CCT2, CCT3, CCT4, CCT5, CCT6, CCT1, CCT8, CNS1, CPR3, CPR6, ERO1, EUG1, FMO1, HSP10, HSP12, HSP104, HSP26, HSP30, HSP42, HSP60, HSP78, HSP82, JEM1, MDJ1, MDJ2, MPD1, MPD2, PDI1, PFD1, ABC1, APJ1, ATP11, ATP12, BTT1, CDC37, CPR7, HSC82, KAR2, LHS1, MGE1, MRS11, NOB1, ECM10, SSA1, SSA2, SSA3, SSA4, SSC1, SSE2, SIL1, SLS1, ORM1, ORM2, PERI, PTC2, PSE1, UBI4 and HAC1 or a truncated intronless HAC1 (Valkonen et al. 2003, Applied Environ Micro., 69, 2065), as well as TIM9, PAM18 (also known as TIM14) and TCP1 (also known as CCT1). For example, the host cell may comprise a polynucleotide encoding BMH2, BFR2, COG6, COY1, CUP5, IMH1, KIN2, SEC31, SSA4, SSE1 or KAR2 (WO2008128701).

The helper proteins may be native to the species or the genus of the host cell or taken or derived from other prokaryotic or eukaryotic organisms. The foreign DNA sequences encoding the helper proteins may be obtained from a variety of sources, preferably from a plant, insect, fungal or mammalian species, preferably from the class of Saccharomycetes, preferably from the order of Saccharomycetales, preferably from the family of Saccharomycetaceae, and preferably from the genus of *Komagataella*. Homologous nucleotide sequences from other organisms such as vertebrates may be used.

The amino acid sequences of each helper proteins and their corresponding designations in the Examples are listed in Table 2 below:

TABLE 2

| Helper protein (HP) and alternative designation ('xx') | Designation (in analogy to S. cerevisiae) | Amino acid sequences (SEQ ID NO:) | Polynucleotide (SEQ ID NO:) | Designation in the Examples (see Table 7) |
| --- | --- | --- | --- | --- |
| HP1 ('56') |  | SEQ ID NO: 4 | SEQ ID NO: 16 | PP7435_Chr3-0607 |
| HP2 ('2') |  | SEQ ID NO: 1 | SEQ ID NO: 13 | PP7435_Chr3-0933 |
| HP3 ('3') | SBH1 | SEQ ID NO: 2 | SEQ ID NO: 14 | PP7435_Chr2-0220 |
| HP4 ('27') | CPR6 | SEQ ID NO: 3 | SEQ ID NO: 15 | PP7435_Chr3-0639 |
| HP5 ('4') | MXR2 | SEQ ID NO: 5 | SEQ ID NO: 17 | PP7435_Chr4-0108 |
| HP6 ('54') | MDR1 | SEQ ID NO: 7 | SEQ ID NO: 19 | PP7435_Chr1-1225 |
| HP7 ('55') |  | SEQ ID NO: 8 | SEQ ID NO: 20 | PP7435_Chr1-0667 |
| HP8 ('40') | — | SEQ ID NO: 6 | SEQ ID NO: 18 | PP7435_Chr1-1232 |
| HP9 ('60') | — | SEQ ID NO: 9 | SEQ ID NO: 21 | PP7435_Chr4-0448 |
| HP10 ('34') | SEC61 | SEQ ID NO: 162 | SEQ ID NO: 163 | PP7435_Chr1-0204 |

Preferably, the host cell comprises at least one polynucleotide encoding a helper protein of the present invention, namely, HP1, HP2, HP3, HP4, HP5, HP6, HP7, HP8, HP9, HP10 or functional homologues thereof. A helper protein of the present invention comprises the amino acid sequences of SEQ ID NO: 1, 2, 3, 4, 5, 6, 7, 8, 9, or 162 and functional homologues thereof. A helper protein of the present invention can be encoded by the nucleotide sequences of SEQ ID NO: 13, 14, 15, 16, 17, 18, 19, 20, 21, or 163. Thus, the term "helper protein" when used in the context of HP1-HP10 is meant to encompass HP1, HP2, HP3, HP4, HP5, HP6, HP7, HP8, HP9 and HP 10 as well as functional homologues of HP1, HP2, HP3, HP4, HP5, HP6, HP7, HP8, HP9, and HP10, respectively.

As used herein, such helper protein has an amino acid sequence having at least 30%, such as at least 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, sequence identity to an amino acid sequence as shown in SEQ ID NO: 1, 2, 3, 4, 5, 6, 7, 8, 9, or 162. The amino acid sequences of the helper proteins HP1 to HP10 are listed in SEQ ID NO: 1, 2, 3, 4, 5, 6, 7, 8, 9, or 162.

The helper proteins of the present invention were originally isolated from *Pichia pastoris* CBS7435 strain. The methylotrophic yeast *Pichia pastoris* (*Komagataella phaffii*) CBS7435 is the parental strain of commonly used *P. pastoris* recombinant protein production hosts. Its complete genomic sequence is described in Küberl et al. (J Biotechnol. (2011) 154(4):312-20). These genes encoding the helper proteins identified herein have so far not been associated with a beneficial effect on protein yield.

In particular, out of a screen for secretion helper factors in *Pichia pastoris* 55 candidate genes were identified which were validated by wet-lab expression experiments in order to select prime candidate genes. A prime candidate gene is one which enhances yield of the two model proteins SDZ-Fab # 9 and/or HyHEL-Fab # 8 as described herein to an extent of 20% or more in comparison to a *P. pastoris* strain not over-expressing the prime candidate gene, i.e., a host cell prior to engineering as described herein. To this end, out of the 55 genes, 9 prime candidates were identified. 4 prime candidates, i.e. PP7435_Chr3-0607, PP7435_Chr3-0933, PP7435_Chr2-0220 (SBH1), PP7435_Chr3-0639 (CPR6) showed more than 20% secretion and/or expression enhancement of both model proteins SDZ-Fab and HyHEL Fab and 5 further candidates (PP7435_Chr4-0108 (MXR2), PP7435_Chr1-1232, PP7435_Chr1-1225 (MDR1), PP7435_Chr1-0667, PP7435_Chr4-0448) showed >20-30% secretion yield enhancement for one of the two model proteins SDZ-Fab and HyHEL Fab, respectively, when being overexpressed.

Basis for the screen was a direct comparison between the transcriptional profile of a *P. pastoris* producer strain and a *P. pastoris* non-producer strain which resulted in the identification of 55 genes. These genes belong to various metabolic pathways and have different functions or may even have an unknown function. Thus, no guidance as to the nature of the thus-obtained helper factors is apparent from the genes or proteins encoded thereby. Accordingly, tests have to be performed in order to validate whether or not a potential secretion helper factor is indeed a helper factor under real conditions. However, it is prima facie not apparent that a potential helper factor is indeed a helper factor, merely because it was identified by its enhanced transcript appearance in a producer strain. In fact, it may be that a potential helper factor has no positive effect on protein secretion or may even have a negative effect. This was indeed observed by the inventors, since two genes encoding chaperones (SCJ1, HCH1) identified among the 55 genes, from which it could be reasonably expected to enhance secretion, did the opposite. Thus, tests for each gene are required, but no guidance exists as to which protein encoded by one of the approx. 60 genes is indeed a secretion helper factor.

Hence, the finding of a "true" secretion helper factor is not a straightforward matter, but an inventive choice for which no guidance is available or apparent from the mere gene/protein sequence or the function of a protein identified in a screen as done by the present inventors.

What is also unusual about the prime candidate genes that have to be overexpressed as is described herein—they are not typical secretion helper factors, i.e., genes which encode a protein having a function that is not deemed to play a role in protein secretion or even have an unknown function.

In a preferred embodiment, the host cell is further engineered to express or overexpress at least one, such as at least 2, 3, 4, 5, 6, 7, 8, or at least 9 polynucleotide encoding a helper protein having an amino acid sequence as shown in SEQ ID NO: 1, 2, 3, 4, 5, 6, 7, 8, 9, or 162 or a functional homologue thereof, wherein the functional homologue has having at least 30% sequence identity to an amino acid sequence as shown in SEQ ID NO: 1, 2, 3, 4, 5, 6, 7, 8, 9, or 162.

Preferably, the present invention provides a recombinant host cell for manufacturing a protein of interest, wherein the host cell is engineered to overexpress a polynucleotide encoding a helper protein having an amino acid having at least 40% sequence identity to SEQ ID NO: 1, 45% sequence identity to SEQ ID NO: 2, 50% sequence identity to SEQ ID NO: 3, 45% sequence identity to SEQ ID NO: 4, 50% sequence identity to SEQ ID NO: 5, 45% sequence identity to SEQ ID NO: 6, 40% sequence identity to SEQ ID NO: 7, 40% sequence identity to SEQ ID NO: 8, 40% sequence identity to SEQ ID NO: 9, or 45% sequence identity to SEQ ID NO: 162. Such a host cell is applied in the methods and uses described herein.

Preferably, the host cell is engineered to express or overexpress at least one polynucleotide encoding a helper protein having an amino acid sequence having at least 30% sequence identity to an amino acid sequence as shown in SEQ ID NO: 1, 2, 3, 4, 5, 6, 7, 8, 9, or 162. If the polynucleotide(s) already exist in the host cell, the host cell can manipulated in a way such that they are overexpressed, as will be described later.

In a preferred embodiment, 2, 3, 4, 5, 6, 7, 8 9 or more types of helper proteins disclosed by present invention are overexpressed. For example, the host cell can be engineered to overexpress 2, 3, 4, 5, 6, 7, 8 or more of helper proteins selected from SEQ ID NO: 1, 2, 3, 4, 5, 6, 7, 8, 9, or 162 or functional homologues thereof, where a functional homologue thereof has an amino acid having at least 30% sequence identity to SEQ ID NO: 1, 2, 3, 4, 5, 6, 7, 8, 9, or 162.

The term "overexpress" generally refers to any amount greater than or equal to an expression level exhibited by a reference standard. The terms "overexpress," "overexpressing," "overexpressed" and "overexpression" in the present invention refer an expression of a gene product or a polypeptide at a level greater than the expression of the same gene product or polypeptide prior to a genetic alteration of the host cell or in a comparable host which has not been genetically altered at defined conditions. If a host cell does not comprise a given gene product, it is possible to introduce the gene product into the host cell for expression; in this case, any detectable expression is encompassed by the term "overexpression." However, it is not required, although preferred, that the host cell overexpresses the helper protein HP1-HP10 or functional homologues thereof.

Overexpression of Helper Proteins by the Host Cell

Overexpression can be achieved in any ways known to a skilled person in the art. In general, it can be achieved by increasing transcription/translation of the gene, e.g. by increasing the copy number of the gene or altering or modifying regulatory sequences or sites associated with expression of a gene. For example, the gene can be operably linked to a strong constitutive promoter and/or strong ubiquitous promoter in order to reach high expression levels. Such promoters can be endogenous promoters or recombinant promoters. Alternatively, it is possible to remove regulatory sequences such that expression becomes constitutive. One can substitute a promoter with a heterologous promoter which increases expression of the gene or leads to constitutive expression of the gene. Using inducible promoters additionally makes it possible to increase the expression in the course of cultivation. Furthermore, overexpression can also be achieved by, for example, modifying the chromosomal location of a particular gene, altering nucleic acid sequences adjacent to a particular gene such as a ribosome binding site or transcription terminator, introducing a frameshift in the open reading frame, modifying proteins (e.g., regulatory proteins, suppressors, enhancers, transcriptional activators and the like) involved in transcription of the gene and/or translation of the gene product, or any other conventional means of deregulating expression of a particular gene routine in the art (including but not limited to use of antisense nucleic acid molecules, for example, to block expression of repressor proteins or deleting or mutating the gene for a transcriptional factor which normally represses expression of the gene desired to be overexpressed. Prolonging the life of the mRNA may also improve the level of expression. For example, certain terminator regions may be used to extend the half-lives of mRNA (Yamanishi et al., Biosci. Biotechnol. Biochem. (2011) 75:2234 and US 2013/0244243). If multiple copies of genes are included, the genes can either be located in plasmids of variable copy number or integrated and amplified in the chromosome. If the host cell does not comprise the gene product encoding the helper protein, it is possible to introduce the gene product into the host cell for expression. In this case, "overexpression" means expressing the gene product using any methods known to a skilled person in the art.

The overexpression of the polypeptide encoding the helper proteins, can be achieved by other methods known in the art, for example by genetically modifying their endogenous regulatory regions, as described by Marx et al., 2008 (Marx, H., Mattanovich, D. and Sauer, M. *Microb Cell Fact* 7 (2008): 23), and Pan et al., 2011 (Pan et al., *FEMS Yeast Res*. (2011) May; (3):292-8.), such methods include, for example, integration of a recombinant promoter that increases expression of the helper proteins. Transformation is described in Cregg et al. (1985) Mol. Cell. Biol. 5:3376-3385.

Those skilled in the art will find relevant instructions in Martin et al. (Bio/Technology 5, 137-146 (1987)), Guerrero et al. (Gene 138, 35-41 (1994)), Tsuchiya and Morinaga (Bio/Technology 6, 428-430 (1988)), Eikmanns et al. (Gene 102, 93-98 (1991)), EP 0 472 869, U.S. Pat. No. 4,601,893, Schwarzer and Puhler (Bio/Technology 9, 84-87 (1991)), Reinscheid et al. (Applied and Environmental Microbiology 60, 126-132 (1994)), LaBarre et al. (Journal of Bacteriology 175, 1001-1007 (1993)), WO 96/15246, Malumbres et al. (Gene 134, 15-24 (1993)), JP-A-10-229891, Jensen and Hammer (Biotechnology and Bioengineering 58, 191-195 (1998)) and Makrides (Microbiological Reviews 60, 512-538 (1996)), inter alia, and in well-known textbooks on genetics and molecular biology.

According to a preferred embodiment, the polynucleotide encoding the helper protein can be presented in a single copy or in multiple copies per cell. The copies may be adjacent to or distant from each other. According to another preferred embodiment, the method of the invention employs recombinant nucleotide sequences encoding the helper proteins provided on one or more plasmids suitable for integration into the genome of the host cell, in a single copy or in multiple copies per cell. The copies may be adjacent to or distant from each other. Overexpression can be achieved by expressing multiple copies of the polynucleotide, such as 2, 3, 4, 5, 6 or more copies of said polynucleotide per host cell.

The recombinant nucleotide sequence encoding the POI(s), as well as those encoding the helper proteins, may also be provided on one or more autonomously replicating plasmids in a single copy or in multiple copies per cell.

Alternatively, the recombinant nucleotide sequence encoding the POI and the recombinant nucleotide sequence encoding a protein that increases protein secretion are present on the same plasmid in single copy or multiple copies per cell.

The polynucleotide encoding the helper protein is preferably integrated into the genome of the host cell. The term "genome" generally refers to the whole hereditary information of an organism that is encoded in the DNA (or RNA for certain viral species). It may be present in the chromosome, on a plasmid or vector, or both. Preferably, the polynucleotide encoding the helper protein is integrated into the chromosome of said cell.

The polynucleotide encoding the helper protein may be integrated in its natural locus. "Natural locus" means the location on a specific chromosome, where the polynucleotide encoding the helper protein is located, for example at the natural locus of HP1 to 9 as shown in Table 1. However, in another embodiment, the polynucleotide encoding the helper protein is present in the genome of the host cell not at their natural locus, but integrated ectopically. The term "ectopic integration" means the insertion of a nucleic acid into the genome of a microorganism at a site other than its usual chromosomal locus, i.e., predetermined or random integration. In another embodiment, the polynucleotide encoding the helper protein is integrated into the natural locus and ectopically. Heterologous recombination can be used to achieve random or non-targeted integration. Heterologous recombination refers to recombination between DNA molecules with significantly different sequences. Methods of recombinations are known in the art and for example described in Boer et al., Appl Microbiol Biotechnol (2007) 77:513-523. One may also refer to Principles of Gene Manipulation and Genomics by Primrose and Twyman (7th edition, Blackwell Publishing 2006) for genetic manipulation of yeast cells.

For yeast cells, the polynucleotide encoding the helper protein and/or the polynucleotide encoding the POI may be inserted into a desired locus, such as AOX1, GAP, ENO1, TEF, HIS4 (Zamir et al., Proc. NatL Acad. Sci. USA (1981) 78(6):3496-3500), HO (Voth et al. Nucleic Acids Res. 2001 Jun. 15; 29(12): e59), TYR1 (Mirisola et al., Yeast 2007; 24: 761-766), His3, Leu2, Ura3 (Taxis et al., BioTechniques (2006) 40:73-78), Lys2, ADE2, TRP1, GAL1, ADH1 or on the integration of 5S ribosomal RNA gene.

In other embodiments, the polynucleotide encoding the helper protein and/or the polynucleotide encoding the POI can be integrated in a plasmid or vector. The terms "plasmid" and "vector" include autonomously replicating nucleotide sequences as well as genome integrating nucleotide sequences. A skilled person is able to employ suitable plasmids or vectors depending on the host cell used.

Preferably, the plasmid is a eukaryotic expression vector, preferably a yeast expression vector.

Preferably, the plasmid is a eukaryotic expression vector, preferably a yeast expression vector. Examples of plasmids using yeast as a host include YIp type vector, YEp type vector, YRp type vector, YCp type vector, pGPD-2, pAO815, pGAPZ, pGAPZα, pHIL-D2, pHIL-S1, pPIC3.5K, pPIC9K, pPICZ, pPICZα, pPIC3K, pHWO10, pPUZZLE and 2 μm plasmids. Such vectors are known and are for example described in Cregg et al., Mol Biotechnol. (2000) 16(1):23-52.

Plasmids can be used for the transcription of cloned recombinant nucleotide sequences, i.e. of recombinant genes and the translation of their mRNA in a suitable host organism. Plasmids can also be used to integrate a target polynucleotide into the host cell genome by methods known in the art, such as described by J. Sambrook et al., Molecular Cloning: A Laboratory Manual (3rd edition), Cold Spring Harbor Laboratory, Cold Spring Harbor Laboratory Press, New York (2001). A "plasmid" usually comprises an origin for autonomous replication in the host cells, selectable markers, a number of restriction enzyme cleavage sites, a suitable promoter sequence and a transcription terminator, which components are operably linked together. The polypeptide coding sequence of interest is operably linked to transcriptional and translational regulatory sequences that provide for expression of the polypeptide in the host cells.

Most plasmids exist in only one copy per bacterial cell. Some plasmids, however, exist in higher copy numbers. For example, the plasmid ColE1 typically exists in 10 to 20 plasmid copies per chromosome in E. coli. If the nucleotide sequences of the present invention are contained in a plasmid, the plasmid may have a copy number of 20-30, 30-100 or more per host cell. With a high copy number of plasmids, it is possible to overexpress helper proteins by the cell.

Large numbers of suitable plasmids or vectors are known to those of skill in the art and many are commercially available. Examples of suitable vectors are provided in Sambrook et al, eds., Molecular Cloning: A Laboratory Manual (2nd Ed.), Vols. 1-3, Cold Spring Harbor Laboratory (1989), and Ausubel et al, eds., Current Protocols in Molecular Biology, John Wiley & Sons, Inc., New York (1997).

A vector or plasmid of the present invention encompass yeast artificial chromosome, which refers to a DNA construct that can be genetically modified to contain a heterologous DNA sequence (e.g., a DNA sequence as large as 3000 kb), that contains telomeric, centromeric, and origin of replication (replication origin) sequences.

A vector or plasmid of the present invention also encompasses bacterial artificial chromosome (BAC), which refers to a DNA construct that can be genetically modified to contain a heterologous DNA sequence (e.g., a DNA sequence as large as 300 kb), that contains an origin of replication sequence (Ori), and may contain one or more helicases (e.g., parA, parB, and parC).

Examples of plasmids using Escherichia coli as their host include pBR322, pUC18, pUC19, pUC118, pVC119, pSP64, pSP65, pTZ-18R/-18U, pTZ-19R/-19U, pGEM-3, pGEM-4, pGEM-3Z, pGEM-4Z, pGEM-5Zf(−), and pBluescript KSTM (Stratagene). Examples of plasmids suitable for expression in *Escherichia coli* include pAS, pKK223 (Pharmacia), pMC1403, pMC931, and pKC30.

Polynucleotides encoding the helper proteins and the POI may be recombined in to the host cell by ligating the relevant genes each into one vector. It is possible to construct single vectors carrying the genes, or two separate vectors, one to carry the helper protein genes and the other one the POI genes. These genes can be integrated into the host cell genome by transforming the host cell using such vector or vectors. In some embodiments, the genes encoding the POI is integrated in the genome and the gene encoding the helper protein is integrated in a plasmid or vector. In some embodiments, the genes encoding the helper protein is integrated in the genome and the gene encoding the POI is integrated in a plasmid or vector. In some embodiments, the genes encoding the POI and the helper protein are integrated in the genome. In some embodiments, the gene encoding the POI and the helper protein is integrated in a plasmid or vector. If multiple genes encoding the POI are used, some genes encoding the POI are integrated in the genome while others are integrated in the same or different plasmids or vectors. If multiple genes encoding the helper proteins are used, some of the genes encoding the helper protein are integrated in the genome while others are integrated in the same or different plasmids or vectors.

Overexpression of the endogenous polypeptide in the recombinant microbial cell can be achieved by modifying expression control sequences. Expression control sequences are known in the art and include, for example, promoters, enhancers, polyadenylation signals, transcription terminators, internal ribosome entry sites (IRES), and the like, that provide for the expression of the polynucleotide sequence in a host cell. Expression control sequences interact specifically with cellular proteins involved in transcription (Maniatis et al., Science, 236: 1237-1245 (1987)). Exemplary expression control sequences are described in, for example, Goeddel, Gene Expression Technology: Methods in Enzymology, Vol. 185, Academic Press, San Diego, Calif. (1990).

In a preferred embodiment, the overexpression is achieved by using an enhancer to express the helper protein. Transcriptional enhancers are relatively orientation and position independent, having been found 5' and 3' to the transcription unit, within an intron, as well as within the coding sequence itself. The enhancer may be spliced into the expression vector at a position 5' or 3' to the coding sequence, but is preferably located at a site 5' from the promoter. Most yeast genes contain only one UAS, which generally lies within a few hundred base pairs of the cap site and most yeast enhancers (UASs) cannot function when located 3' of the promoter, but enhancers in higher eukaryotes can function both 5' and 3' of the promoter.

Many enhancer sequences are now known from mammalian genes (globin, RSV, SV40, EMC, elastase, albumin, a-fetoprotein and insulin). One may also use an enhancer from a eukaryotic cell virus, such as the SV40 late enhancer, the cytomegalovirus early promoter enhancer, the polyoma enhancer on the late side of the replication origin, and adenovirus enhancers. Yeast enhancers, also called upstream activating sequences (UASs), such as the UAS/Gal system from *Saccharomyces cerevisiae*, can be advantageously used with yeast promoters (described in European Patent No. 0317254 and Rudoni et al., The International Journal of Biochemistry and Cell Biology, (2000), 32(2):215-224).

Overexpression of the endogenous polypeptide in the recombinant cell can be achieved by modifying transcriptional and translational regulatory sequences, including, for example, promoters, enhancers, polyadenylation signals, transcription terminators, internal ribosome entry sites (IRES), and the like, that provide for the expression of the polynucleotide sequence in a host cell. Such sequences interact specifically with cellular proteins involved in transcription (Maniatis et al., Science, 236: 1237-1245 (1987)). Exemplary sequences are described in, for example, Goeddel, Gene Expression Technology: Methods in Enzymology, Vol. 185, Academic Press, San Diego, Calif. (1990). The polynucleotides encoding the POI and/or helper proteins are preferably operably linked to transcriptional and translational regulatory sequences that provide for expression in the host cells. The term "transcriptional regulatory sequences" as used herein refers to nucleotide sequences that are associated with a gene nucleic acid sequence and which regulate the transcription of the gene. The term "translational regulatory sequences" as used herein refers to nucleotide sequences that are associated with a gene nucleic acid sequence and which regulate the translation of the gene. Transcriptional and/or translational regulatory sequences can either be located in plasmids or vectors or integrated in the chromosome of the host cell. Transcriptional and/or translational regulatory sequences are located in the same nucleic acid molecule of the gene which it regulates.

For example, overexpression of the endogenous helper protein in the recombinant cell can be achieved by modifying the promoters, for example, by replacing the endogenous promoter which is operably linked to the helper protein with another stronger promoter in order to reach high expression levels. Such promoter may be inductive or constitutive. Modification of endogenous promoter may be performed by mutation or homologous recombination using methods known in the art.

The overexpression of the polynucleotide encoding the helper proteins, can be achieved by other methods known in the art, for example by genetically modifying their endogenous regulatory regions, as described by Marx et al., 2008 (Marx, H., Mattanovich, D. and Sauer, *M. Microb Cell Fact* 7 (2008): 23), and Pan et al., 2011 (Pan et al., *FEMS Yeast Res.* (2011) May; (3):292-8.), such methods include, for example, integration of a recombinant promoter that increases expression of the helper proteins. Transformation is described in Cregg et al. (1985) Mol. Cell. Biol. 5:3376-3385. A "recombinant" promoter is referred to with respect to the sequence whose expression it drives. As used herein, a recombinant promoter means when the promoter is not a native promoter to the given sequence, i.e., when the promoter is different from a naturally occurring promoter (the "native promoter"). The term "promoter" as used herein refers to a region that facilitates the transcription of a particular gene. A promoter typically increases the amount of recombinant product expressed from a nucleotide sequence as compared to the amount of the expressed recombinant product when no promoter exists. A promoter from one organism can be utilized to enhance recombinant product expression from a sequence that originates from another organism. The promoter can be integrated into a host cell chromosome by homologous recombination using methods known in the art (e.g. Datsenko et al, Proc. Natl. Acad. Sci. U.S.A., 97(12): 6640-6645 (2000)). In addition, one promoter element can increase the amount of products expressed for multiple sequences attached in tandem. Hence, one promoter element can enhance the expression of one or more recombinant products.

Promoter activity may be assessed by its transcriptional efficiency. This may be determined directly by measurement of the amount of mRNA transcription from the promoter, e.g. by Northern Blotting, quantitative PCR or indirectly by measurement of the amount of gene product expressed from the promoter.

The promoter could be an "inducible promoter" or "constitutive promoter." "Inducible promoter" refers to a promoter which can be induced by the presence or absence of certain factors, and "constitutive promoter" refers to an unregulated promoter that allows for continuous transcription of its associated gene or genes.

In a preferred embodiment, both the nucleotide sequences encoding the helper protein and the POI are driven by an inducible promoter. In another preferred embodiment, both the nucleotide sequences encoding the helper protein and POI is driven by a constitutive promoter. In yet another preferred embodiment, the nucleotide sequences encoding the helper protein is driven by a constitutive promoter and the POI is driven by an inducible promoter. In yet another preferred embodiment, the nucleotide sequences encoding the helper protein is driven by an inducible promoter and the POI is driven by a constitutive promoter. As an example, the HP may be driven by a constitutive GAP promoter and the POI may be driven by an inducible AOX1 promoter. In one embodiment, the nucleotide sequences encoding the helper protein and POI is driven by the same promoter or similar promoters in terms of promoter activity and/or expression behaviour.

Many inducible promoters are known in the art. Many are described in a review by Gatz, Curr. Op. Biotech., 7: 168 (1996) (see also Gatz, Ann. Rev. Plant. Physiol. Plant Mol. Biol., 48:89 (1997)). Examples include tetracycline repressor system, Lac repressor system, copper-inducible systems, salicylate-inducible systems (such as the PR1 a system), glucocorticoid-inducible (Aoyama et al., 1997), alcohol-inducible systems, e.g., AOX promoters, and ecdysome-inducible systems. Also included are the benzene sulphonamide-inducible (U.S. Pat. No. 5,364,780) and alcohol-inducible systems (WO 97/06269 and WO 97/06268) and glutathione 5-transferase promoters.

Suitable promoter sequences for use with yeast host cells are described in Mattanovich et al., Methods Mol. Biol. (2012) 824:329-58 and include glycolytic enzymes like triosephosphate isomerase (TPI), phosphoglycerate kinase (PGK), glyceraldehyde-3-phosphate dehydrogenase (GAPDH or GAP) and variants thereof, lactase (LAC) and galactosidase (GAL), P. pastoris glucose-6-phosphate isomerase promoter (PPGI, the 3-phosphoglycerate kinase promoter (PPGK), the glycerol aldehyde phosphate dehydrogenase promoter (PGAP), translation elongation factor promoter (PTEF), and the promoters of P. pastoris enolase 1 (PENO1), triose phosphate isomerase (PTPI), ribosomal subunit proteins (PRPS2, PRPS7, PRPS31, PRPL1), alcohol oxidase promoter (PAOX) or variants thereof with modified characteristics, the formaldehyde dehydrogenase promoter (PFLD), isocitrate lyase promoter (PICL), alpha-ketoisocaproate decarboxylase promoter (PTHI), the promoters of heat shock protein family members (PSSA1, PHSP90, PKAR2), 6-Phosphogluconate dehydrogenase (PGND1), phosphoglycerate mutase (PGPM1), transketolase (PTKL1), phosphatidylinositol synthase (PPIS1), ferro-O2-oxidoreductase (PFET3), high affinity iron permease (PFTR1), repressible alkaline phosphatase (PPHO8), N-myristoyl transferase (PNMT1), pheromone response transcription factor (PMCM1), ubiquitin (PUBI4), single-stranded DNA endonuclease (PRAD2), the promoter of the major ADP/ATP carrier of the mitochondrial inner membrane (PPET9) (WO2008/128701) and the formate dehydrogenase (FMD) promoter. The GAP promoter, AOX promoter or a promoter derived from GAP or AOX promoter is particularly preferred. AOX promoters can be induced by methanol and are repressed by e.g. glucose.

Further examples of suitable promoters include Saccharomyces cerevisiae enolase (ENO-1), Saccharomyces cerevisiae galactokinase (GAL1), Saccharomyces cerevisiae alcohol dehydrogenase/glyceraldehyde-3-phosphate dehydrogenase (ADH1, ADH2/GAP), Saccharomyces cerevisiae triose phosphate isomerase (TPI), Saccharomyces cerevisiae metallothionein (CUP1), and Saccharomyces cerevisiae 3-phosphoglycerate kinase (PG K), and the maltase gene promoter (MAL).

Other useful promoters for yeast host cells are described by Romanos et al, 1992, Yeast 8:423-488.

Suitable promoter sequences for use with E. coli include T7 promoter, T5 promoter, tryptophan (trp) promoter, lactose (lac) promoter, tryptophan/lactose (tac) promoter, lipoprotein (lpp) promoter, and A phage PL promoter in plasmids.

The promoter which drives the expression of the polynucleotide encoding the helper protein is preferably not the endogenous to the promoter of the helper gene. Preferably, a recombinant promoter is used instead of the endogenous promoter of the helper protein gene. A "recombinant" promoter is referred to with respect to the sequence whose expression it drives. As used herein, a recombinant promoter means when the promoter is not a native promoter to the given sequence, i.e., when the promoter is different from a naturally occurring promoter (the "native promoter"). Such a promoter is sometimes also referred to herein as heterologous promoter.

In a preferred embodiment, the overexpression is achieved by using an enhancer to enhance the promoter activity which drives the expression of the helper protein. Transcriptional enhancers are relatively orientation and position independent, having been found 5' and 3' to the transcription unit, within an intron, as well as within the coding sequence itself. The enhancer may be spliced into the expression vector at a position 5' or 3' to the coding sequence, but is preferably located at a site 5' from the promoter. Most yeast genes contain only one UAS, which generally lies within a few hundred base pairs of the cap site and most yeast enhancers (UASs) cannot function when located 3' of the promoter, but enhancers in higher eukaryotes can function both 5' and 3' of the promoter.

Many enhancer sequences are now known from mammalian genes (globin, RSV, SV40, EMC, elastase, albumin, a-fetoprotein and insulin). One may also use an enhancer from a eukaryotic cell virus, such as the SV40 late enhancer, the cytomegalovirus early promoter enhancer, the polyoma enhancer on the late side of the replication origin, and adenovirus enhancers. Yeast enhancers, also called upstream activating sequences (UASs), such as the UAS/Gal system from Saccharomyces cerevisiae, can be advantageously used with yeast promoters (described in European Patent No. 0317254 and Rudoni et al., The International Journal of Biochemistry and Cell Biology, (2000), 32(2):215-224).

It is preferred that the present host cell underexpressing the KO protein(s) would coexpress the protein of interest and a helper protein having an amino acid sequence having at least 30% sequence identity to an amino acid sequence as shown in SEQ ID NO: 1, 2, 3, 4, 5, 6, 7, 8, 9, or 162.

Preferably, the host cell can be engineered to overexpress 2, 3, 4, 5, 6, 7, 8 or more of helper proteins selected from SEQ ID NO: 1, 2, 3, 4, 5, 6, 7, 8, 9, or 162 or functional homologues thereof. In a preferred embodiment, the host cell can be engineered to (1) underexpress 1, 2, 3 or more of KO proteins KO1, KO2, KO3 or functional homologues thereof and (2) overexpress 1, 2, 3, 4, 5, 6, 7, 8, 9 or more of helper proteins HP1, HP2, HP3, HP4, HP5, HP6, HP7, HP8, HP9, HP10 or functional homologues thereof.

However, a specific combination of helper proteins HP3 (SEQ ID NO: 2) or a functional homologue and HP1 (SEQ ID NO. 4) or a functional homologue, or helper proteins HP10 (SEQ ID NO: 162) or a functional homologue and HP3 (SEQ ID NO: 2) or a functional homologue, is a preferred embodiment of the host cells of the present invention that are preferably applied in the methods and uses of the present invention.

Also, a specific combination of helper protein HP2 (SEQ ID NO: 1) or a functional homologue and HP3 (SEQ ID NO: 2) or a functional homologue and KO protein KO1 (SEQ ID NO: 10), or helper protein HP2 (SEQ ID NO: 1) or a functional homologue and HP1 (SEQ ID NO: 4) or a functional homologue and KO protein KO1 (SEQ ID NO: 10), is a preferred embodiment of the host cells of the present invention that are preferably applied in the methods and uses of the present invention.

Host cells being engineered to reflect such a combination are envisaged in a preferred embodiment. These host cells are preferably applied in the methods and uses described herein. "Reflected" means that the skilled person knows in accordance with the teaching of the present invention that a helper protein is overexpressed, while a KO protein is underexpressed.

It is preferred that the present host cell for manufacturing a protein of interest is engineered to underexpress at least one polynucleotide encoding a KO protein having an amino acid sequence as shown in SEQ ID NO: 10, 11, 12 or a functional homologue thereof and further overexpresses at least one polynucleotide encoding a helper protein having an amino acid sequence as shown in SEQ ID NO: 1, 2, 3, 4, 5, 6, 7, 8, 9, or 162 or a functional homologue thereof, wherein the functional homologue of the helper protein has at least 30%, such as at least 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, sequence identity to an amino acid sequence as shown in SEQ ID NO: 1, 2, 3, 4, 5, 6, 7, 8, 9, or 162.

In a preferred embodiment, the underexpression of at least one polynucleotide encoding a KO protein, in concert with the overexpression of at least one polynucleotide encoding a helper protein, may increase the yield of the protein of interest, for example SDZ-Fab (SEQ ID NO: 25 and 26) or HyHEL-Fab (SEQ ID NO: 29 and 20) in the host cell by at least 1%, such as at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190 or at least 200% or more, compared to the host cell prior to the engineering to underexpress the polynucleotide encoding the KO protein.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are for the purpose of describing and disclosing, for example, the cell lines, constructs, and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention and defined in the claims. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLES

The below examples will demonstrate that the newly identified gene(s) increases the titer (product per volume in mg/L) and the yield (product per biomass in mg/g biomass measured as dry cell weight or wet cell weight), respectively, of recombinant proteins upon its/their underexpression. As an example, the yield of recombinant antibody Fab fragments and recombinant enzymes in the yeast *Pichia pastoris* are increased. The positive effect was shown in shaking cultures (conducted in shake flasks or deep well plates) and in lab scale fed-batch cultivations.

Example 1 Generation of *P. pastoris* Production Strains a) Construction of *P. pastoris* Strains Secreting Antibody Fab Fragment HyHEL

*P. pastoris* CBS7435 (CBS, genome sequenced by Küberl et al. 2011) mut$^s$ variant was used as host strain. The pPM2d_pGAP and pPM2d_pAOX expression vectors are derivatives of the pPuzzle_ZeoR vector backbone described in WO2008/128701A2, consisting of the pUC19 bacterial origin of replication and the Zeocin antibiotic resistance cassette. Expression of the heterologous gene is mediated by the *P. pastoris* glyceraldehyde-3-phosphate dehydrogenase (GAP) promoter or alcohol oxidase (AOX) promoter, respectively, and the *S. cerevisiae* CYC1 transcription terminator. The light chain (LC) and the heavy chain (HC) of the antibody Fab fragment HyHEL (FIG. 2) were amplified from vector DNA template (carrying the gene of interests with N-terminal *S. cerevisiae* alpha mating factor signal leader sequence) using the primers for HyHEL-HC and HyHEL-LC in Table 3, and each ligated into both vectors pPM2d_pGAP and pPM2d_pAOX digested with SbfI and SfiI. The LC fragments were ligated into variants of pPM2d_pGAP and pPM2d_pAOX, where one restriction enzyme site in the promoter region was exchanged for another to allow subsequent linearization (NdeI instead of AwlI in pPM2d_pGAP, Bsu36I instead of Bpu1102I in pPM2d_pAOX), the HC fragments were ligated into the unmodified versions of the vectors. After sequence verification of LC and HC, the expression cassettes for both chains were combined onto one vector by using the compatible restriction enzymes MreI and AgeI.

genomic DNA was obtained by cooking and freezing of *P. pastoris* colonies for 5 minutes each and directly applied for PCR with the appropriate primers.

Table 3 shows oligonucleotide primers for PCR amplification of HyHEL LC and HC as well as SDZ LC and HC (Alpha-mating factor_forward is the forward primer for amplification of all Fab chains).

TABLE 3

| Primer | Restriction site attached | sequence |
|---|---|---|
| Alpha-mating factor_ forward* | SbfI | ACTACCTGCAGGCGAAACGATGAGATTCCCATC SEQ ID NO: 33 |
| HyHEL-HC backward | SfiI | TCATGGCCGAGGCGGCCCTATTACTTGTCACAGG ACTTTGGCTC SEQ ID NO: 34 |
| HyHEL-LC backward | SfiI | CTATGGCCGAGGCGGCCCTATTAACACTCACCTCT GTTG SEQ ID NO: 35 |
| SDZ-HC back | SfiI | TATCGGCCGAGGCGGCCCTATTACTTACCTGGGG ACAAG SEQ ID NO: 36 |
| SDZ-LC back | SfiI | CTATGGCCGAGGCGGCCCTATTAACACTCACCTCT GTTG SEQ ID NO: 37 |

Plasmids were linearized using NdeI restriction enzyme (for pPM2d_pGAP) or Bsu36I restriction enzyme (for pPM2d_pAOX), respectively, prior to electroporation (using a standard transformation protocol described in Gasser et al. 2013. Future Microbiol. 8(2):191-208) into *P. pastoris*. Selection of positive transformants was performed on YPD plates (per liter: 10 g yeast extract, 20 g peptone, 20 g glucose, 20 g agar-agar) containing 50 μg/mL of Zeocin. Colony PCR was used to ensure the presence of the transformed plasmid. Therefore, genomic DNA was obtained by cooking and freezing of *P. pastoris* colonies for 5 minutes each and directly applied for PCR with the appropriate primers.

b) Construction of a *P. pastoris* Strain Secreting Antibody Fab Fragment SDZ

The light chain (LC) and the heavy chain (HC) of the antibody Fab fragment SDZ (FIG. 2) were amplified from vector DNA template (carrying the gene of interests with N-terminal alpha mating factor signal leader sequence) using the primers for SDZ-HC and SDZ-LC in Table 3, and each ligated into pPM2d_pAOX or the variant of pPM2d_pAOX with the Bsu36I restriction site, respectively, each digested with SbfI and SfiI. After sequence verification of LC and HC, the expression cassettes for both chains were combined onto one vector by using the compatible restriction enzymes MreI and AgeI.

Plasmids were linearized using Bsu36I restriction enzyme prior to electroporation (using a standard transformation protocol described in Gasser et al. 2013. Future Microbiol. 8(2):191-208) into *P. pastoris*. Selection of positive transformants was performed on YPD plates (per liter: 10 g yeast extract, 20 g peptone, 20 g glucose, 20 g agar-agar) containing 50 μg/mL of Zeocin. Colony PCR was used to ensure the presence of the transformed plasmid. Therefore, Example 2 Chemostat Cultivation Cultivations were performed with 1.4 L DASGIP reactors (Eppendorf, Germany) with a maximum working volume of 1.0 L.

Following media were used:

$PTM_1$ trace salts stock solution (per litre) contains: 6.0 g $CuSO_4.5H_2O$, 0.08 g NaI, 3.36 g $MnSO_4.H_2O$, 0.2 g $Na_2MoO_4.2H_2O$, 0.02 g $H_3BO_3$, 0.82 g $CoCl_2$, 20.0 g $ZnCl_2$, 65.0 g $FeSO_4.7H_2O$, and 5.0 mL $H_2SO_4$(95%-98%).

Glycerol Batch medium (per litre) contains: 2 g Citric acid monohydrate ($C_6H_8O_7.H_2O$), 39.2 g Glycerol, 20.8 g $NH_4H_2PO_4$, 0.5 g $MgSO_4.7H_2O$, 1.6 g KCl, 0.022 g $CaCl_2.2H_2O$, 0.8 mg biotin and 4.6 mL PTM1 trace salts stock solution. HCl was added to set the pH to 5.

Glucose Chemostat medium (per litre) contains: 2.5 g Citric acid monohydrate ($C_6H_8O_7.H_2O$), 55.0 g glucose monohydrate, 21.8 g $NH_4H_2PO_4$, 1.0 g $MgSO_4.7H_2O$, 2.5 g KCl, 0.04 g $CaCl_2.2H_2O$, 4.0 mg biotin and 2.43 mL PTM1 trace salts stock solution. HCl was added to set the pH to 5.

Methanol/Glycerol Chemostat medium (per litre) contains: 2.5 g Citric acid monohydrate ($C_6H_8O_7.H_2O$), 8.5 g methanol, 50.0 g glycerol, 21.8 g $NH_4H_2PO_4$, 1.0 g $MgSO_4.7H_2O$, 2.5 g KCl, 0.04 g $CaCl_2.2H_2O$, 4.0 mg biotin and 2.43 mL PTM1 trace salts stock solution. HCl was added to set the pH to 5.

The dissolved oxygen was controlled at DO=20% with stirrer speed (400-1200 rpm) and aeration rate (12-72 standard Liter/hour (sL/h)) air, the temperature was controlled at 25° C. and the pH setpoint of 5 was controlled with addition of $NH_4OH$ (25%). Foaming was controlled by addition of antifoam agent (5% Glanapon 2000) on demand.

To start the cultivation, 0.4 L batch medium was sterile filtered and transferred into the fermenter under a sterile work bench and was inoculated (from a *P. pastoris* overnight pre-culture in YPG containing 50 μg/mL Zeocin, 180 rpm, 28° C.) with a starting optical density ($OD_{600}$) of 1. The batch phase of approximately 24 h reached a dry biomass concentration of approximately 20 g/L, it was followed by a constant feed with chemostat medium at 40 mL/h (for p=D=0.1/h) with simultaneous constant removal of culture to keep the total volume constant. A dry biomass concentration of approximately 25 g/L was reached after 7 residence times (70 hours) when samples for microarray experiments were taken and the cultivation was terminated. This chemostat cultivation was performed three times with each production strain (CBS7435 pGAP HyHEL-Fab using glucose chemostat medium and CBS7435mut$^s$ pAOX HyHEL-Fab using methanol/glycerol chemostat medium) and non-producing wildtype control strain (CBS7435 pGAP control and CBS7435mut$^s$ pAOX control, respectively) to obtain the biological replicates necessary for reliable microarray analysis.

Samples were taken after approximately 70 hours in steady state conditions of the chemostat. Routine sampling as determination of optical density or yeast dry mass, qualitative microscopic inspection and cell viability analysis was done alongside during each cultivation. For microarray analysis, samples were taken and treated as follows: For optimal quenching, 9 mL cell culture broth was immediately mixed with 4.5 mL of ice cold 5% phenol (Sigma) solution (in Ethanol abs.), and aliquoted. Each 2 mL were centrifuged (13,200 rpm for 1 minute) in pre-cooled collection tubes (GE healthcare, NJ), supernatant was removed completely and the tubes were stored at −80° C. until RNA isolation.

Example 3 Microarrays & Data Evaluation for Transcriptomic Experiments a) RNA isolation and sample preparation for microarray hybridization The RNA was isolated from chemostat sample cells using TRI reagent according to the supplier's instructions (Ambion, US). The cell pellets were resuspended in TRI reagent and homogenized with glass beads using a FastPrep 24 (M.P. Biomedicals, CA) at 5 m s$^{-1}$ for 40 seconds. After addition of chloroform, the samples were centrifuged and the total RNA was precipitated from the aqueous phase by adding isopropanol. The pellet was washed with 70% ethanol, dried and re-suspended in RNAse free water. RNA concentrations were determined by measuring $OD_{260}$ using a Nanodrop 1000 spectrophotometer (NanoDrop products, DE). Remaining DNA from the samples was removed using the DNA free Kit (Ambion, CA). Sample volume equal to 10 μg RNA was diluted to 50 μL in RNAse free water, then DNAse buffer I and rDNAse I were added and incubated at 37° C. for 30 minutes. After addition of DNAse Inactivation Reagent, the sample was centrifuged and the supernatant was transferred into a fresh tube. RNA concentrations were determined again like described above. Additionally, RNA integrity was analyzed using RNA nano chips (Agilent). To monitor the microarray workflow from amplification and labelling to hybridisation of the samples, the Spike In Kit (Agilent, Product Nr.: 5188-5279) was used as positive control. It contains 10 different polyadenylated transcripts from an adenovirus, which are amplified, labelled and cohybridised together with the own RNA samples. The samples were labelled with Cy 3 and Cy 5 using the Quick Amp Labelling Kit (Agilent, Prod. Nr. 5190-0444). Therefore 500 ng of purified sample RNA were diluted in 8.3 μL RNAse free water, 2 μL Spike A or B, and 1.2 μL T7 promoter primer were added. The mixture was denatured for 10 minutes at 65° C. and kept on ice for 5 minutes. Then 8.5 μL cDNA mastermix (per sample: 4 μL 5× first strand buffer, 2 μL 0.1 M DTT, 1 μL 10 mM dNTP mix, 1 μL MMLV-RT, 0.5 μL RNAse out) were added, incubated at 40° C. for 2 hours, then transferred to 65° C. for 15 minutes and put on ice for 5 minutes. The transcription mastermix (per sample: 15.3 μL nuclease free water, 20 μL transcription buffer, 6 μL 0.1 M DTT, 6.4 μL 50% PEG, 0.5 μL RNAse Inhibitor, 0.6 μL inorg. phosphatase, 0.8 μL T7 RNA Polymerase, 2.4 μL Cyanin 3 or Cyanin 5) was prepared and added to each tube and incubated at 40° C. for 2 hours. In order to purify the obtained labelled cRNA, the RNeasy Mini Kit (Qiagen, Cat. No. 74104) was used. Samples were stored at −80° C. Quantification of the cRNA concentration and labelling efficiency was done at the Nanodrop spectrophotometer.

b) Microarray Analysis

The Gene Expression Hybridisation Kit (Agilent, Cat. No. 5188-5242) was used for hybridisation of the labelled sample cRNAs. For the preparation of the hybridisation samples each 300 ng cRNA (Cy3 and Cy 5) and 6 μL 10-fold blocking agent were diluted with nuclease free water to a final volume of 24 μL. After addition of 1 μL 25-fold fragmentation buffer, the mixture was incubated at 60° C. for 30 minutes. Then 25 μL GEx Hybridisation Buffer HI-RPM was added to stop the reaction. After centrifugation for one minute with 13,200 rpm, the sample was chilled on ice and used for hybridisation immediately. In-house designed *P. pastoris* specific oligonucleotide arrays (AMAD-ID: 034821, 8×15K custom arrays, Agilent) were used. Microarray hybridisation was done according to the Microarray Hybridisation Chamber User Guide (Agilent G2534A). First, the gasket slide was uncovered and put onto the chamber base, Agilent label facing up. The sample (40 μL per array) was loaded in the middle of each of the eight squares. Then the microarray slide was carefully put onto the gasket slide (Agilent label facing down) and the chamber cover was placed on and fixed with the clamp. All samples were hybridized against a reference pool sample in a dye-swap manner. The pool RNA sample had been generated by combining RNA from a variety of cultivations in equal amounts. Hybridisation was done in the hybridisation oven for 17 hours at 65° C. Before scanning, the microarray chip was washed. Therefore, the chamber was dismantled, and the sandwich slides were detached from each other while submerged in wash buffer 1. The microarray was directly transferred into another dish with wash buffer 1, washed for 1 minute, transferred into wash buffer 2 (temperature at least 30° C.) and washed for another minute. After drying of the microarray slide by touching the slide edge with a tissue, it was put into the slide holder (Agilent label facing up). The slide holder was put into the carousel and scanning was started.

c) Data Acquisition and Statistical Evaluation of Microarray Data

Images were scanned at a resolution of 50 nm with a G2565AA Microarray scanner (Agilent) and were imported into the Agilent Feature Extraction 9.5 software. Agilent Feature Extraction 9.5 was used for the quantification of the spot intensities. The raw mean spot intensity data was then imported into the open source software R for further normalisation and data analysis.

The intensity data were subjected to normalization (no background correction, the within slide normalization method Loess and the between slide normalization method Aquantile was used), before the differential expression values were calculated. The p-values associated with the differential expression values were calculated using a linear model fit (limma R package), subsequently they were adjusted for multiple testing using the method of Benjamini and Yekutieli (BY method of limma R package). Log 2 fold changes were calculated for HyHEL-Fab producing strains compared to their respective control.

The microarray data was browsed for entries with significant (adjusted p-value <0.05) difference in expression levels (fold change >1.5) between the chemostat triplicates of CBS7435 producing HyHEL-Fab and its non-producing host control.

Table 4 shows up-regulated genes from microarray analysis of HyHEL-Fab producing *P. pastoris*.

TABLE 4

| Gene identifier P. pastoris CBS7435 | Microarray probe name | Transcript level fold change in CBS7435 pPM2d_pGAP HyHEL vs. control | Transcript level fold change in CBS7435 pPM2d_pAOX HyHEL vs. control |
|---|---|---|---|
| PAS_chr4_0822 | Pipas_chr4_0822 | 1.20 | 8.27 |
| PP7435_Chr4-1007 | Pipas_chr4_0009 | 2.68 | 5.56 |
| PP7435_Chr3-0183 | Pipas_chr3_0987 | 2.17 | 5.47 |
| PP7435_Chr1-1225 | Pipas_chr1-4_0431 | 2.48 | 4.76 |
| PP7435_Chr4-0976 | PIPA00444 | 2.27 | 4.22 |
| PP7435_Chr2-0351 | Pipas_chr2-2_0331 | 1.74 | 4.10 |
| PP7435_Chr1-0941 | Pipas_chr1-4_0167 | 0.93 | 3.12 |
| PP7435_Chr3-0933 | Pipas_chr3_0288 | 2.06 | 3.11 |
| PAS_chr3_0401 | Pipas_chr3_0401 | 2.59 | 2.92 |
| PP7435_Chr1-1232 | Pipas_chr1-4_0681 | 1.57 | 2.79 |
| PP7435_Chr4-0294 | Pipas_chr4_0673 | 2.11 | 2.70 |
| PP7435_Chr1-0667 | Pipas_chr1-1_0348 | 2.02 | 2.69 |
| PP7435_Chr3-0607 | Pipas_chr3_0598 | 2.02 | 2.59 |
| PP7435_Chr2-0722 | Pipas_chr2-1_0566 | 1.13 | 2.50 |
| PP7435_Chr2-0842 | Pipas_chr2-1_0454 | 4.16 | 2.43 |
| PAS_chr3_0821 | Pipas_chr3_0821 | 1.40 | 2.18 |
| PP7435_Chr2-0501 | Pipas_chr2-1_0887 | 2.69 | 2.18 |
| PP7435_Chr2-0220 | Pipas_chr2-2_0210 | 1.27 | 2.17 |
| PP7435_Chr3-0278 | Pipas_chr3_0895 | 1.06 | 2.09 |
| PP7435_Chr4-0108 | Pipas_chr4_0843 | 1.80 | 2.04 |
| PP7435_Chr2-1019 | Pipas_chr2-1_0287 | 1.52 | 2.04 |
| PP7435_Chr3-1062 | Pipas_chr3_0170 | 1.75 | 1.96 |
| PP7435_Chr4-0448 | Pipas_chr4_0972 | 2.31 | 1.95 |
| PP7435_Chr3-0837 | Pipas_chr3_0377 | 1.38 | 1.87 |
| PP7435_Chr1-0176 | Pipas_chr1-3_0174 | 1.70 | 1.84 |
| PP7435_Chr3-0156 | Pipas_chr3_1014 | 1.30 | 1.84 |
| PP7435_Chr4-0582 | Pipas_chr4_0403 | 1.34 | 1.82 |
| PP7435_Chr2-0638 | Pipas_chr2-1_0642 | 2.35 | 1.78 |
| PP7435_Chr3-0639 | Pipas_chr3_0567 | 1.70 | 1.73 |
| PP7435_Chr2-0866 | Pipas_chr2-1_0433 | 1.36 | 1.71 |
| PP7435_Chr2-0028 | Pipas_chr2-2_0031 | 1.70 | 1.71 |
| PP7435_Chr1-1009 | Pipas_chr1-4_0229 | 4.09 | 1.70 |
| PP7435_Chr2-0848 | Pipas_chr2-1_0448 | 1.39 | 1.70 |
| PP7435_Chr1-0470 | Pipas_chr1-1_0160 | 1.39 | 1.69 |
| PP7435_Chr1-0077 | Pipas_chr1-3_0080 | 1.31 | 1.68 |
| PP7435_Chr1-1220 | Pipas_chr1-4_0428 | 1.49 | 1.68 |
| PP7435_Chr1-0571 | Pipas_chr1-1_0259 | 2.18 | 1.68 |
| PP7435_Chr1-0204 | Pipas_chr1-3_0202 | 0.71 | 1.67 |
| PP7435_Chr4-0182 | Pipas_chr4_0775 | 1.22 | 1.65 |
| PP7435_Chr4-0320 | Pipas_chr4_0650 | 1.26 | 1.65 |
| PP7435_Chr3-0548 | Pipas_chr3_0652 | 2.29 | 1.62 |
| PP7435_Chr2-1300 | Pipas_chr2-1_0002 | 3.71 | 1.62 |
| PP7435_Chr1-1077 | Pipas_chr1-4_0294 | 1.46 | 1.61 |
| PP7435_Chr4-0699 | Pipas_chr4_0299 | 1.43 | 1.61 |
| PP7435_Chr2-0729 | Pipas_chr2-1_0560 | 1.12 | 1.56 |
| PP7435_Chr4-0923 | Pipas_chr4_0093 | 0.94 | 1.53 |
| PP7435_Chr1-0592 | Pipas_chr1-1_0276 | 1.59 | 1.52 |

Example 4 Generation of Strains Overexpressing Identified Genes

For the investigation of positive effects on Fab secretion, the identified genes were overexpressed in two different Fab producing strains: CBS7435 pPM2d_pAOX HyHEL, which was the source of the microarray data (see Example 3) and CBS7435 pPM2d_pAOX SDZ (generation see Example 1).

a) Amplification and Cloning of the Identified Potential Secretion Helper Genes into pPM2aK21 Expression Vectors The genes identified in Example 3 were amplified by PCR (Phusion Polymerase, New England Biolabs) from start to stop codon using the primers shown in Table 5. The sequences were cloned into the MCS of the pPM2a expression vector with the two restriction enzymes SbtI and SfiI. pPMKaK21 is a derivative of pPM2d (described in Example 1a), consisting of an AOX terminator sequence (for integration into the native AOX terminator locus), an origin of replication for *E. coli* (pUC19), an antibiotic resistance cassette (kanMX conferring resistance to Kanamycin and G418) for selection in *E. coli* and yeast, an expression cassette for the gene of interest (G01) consisting of a GAP promoter, a multiple cloning site (MCS) and the *S. cerevisiae* CYC1 transcription terminator. Gene sequences were verified by Sanger sequencing.

TABLE 5

| Gene identifier (ORF name CBS7435) | Forward primer (SbfI attached) | Backward primer (SfiI attached) |
|---|---|---|
| PAS_chr4_0822 | CTTGCCTGCAGGATGCTAACGGCCAGTTGGTC<br>SEQ ID NO: 38 | GATCGGCCGAGGCGGCCTCAGCAGTATTCCCACCAGAATC<br>SEQ ID NO: 39 |
| PP7435_Chr4-1007 | CTTGCCTGCAGGATGTCAGTTCATTTCGTTATAGCAGC<br>SEQ ID NO: 40 | GATCGGCCGAGGCGGCCTCATATAAAAGGTTTATCATAATTCTCATCCTCAG<br>SEQ ID NO: 41 |
| PP7435_Chr3-0183 | GAAACCTGCAGGATGTCTGAATTTGTTGCTAAAATTAACATTC<br>SEQ ID NO: 42 | GATCGGCCGAGGCGGCCTTAGGCGGTTGGAACGTTC<br>SEQ ID NO: 43 |
| PP7435_Chr1-1225 | GAAACCTGCAGGATGTCTCATCTATTACTGCGTGACAGC<br>SEQ ID NO: 44 | GATCGGCCGAGGCGGCCTCATGGCCCGGCATATCTAG<br>SEQ ID NO: 45 |
| PP7435_Chr4-0976 | GACACCTGCAGGATGTCTGAATCCTCCAGTATCTCTCTAGTTG<br>SEQ ID NO: 46 | GATCGGCCGAGGCGGCCCTAGATACATCCCAAAAGTGCACCG<br>SEQ ID NO: 47 |
| PP7435_Chr2-0351 | GATACCTGCAGGATGATCCTGGGTTCAGTTTGGG<br>SEQ ID NO: 48 | GATCGGCCGAGGCGGCCCTAAAAGTTTGCTGCAGCATTTGAAG<br>SEQ ID NO: 49 |
| PP7435_Chr1-0941 | CTTGCCTGCAGGATGGGTTGCTTTAGATTTTGTCTGG<br>SEQ ID NO: 50 | GATCGGCCGAGGCGGCCCTATTTGTATACGTGCTGTGGAGCC<br>SEQ ID NO: 51 |
| PP7435_Chr3-0933 | CTTGCCTGCAGGATGTTAAACAAGCTGTTCATTGCAATACTC<br>SEQ ID NO: 52 | GATCGGCCGAGGCGGCCTTAGCTGGCAAGGGTAATTGTCTC<br>SEQ ID NO: 53 |
| PAS_chr3_0401 | GACACCTGCAGGATGGCTCCTCAAACACCAAGG<br>SEQ ID NO: 54 | GATCGGCCGAGGCGGCCTCAAAAAAACAATCTCAAAATCTCCAG<br>SEQ ID NO: 55 |
| PP7435_Chr1-1232 | GTACCCTGCAGGATGACCAAGGAAAATGAAGCC<br>SEQ ID NO: 56 | GATCGGCCGAGGCGGCCTTATTTTTTCTCCAATTCAGCCAG<br>SEQ ID NO: 57 |
| PP7435_Chr4-0294 | GAAACCTGCAGGATGCTGTTGTCACATACCATGATACTTC<br>SEQ ID NO: 58 | GATCGGCCGAGGCGGCCTTAAGATTGCTTCTTTTTGAGATTGG<br>SEQ ID NO: 59 |
| PP7435_Chr1-0667 | GAAACCTGCAGGATGACGGACTATGTCACTTCTAAGCG<br>SEQ ID NO: 60 | GATCGGCCGAGGCGGCCTCATAATCTCCCTCCAGGGG<br>SEQ ID NO: 61 |
| PP7435_Chr3-0607 | GAAACCTGCAGGATGTCGTCTGATGCTGTGGAG<br>SEQ ID NO: 62 | GATCGGCCGAGGCGGCCTCAAATAATGCTACATTTGCGTTTCTTTC<br>SEQ ID NO: 63 |
| PP7435_Chr2-0722 | CTTGCCTGCAGGATGTCTTATACGTCGGACAACAAAGAG<br>SEQ ID NO: 64 | GATCGGCCGAGGCGGCCTTACGTGTATCCGCTTCCTCTGTAC<br>SEQ ID NO: 65 |
| PP7435_Chr2-0842 | GATACCTGCAGGATGAACTTGTACCTAATTACATTACTATTCGC<br>SEQ ID NO: 66 | GATCGGCCGAGGCGGCCTTAGAACCCACATTGATTTGGATACTG<br>SEQ ID NO: 67 |
| PAS_chr3_0821 | GAAACCTGCAGGATGTCGTTATCAACCTTTCTAGGCG<br>SEQ ID NO: 68 | GATCGGCCGAGGCGGCCTCAGACTCTACTCATCATTTTGTCTTCCTC<br>SEQ ID NO: 69 |
| PP7435_Chr2-0501 | GAAACCTGCAGGATGATGTACAGGAACTTAATAATTGCTACTGC<br>SEQ ID NO: 70 | GATCGGCCGAGGCGGCCCTAACACTCTATGAGGTCTACAATGTCCAAC<br>SEQ ID NO: 71 |
| PP7435_Chr2-0220 | CATGCCTGCAGGATGTCTACAGCAATTCCAGGAGGAC<br>SEQ ID NO: 72 | GATCGGCCGAGGCGGCCTTAGTTGATCAACTTTCCTGTCAGCTTAG<br>SEQ ID NO: 73 |
| PP7435_Chr3-0278 | GACACCTGCAGGATGAGTGGTGACCATAAGAGCTTTACG<br>SEQ ID NO: 74 | GATCGGCCGAGGCGGCCTTACTGTGTACCATACCGATCCAATCC<br>SEQ ID NO: 75 |

TABLE 5-continued

| Gene identifier (ORF name CBS7435) | Forward primer (SbfI attached) | Backward primer (SfiI attached) |
|---|---|---|
| PP7435_Chr4-0108 | CTTGCCTGCAGGATGACTAACTGGAAAGCGATATTGACTCC<br>SEQ ID NO: 76 | GATCGGCCGAGGCGGCCTTAGTTCTCTTCTTCACCTTGAAATTTTAGGC<br>SEQ ID NO: 77 |
| PP7435_Chr2-1019 | GCAACCTGCAGGATGTCTTATCGCCCTCAGTTTCAAC<br>SEQ ID NO: 78 | GATCGGCCGAGGCGGCCTCAATAGATCTTTTTCTTTTCATCAAAACTCAAC<br>SEQ ID NO: 79 |
| PP7435_Chr3-1062 | GATACCTGCAGGATGGTGGTGCACAACCCTAATAAC<br>SEQ ID NO: 80 | GATCGGCCGAGGCGGCCCTAGGTACTATGCTGAACATCCTGAGTATGAG<br>SEQ ID NO: 81 |
| PP7435_Chr4-0448 | GAAACCTGCAGGATGAGATTTTCTAACGTCGTTTTAACTGC<br>SEQ ID NO: 82 | GATCGGCCGAGGCGGCCTTACAAGGCAAAGACTCCGAAAGTG<br>SEQ ID NO: 83 |
| PP7435_Chr3-0837 | GACACCTGCAGGATGACTGTGCCTGATCTGAAAGAAAC<br>SEQ ID NO: 84 | GATCGGCCGAGGCGGCCTCAGGCCAGCGCAACG<br>SEQ ID NO: 85 |
| PP7435_Chr1-0176 | CTTGCCTGCAGGATGAAGATATGGCTGGTACTTCTTTTAGTTTTTG<br>SEQ ID NO: 86 | GATCGGCCGAGGCGGCCTCACAATTCGTCTCTAATTTGTTGCG<br>SEQ ID NO: 87 |
| PP7435_Chr3-0156 | CTTGCCTGCAGGATGGAGCAGGTTCCAGTCG<br>SEQ ID NO: 88 | GATCGGCCGAGGCGGCCTTATTCATCATAAACTTCTTCTATGGTGGC<br>SEQ ID NO: 89 |
| PP7435_Chr4-0582 | CTTGCCTGCAGGATGGATCCTTTTTCAATTCTTCTCAC<br>SEQ ID NO: 90 | GATCGGCCGAGGCGGCCCTACTTTGGAGACAGATCTTCCACCTTAAC<br>SEQ ID NO: 91 |
| PP7435_Chr2-0638 | GAAACCTGCAGGATGACCAGTCAAGGATTTTTGGATC<br>SEQ ID NO: 92 | GATCGGCCGAGGCGGCCCTATATGCTATCAACCATCTCCATCAAATAAC<br>SEQ ID NO: 93 |
| PP7435_Chr3-0639 | GACACCTGCAGGATGACTCCCCGTTCTCATATTTTC<br>SEQ ID NO: 94 | GATCGGCCGAGGCGGCCCTACTCAAAGAACTTAGACAAAGCAGCTTTCTC<br>SEQ ID NO: 95 |
| PP7435_Chr2-0866 | GATCCCTGCAGGATGGCAGAAGAAGAACC<br>SEQ ID NO: 96 | GATCGGCCGAGGCGGCCCTAATTAGTAATACTTGCTTCTATTTCCTGGTACAAC<br>SEQ ID NO: 97 |
| PP7435_Chr2-0028 | GAACCCTGCAGGATGATTTTGAGCAAGCTGTCGTTTAGAC<br>SEQ ID NO: 98 | GATCGGCCGAGGCGGCCTTATTTATTAACAATGACATCATCTTCAAACTCG<br>SEQ ID NO: 99 |
| PP7435_Chr1-1009 | CTTGCCTGCAGGATGGGTGCCATTGGAATG<br>SEQ ID NO: 100 | GATCGGCCGAGGCGGCCCTATTGCAGAACATTCGATATCCAATC<br>SEQ ID NO: 101 |
| PP7435_Chr2-0848 | GATACCTGCAGGATGCTACCATTTTCGTACGACGTG<br>SEQ ID NO: 102 | GATCGGCCGAGGCGGCCCTATAACTCTCCATTCTCCTCGTCGATC<br>SEQ ID NO: 103 |
| PP7435_Chr1-0470 | GATCCCTGCAGGATGAAAATATTAAGTGCATTGCTTCTTCTTTTTAC<br>SEQ ID NO: 104 | GATCGGCCGAGGCGGCCTTATAGCTCTTGGTGTAATAACTGGGG<br>SEQ ID NO: 105 |
| PP7435_Chr1-0077 | CTTGCCTGCAGGATGTCTAAACCCTACAAGCTGATAGGTGAG<br>SEQ ID NO: 106 | GATCGGCCGAGGCGGCCTTAATCTTCTCCAGCAGGTATCTCATCC<br>SEQ ID NO: 107 |
| PP7435_Chr1-1220 | CTTGCCTGCAGGATGAATCAATTTTCTCTAGCTTCACAAGTAAAC<br>SEQ ID NO: 108 | GATCGGCCGAGGCGGCCCTACTCGGTTAATGGTCCGAGTGC<br>SEQ ID NO: 109 |
| PP7435_Chr1-0571 | GACACCTGCAGGATGAGTTATAGGAAAGACAACAAACAAAG<br>SEQ ID NO: 110 | GATCGGCCGAGGCGGCCTTAGAAGGCAGCTTCATCATCG<br>SEQ ID NO: 111 |

TABLE 5-continued

| Gene identifier (ORF name CBS7435) | Forward primer (SbfI attached) | Backward primer (SfiI attached) |
|---|---|---|
| PP7435_Chr1-0204 | CTTGCCTGCAGGATGAGCAGCTTCAG AGTTCTAGACTTGG SEQ ID NO: 112 | GATCGGCCGAGGCGGCCTTACAGAT CAACGAATCC SEQ ID NO: 113 |
| PP7435_Chr4-0182 | GATACCTGCAGGATGAACATCTTTAGA ATCCTAGGTAAGTTTCC SEQ ID NO: 114 | GATCGGCCGAGGCGGCCTCATTCTG GCAGCTTGAATTTC SEQ ID NO: 115 |
| PP7435_Chr4-0320 | CTTGCCTGCAGGATGTCCACAACTACT AAGAAAAACAAGAACAGG SEQ ID NO: 116 | GATCGGCCGAGGCGGCCTTACCATG CACCCTTTCCTCTC SEQ ID NO: 117 |
| PP7435_Chr3-0548 | CTTGCCTGCAGGATGTCAGAGGAGTA AGAACCACAAACAG SEQ ID NO: 118 | GATCGGCCGAGGCGGCCTCAATTTA TTCTAGGTTTTTTGGTTCGG SEQ ID NO: 119 |
| PP7435_Chr2-1300 | GTACCCTGCAGGATGATGGCAAGTCC AACCG SEQ ID NO: 120 | GATCGGCCGAGGCGGCCCGCAACA ACGCTGGTTG SEQ ID NO: 121 |
| PP7435_Chr1-1077 | CTTGCCTGCAGGATGAGTAACCAGTAT AATCCGTATGAGCAG SEQ ID NO: 122 | GATCGGCCGAGGCGGCCCTATCTTC CCCAGTTTCCGACAC SEQ ID NO: 123 |
| PP7435_Chr4-0699 | GTTACCTGCAGGATGTCTACAGAGAA CAAAGCAGAGACAAAAC SEQ ID NO: 124 | GATCGGCCGAGGCGGCCCTATTTCT TTGCTTCAGCGTTTGC SEQ ID NO: 125 |
| PP7435_Chr2-0729 | CTTGCCTGCAGGATGTTAAACTTAATA TCCACAATAAGTGGGTG SEQ ID NO: 126 | GATCGGCCGAGGCGGCCTTAAGCAG GAGCAGATAACCAAGC SEQ ID NO: 127 |
| PP7435_Chr4-0923 | CTTGCCTGCAGGATGGGTAGAAGGAA AATAGAGATAAATCCG SEQ ID NO: 128 | GATCGGCCGAGGCGGCCTCAGCTCT TCTTAGTCACACTGCTTG SEQ ID NO: 129 |
| PP7435_Chr1-0592 | CTTGCCTGCAGGATGTCACTTCAACTG TCCATTATCTTCG SEQ ID NO: 130 | GATCGGCCGAGGCGGCCCTACTCGT CCTTCTTGTTGCTCTTCTC SEQ ID NO: 131 | b) Co-Overexpression of Identified Genes in *P. pastoris* Fab Producing Strains

The *P. pastoris* Fab overproducing strains CBS7435mut$^s$ pAOX HyHEL-Fab and CBS7435mut$^s$ pAOX SDZ-Fab were used as host strains for co-overexpression of the genes identified in Example 3 and cloned in Example 4a. Before transformation into the Fab producing strains, the pPM2aK21 vectors containing the secretion helper genes identified in Example 3 are linearized in the AOX terminator sequence with the restriction enzyme AscI. Positive transformants were selected on YPD agar plates containing G418.

Example 5 Screening for Fab Expression

In small-scale screenings, 8 to 12 transformants of each secretion helper gene were tested in comparison to the non-engineered parental host and ranked based on their impact on cell growth, Fab titer and Fab yield. Of all the tested clones, PP7435_Chr3-0933, PP7435_Chr2-0220, PP7435_Chr3-0639, PP7435_Chr1-1232, PP7435_Chr1-1225, PP7435 Chr3-0607, PP7435 Chr4-0448, PP7435 Chr4-0108, PP7435 Chr1-0667 were found to show the best results (increasing Fab titer or yield at least 1.2-fold).

In Example 7, all of these clones (except PP7435_Chr1-0667) were then cultivated in bioreactors for verification of strain improvement in controlled production processes.

a) Small Scale Cultivation of *Pichia pastoris* Fab Production Strains 2 mL YP-medium (10 g/L yeast extract, 20 g/L peptone) containing 10 g/L glycerol and 50 µg/mL Zeocin were inoculated with a single colony of *P. pastoris* strains and grown overnight at 25° C. Aliquots of these cultures (corresponding to a final $OD_{600}$ of 2.0) were transferred to 2 mL of Synthetic screening medium M2 (media composition is given below) supplemented with 20 g/L glucose and a glucose feed tablet (Kuhner, Switzerland; CAT # SMFB63319) and incubated for 25 h at 25° C. at 170 rpm in 24 deep well plates. The cultures were washed once by centrifugation, then the pellets were resuspended in Synthetic screening medium M2 and aliquots (corresponding to a final $OD_{600}$ of 4.0) were transferred into 2 mL of Synthetic screening medium M2 in fresh 24 deep well plates. Methanol (5 g/L) was added repeatedly every 12 h for 48 hours, before cells were harvested by centrifugation at 2500×g for 10 min at room temperature and prepared for analysis. Biomass was determined by measuring the cell weight of 1 mL cell suspension, while determination of the recombinant secreted protein in the supernatant is described in the following Examples 5b-6c.

Synthetic screening medium M2 contained per litre: 22.0 g Citric acid monohydrate 3.15 g $(NH_4)_2PO_4$, 0.49 g $MgSO_4*7H_2O$, 0.80 g KCl, 0.0268 g $CaCl_2*2H_2O$, 1.47 mL PTM1 trace metals, 4 mg Biotin; pH was set to 5 with KOH (solid)

b) SDS-PAGE & Western Blot Analysis

For protein gel analysis the NuPAGEO Novex® Bis-Tris system was used, using 12% Bis-Tris or 4-12% Bis-Tris gels and MOPS running buffer (all from Invitrogen). After electrophoresis, the proteins were either visualized by silver staining or transferred to a nitrocellulose membrane for Western blot analysis. Therefore, the proteins were electroblotted onto a nitrocellulose membrane using the XCell II™ Blot Module for wet (tank) transfer (Invitrogen) according to the manufacturer's instructions. After blocking, the Western Blots were probed with the following antibodies: For Fab light chain: anti-human kappa light chains (bound and free)—alkaline phosphatase (AP) conjugated antibody, Sigma A3813 (1:5,000); For Fab heavy chain: Mouse Anti-Human IgG antibody (Ab7497, Abcam) diluted 1:1,000 and Anti-Mouse IgG (Fc specific) Alkaline Phosphatase antibody produced in goat (A1418, Sigma) as secondary antibody diluted 1:5,000.

Detection was performed with the colorimetric AP detection kit (BioRad) based on the NBT/BCIP system for AP-conjugates, or the chemiluminescent Super Signal West Chemiluminescent Substrate (Thermo Scientific) for HRP-conjugates.

c) Quantification of Fab by ELISA

Quantification of intact Fab by ELISA was done using anti-human IgG antibody (ab7497, Abcam) as coating antibody and a goat anti-human IgG (Fab specific)—alkaline phosphatase conjugated antibody (Sigma A8542) as detection antibody. Human Fab/Kappa, IgG fragment (Bethyl P80-115) was used as standard with a starting concentration of 100 ng/mL, supernatant samples are diluted accordingly. Detection was done with pNPP (Sigma S0942). Coating-, Dilution- and Washing buffer were based on PBS (2 mM $KH_2PO_4$, 10 mM $Na_2HPO_4.2H_2O$, 2.7 mM g KCl, 8 mM NaCl, pH 7.4) and completed with BSA (1% (w/v)) and/or Tween20 (0.1% (v/v)) accordingly.

Example 6 Generation of Strains Underexpressing Selected Identified Genes

Some of the genes that had been identified in Example 3, resulted in less secreted Fab when overexpressed in HyHEL-Fab producing *P. pastoris* host strains (in Example 4 and 5). Two of these genes were encoding chaperones, namely the cytosolic chaperone HCH1/PP7435_Chr3-1062 (KO2) and the ER-resident chaperone SCJ1/PP7435 Chr1-0176 (KO3). This finding is very surprising because chaperones are generally regarded as having expression/secretion enhancing effects. To the inventors' surprise, the overexpression of PP7435_Chr1-0176 was detrimental, reducing Fab titers and yields to less than 80% of the parental non-engineered HyHEL-Fab or SDZ-Fab producing strains. Also PP7435_Chr3-1062 overexpression reduced HyHEL Fab titers and yields to less than 80% of the parental non-engineered strains. Thus, these genes (PP7435_Chr1-0176/SCJ1, PP7435_Chr3-1062/HCH1) were disrupted in both host strains. The flocculation transcription factor PP7435_Chr4-0252/FLO8 was additionally chosen as knock-out target after many flocculation-related genes were found to be strongly down-regulated (fold change <0.66) in the transcriptomics experiment (Example 3).

The *P. pastoris* Fab overproducing strains CBS7435mut$^s$ pAOX HyHEL-Fab and CBS7435mut$^s$ pAOX SDZ-Fab were used as host strains. A split marker cassette approach was used as described by Heiss et al. (2013) [Appl Microbiol Biotechnol. 97(3):1241-9. to generate transformants with a disrupted gene locus. Verification of positive knock-out strains was done by PCR, using genomic DNA of transformants which had been able to grow on G418 and primers outside of the disruption cassettes (Table 6).

Table 6 lists all primers that were used for the construction of the knock-out cassettes (2 overlapping split marker cassettes per knock-out target): The primer pairs A_forward/A_backward, B_forward/B_backward, C_forward/C_backward, D_forward/D_backward were used to amplify the fragments A, B, C and D by PCR (Phusion Polymerase, New England Biolabs). Fragment A is amplified from genomic *P. pastoris* DNA, starting 1700 bp in 5 prime direction of the respective ATG (of the targeted gene) until 200 bp in 5 prime direction of ATG. Fragment D is amplified from genomic *P. pastoris* DNA, starting 200 bp in 3 prime direction of the respective ATG (of the targeted gene) until 1700 bp in 3 prime direction of ATG. Fragment B consists of the first two thirds of the KanMX selection marker cassette and is amplified from pPM2aK21 vector DNA template. Fragment B consists of the last two thirds of the KanMX selection marker cassette and is amplified from pPM2aK21 vector DNA template. Fragments A and B are annealed together (AB) by overlap PCR using the primers A_forward and B_backward. Fragments C and D are annealed together (CD) by overlap PCR using the primers C_forward and D_backward. To generate knock-out strains, a Fab producing host strain was transformed with total 0.5 µg DNA of fragments AB and CD, which both overlap as well. Cells were selected on YPD agar plates containing 500 µg/mL G418. Positive knock-outs clones were verified by PCR using the primer pair check_forward (binds in 5 prime region close to primer sequence A_forward) and check_backward (binds in 3 prime region close to primer sequence D_backward). Due to the replacement of a 400 bp region (around ATG) with a KanMX cassette, PCR product bands of positive knock-out strains are bigger than those of a wild type sequence.

TABLE 6

| Gene identifier | Primer | Sequence |
| --- | --- | --- |
| PP7435_Chr4-0252 | A_forward | CGAACATCCATCACCAAAACAC SEQ ID NO: 132 |
|  | A_backward | GTTGTCGACCTGCAGCGTACGGTGTTGCCGCGAAATG SEQ ID NO: 133 |
|  | B_forward | CATTTCGCGGCAACACCGTACGCTGCAGGTCGACAAC SEQ ID NO: 134 |
|  | B_backward | CGGTGAGAATGGCAAAAGCTTATG SEQ ID NO: 135 |
|  | C_forward | AAGCCCGATGCGCCAGAGTTG SEQ ID NO: 136 |

TABLE 6-continued

| Gene identifier | Primer | Sequence |
|---|---|---|
| | C_backward | CGTCTCTTGGGCAAATTGATCAGTGGATCTGATATCACCTA<br>SEQ ID NO: 137 |
| | D_forward | TAGGTGATATCAGATCCACTGATCAATTTGCCCAAGAGACG<br>SEQ ID NO: 138 |
| | D_backward | GACTGTTGCGATTGCTGGTG<br>SEQ ID NO: 139 |
| | check_forward | ATCCAGGACACGCTCATCAAG<br>SEQ ID NO: 140 |
| | check_backward | GTGTGTGCTCTGGAATTGGATC<br>SEQ ID NO: 141 |
| PP7435_Chr1-0176 | A_forward | AGAGGAGGTTGAATGCGAAGAAG<br>SEQ ID NO: 142 |
| | A_backward | GTTGTCGACCTGCAGCGTACTTCTGGTGAGCTTATATGGCAGTAGTTAC<br>SEQ ID NO: 143 |
| | B_forward | GTAACTACTGCCATATAAGCTCACCAGAAGTACGCTGCAGGTCGACAAC<br>SEQ ID NO: 144 |
| | B_backward | CGGTGAGAATGGCAAAAGCTTATG<br>SEQ ID NO: 145 |
| | C_forward | AAGCCCGATGCGCCAGAGTTG<br>SEQ ID NO: 146 |
| | C_backward | CTCGGGATCACCAAGCACAAGTGGATCTGATATCACCTA<br>SEQ ID NO: 147 |
| | D_forward | TAGGTGATATCAGATCCACTTGTGCTTGGTGATCCCGAG<br>SEQ ID NO: 148 |
| | D_backward | TCAAAGTATGCTGGGAAGAATGG<br>SEQ ID NO: 149 |
| | check_forward | TGGATTGTCTCGGAGGCG<br>SEQ ID NO: 150 |
| | check_backward | TACTATGACTATGGGAGACCTGGGTG<br>SEQ ID NO: 151 |
| PP7435_Chr3-1062 | A_forward | TGAAGCATCCCACCCACTG<br>SEQ ID NO: 152 |
| | A_backward | GTTGTCGACCTGCAGCGTACCCTTCGCAGACTGTAATTATTGGC<br>SEQ ID NO: 153 |
| | B_forward | GCCAATAATTACAGTCTGCGAAGGGTACGCTGCAGGTCGACAAC<br>SEQ ID NO: 154 |
| | B_backward | CGGTGAGAATGGCAAAAGCTTATG<br>SEQ ID NO: 155 |
| | C_forward | AAGCCCGATGCGCCAGAGTTG<br>SEQ ID NO: 156 |
| | C_backward | GTTGACTTTGACGGTTGCAGATACAGTGGATCTGATATCACCTA<br>SEQ ID NO: 157 |
| | D_forward | TAGGTGATATCAGATCCACTGTATCTGCAACCGTCAAAGTCAAC<br>SEQ ID NO: 158 |
| | D_backward | TTCTCTCCTTGATTATCGGTCTCTTTC<br>SEQ ID NO: 159 |
| | check_forward | TGGCAGATGACTTCACAAACG<br>SEQ ID NO: 160 |
| | check_backward | GTGGCATCTTTCATAACGACATCTC<br>SEQ ID NO: 161 |

Example 7

Fed Batch Cultivations

Helper factor engineered strains from Example 5 and 6 with the best performance (increased yield of model protein by at least 1.2 fold change) in the small-scale cultivation were analyzed in fed batch bioreactor cultivations for verification of production host strain improvement. Two protocols were used.
a) Fed Batch Protocol A
The fed batches were carried out in 1.4 L DASGIP reactors (Eppendorf, Germany) with a maximum working volume of 1.0 L. Cultivation temperature was controlled at 25° C., pH was controlled at 5.0 by addition of 25% ammonium hydroxide and the dissolved oxygen concentration was maintained above 20% saturation by controlling the stirrer speed between 400 and 1200 rpm, and the airflow between 24 and 72 sL/h.

The inoculum for the fed batch cultivation was cultivated in shaking flasks containing 100 mL of YP medium containing 20 g/L glycerol and 50 µg/mL Zeocin, and incubated at 28° C. and 180 rpm for approximately 24 hours. The cultures were used to inoculate the starting volume of 0.4 L in the bioreactor to a starting optical density (600 nm) of 1.0. The batch was finished after approximately 24 h and the first (10 mL) salt shot was given.

Glycerol fed batch solution was then fed at a constant rate of 5 mL/h for 5 hours. Then, a methanol pulse (2 g) and a salt shot (10 mL) were given to the culture. After methanol pulse consumption had been indicated by an increase in dissolved oxygen concentration in the culture, a constant feed with methanol fed batch solution was started with a feed rate of 1.0 g/h. Salt shots of 10 mL are given every 10 g of newly formed biomass, that corresponds to ~43 g methanol feed medium. With increasing biomass concentrations, the methanol feed rate was increased appropriately when methanol accumulation could be ruled out due to a sudden increase in dissolved oxygen in the culture when turning off the methanol feed for a short period of time. The final methanol feed rate was 2.5 g/h.

Samples were taken frequently for the determination of biomass and the quantification of Fab (as described in Example 6). The cultivation was harvested after approximately 100 hours when cell densities had reached more than 100 g/L cell dry weight.

The media were as follows:

Batch medium (per litre) contained: 2.0 g citric acid, 12.4 g $(NH_4)_2HPO_4$, 0.022 g $CaCl_2 2H_2O$, 0.9 g KCl, 0.5 g $MgSO_4.7H_2O$, 40 g glycerol, 4.6 mL PTM1 trace salts stock solution. The pH is set to 5.0 with 25% HCl.

Glycerol fed batch solution (per litre) contained: 623 g glycerol, 12 mL PTM1 trace salts stock solution and 40 mg biotin. PTM1 composition is given in Example 1.

Methanol fed batch solution (per litre) of pure methanol contained: 12 mL PTM1 trace salts stock solution and 40 mg biotin.

Salt shot solution (per litre) contained: 20.8 g $MgSO_4.7H_2O$, 41.6 KCl, 1.04 g $CaCl_2 2H_2O$ b) Fed Batch Protocol B Respective strains were inoculated into wide-necked, baffled, covered 300 mL shake flasks filled with 50 mL of YPhyG and shaken at 110 rpm at 28° C. over-night (pre-culture 1). Pre-culture 2 (100 mL YPhyG in a 1000 mL wide-necked, baffled, covered shake flask) was inoculated from pre-culture 1 in a way that the $OD_{600}$ (optical density measured at 600 nm) reached approximately 20 (measured against YPhyG media) in late afternoon (doubling time: approximately 2 hours). Incubation of pre-culture 2 was performed at 110 rpm at 28° C., as well.

The fed batches were carried out in 1.0 L working volume bioreactor (Minifors, Infors, Switzerland). All bioreactors (filled with 400 mL BSM-media with a pH of approximately 5.5) were individually inoculated from pre-culture 2 to an OD600 of 2.0. Generally, P. pastoris was grown on glycerol to produce biomass and the culture was subsequently subjected to glycerol feeding followed by methanol feeding.

In the initial batch phase, the temperature was set to 28° C. Over the period of the last hour before initiating the production phase it was decreased to 25° C. and kept at this level throughout the remaining process, while the pH dropped to 5.0 and was kept at this level. Oxygen saturation was set to 30% throughout the whole process (cascade control: stirrer, flow, oxygen supplementation). Stirring was applied between 700 and 1200 rpm and a flow range (air) of 1.0-2.0 L/min was chosen. Control of pH at 5.0 was achieved using 25% ammonium. Foaming was controlled by addition of antifoam agent Glanapon 2000 on demand.

During the batch phase, biomass was generated (µ~0.30/h) up to a wet cell weight (WCW) of approximately 110-120 g/L. The classical batch phase (biomass generation) would last about 14 hours. A constant glycerol-feed with 6 g/(L*h) was initiated after 11 hours, and lasted 5 hours. The first sampling point was selected to be 16 hours (in the following named as "0 hours" of induction time).

A total of 290 g of methanol was supplied over a period of approximately 95 hours (with a linearly increasing feed rate defined by the equation $1+0.04*t$ (g/L)).

Samples were taken at various time points with the following procedure: the first 3 mL of sampled cultivation broth (with a syringe) were discarded. 1 mL of the freshly taken sample (3-5 mL) was transferred into a 1.5 mL centrifugation tube and spun for 5 minutes at 13,200 rpm (16,100 g). Supernatants were diligently transferred into a separate vial.

1 mL of cultivation broth was centrifuged in a tared Eppendorf vial at 13,200 rpm (16,100 g) for 5 minutes and the resulting supernatant was accurately removed. The vial was weighed (accuracy 0.1 mg), and the tare of the empty vial was subtracted to obtain wet cell weights.

The media were as follows:

YPhyG preculture medium (per litre) contained: 20 g Phytone-Peptone, 10 g Bacto-Yeast Extract, 20 g glycerol Batch medium: Modified Basal salt medium (BSM) (per litre) contained: 13.5 mL $H_3PO_4$ (85%), 0.5 g $CaCl.2H_2O$, 7.5 g $MgSO_4.7H_2O$, 9 g $K_2SO_4$, 2 g KOH, 40 g glycerol, 0.25 g NaCl, 4.35 mL PTM1, 8.7 mg biotin, 0.1 mL Glanapon 2000 (antifoam)

Feed-solution glycerol (per kg) contained: 600 g glycerol, 12 mL PTM1

Feed-solution Methanol contained: pure methanol.

c) Results

Table 7 lists the genes whose overexpression was shown to increase Fab secretion in P. pastoris in fed batch production processes in comparison to the not engineered Fab producing control strains. The Fab product was quantified by ELISA (Example 5c). Biomass was determined as wet cell weight or dry cell weight. Changes in product titers and yields are represented as fold change values relative to the respective control strain. Fold change values show the improvement in titers and product yields in fed batch production processes relative to the AOX HyHEL and AOX SDZ parental hosts which were grown and sampled in parallel for direct comparison.

TABLE 7

| gene identifier | host strain | Fab titer fold change | Fab yield fold change | cultivation time | protocol |
|---|---|---|---|---|---|
| PP7435_Chr3-0933 | CBS7435 pAOX HyHEL | 2.24 | 2.38 | 109 h | B |
| | CBS7435 pAOX SDZ | 1.21 | 1.38 | 111 h | B |

TABLE 7-continued

| gene identifier | host strain | Fab titer fold change | Fab yield fold change | cultivation time | protocol |
|---|---|---|---|---|---|
| PP7435_Chr2-0220 | CBS7435 pAOX HyHEL | 2.48 | 1.91 | 111 h | B |
| | CBS7435 pAOX SDZ | 1.64 | 1.55 | 137 h | A |
| PP7435_Chr3-0639 | CBS7435 pAOX HyHEL | 1.62 | 1.41 | 109 h | B |
| | CBS7435 pAOX SDZ | 1.17 | 1.20 | 111 h | B |
| PP7435_Chr1-1232 | CBS7435 pAOX SDZ | 1.13 | 1.22 | 111 h | B |
| PP7435_Chr1-1225 | CBS7435 pAOX SDZ | 1.39 | 1.74 | 111 h | B |
| PP7435_Chr3-0607 | CBS7435 pAOX HyHEL | 2.28 | 1.67 | 111 h | B |
| | CBS7435 pAOX SDZ | 1.48 | 1.35 | 141 h | A |
| PP7435_Chr4-0448 | CBS7435 pAOX HyHEL | 1.65 | 2.21 | 111 h | B |
| PP7435_Chr4-0108 | CBS7435 pAOX HyHEL | 1.82 | 2.41 | 109 h | B |

As shown, all the listed genes succeeded in increasing the yield (mg/biomass) of the model protein SDZ-Fab or HyHEL-Fab by at least 20% (fold change >1.2) upon overexpression.

Table 8 lists the genes whose deletion was shown to increase Fab secretion in *P. pastoris* in fed batch production processes in comparison to the not engineered Fab producing control strains. The Fab product was quantified by ELISA (Example 5c). Changes in product titers and yields are represented as fold change values relative to the respective control strain.

TABLE 8

| gene identifier | host strain | Fab titer fold change | Fab yield fold change | cultivation time | protocol |
|---|---|---|---|---|---|
| PP7435_Chr4-0252 | CBS7435 pAOX HyHEL | 1.45 | 1.65 | 119 h | A |
| | CBS7435 pAOX SDZ | 1.35 | 1.46 | 113 h | A |
| PP7435_Chr1-0176 | CBS7435 pAOX HyHEL | 1.35 | 1.28 | 111 h | A |
| PP7435_Chr3-1062 | CBS7435 pAOX HyHEL | 1.29 | 2.09 | 89 h | B |

As shown, all the listed genes when underexpressed were able to increase the production in Fab titer (mg/L) or Fab yield (mg/biomass) of the model protein SDZ-Fab or HyHEL-Fab by at least 28% (fold change >1.28).

Examples 8: Combination of HPs and HPs and KO Proteins

For combinations of overexpression targets, CBS7435mutS pAOX SDZ-Fab strains overexpressing either HP3 ('3') or HP10 ('34') under control of the constitutive pGAP promoter (generated as described in Examples 4a and b) were used. For combination of overexpression with underexpression targets, CBS7435mutS pAOX SDZ-Fab strain with a disrupted KO1 gene locus (described in Example 6) was used. In all those strains, the plasmid encoding for the model protein SDZ-Fab were based on Zeocin as selection marker, whereas the plasmids for co-overexpression of the HP or the cassettes used for disruption of the KO gene locus carried the KanMX resistance cassette flanked by co-directional loxP recognition sites.

Prior to transformation with a further HP or KO cassette, the marker gene expression cassette (KanMX flanked by loxP sites) was recycled by Cre recombinase. Therefore, the background strains were transformed with the episomal pTAC_Cre_HphMX4 plasmid, which is expressing Cre recombinase under control of *S. cerevisiae* TPI promoter and is transiently kept in *P. pastoris* as long as selection pressure by hygromycin (Hyg) is present in the culture medium.

Transformants were grown on YPD/Zeo/Hyg agar plates at 28° C. for 2 days, and replica-plated on selective agar plates for growth at 28° C. for further 2 days. Only clones that lost their ability to grow on G418 and on Hyg after 2-3 plating rounds were selected for 24 deep well plate (DWP) screening (described in Example 5 a). Fab titer and yield were determined as described in Example 5c. The best strain in terms of Fab yield and/or titer was then transformed with another plasmid overexpressing a HP protein (described in Examples 4a and b). Transformants with two combined HPs or KOs were selected on selective agar plates (containing Zeo and G418) and screened for Fab secretion as described in Example 5. For further combinatorial steps, the procedure described above was repeated, thus yielding a strain with three combinations and so on. In all screening experiments, the parental (=preceding) strain was used as reference.

The results are as follows—

TABLE 9

| | VS. PARENTAL STRAIN | | VS. ORIGINATING STRAIN | |
| --- | --- | --- | --- | --- |
| | FC TITER average | FC YIELD average | FC TITER average | FC YIELD average |
| HP3 ('3') HP1 ('56') | 2.09 (n = 16) | 1.26 (n = 16) | 1.97 (n = 11) | 1.79 (n = 11) |
| HP10 ('34') HP3 ('3') | 1.63 (n = 16) | 1.6 (n = 16) | n.a. | n.a. |
| KO1 HP2 ('2') HP3 ('3') | 1.51 (n = 8) | 1.33 (n = 8) | n.a. | n.a. |
| KO1 HP2 ('2') HP1 ('56') | 1.42 (n = 8) | 1.33 (n = 8) | n.a. | n.a. |

"Originating strain" means a *P. pastoris* strain pAOX-SDZ-Fab#9 without a HP or without a knock-out, respectively.

"Parental strain" means the SDZ-Fab expressing *P. pastoris* strain serving as host strain for the transformation with the next HP or KO (e.g. a strain only overexpressing HP3 for the combination of HP3 and HP1, a strain having a knock-out of KO1 overexpressing HP2 for the combinations of KO1 HP2 with HP3 or HP1), respectively. It can be seen that each of the combinations leads to an increase of the Fab titer of the model protein SDZ-Fab, both in comparison to the originating strain and the parental strain. The increase of the Fab titer in comparison to the parental strain indicates that combinations of HPs or HPs and KO proteins can even further improve the yield of a POI exemplified by the model protein SDZ-Fab.

The invention claimed is:

1. A recombinant host cell for manufacturing a heterologous protein of interest, wherein the host cell is a yeast and is engineered to underexpress at least one polynucleotide encoding a KO protein having an amino acid sequence as shown in SEQ ID NO: 10, 11, 12 or a functional homologue thereof compared to the host cell prior to genetic manipulation to achieve underexpression, wherein underexpression is achieved by knocking-out the polynucleotide encoding the KO protein or a homologue thereof from the genome of said host cell, disrupting the polynucleotide encoding the KO protein or a homologue thereof in the host cell, disrupting a promoter which is operably linked with said polynucleotide encoding the KO protein or a homologue thereof, replacing the promoter which is operably linked with said polynucleotide encoding the KO protein or a homologue thereof with another promoter which has lower promoter activity, or disrupting expression control sequences of the KO protein or a homologue thereof, wherein the functional homologue has at least 70% sequence identity to an amino acid sequence as shown in SEQ ID NO: 10 or 11 or at least 70% sequence identity to an amino acid sequence as shown in SEQ ID NO: 12, wherein the host cell is engineered to express a heterologous protein of interest.

2. The host cell of claim 1, wherein underexpressing said polynucleotide encoding the KO protein increases the yield of the model protein SDZ-Fab (SEQ ID NO: 25 and 26) and/or HyHEL-Fab (SEQ ID NO: 29 and 30) compared to the host cell prior to engineering.

3. The host cell of claim 1, wherein the host cell is a *Pichia pastoris*, *Hansenula polymorpha*, *Trichoderma reesei*, *Saccharomyces cerevisiae*, *Kluyveromyces lactis*, *Yarrowia lipolytica*, *Pichia methanolica*, *Candida boidinii*, and *Komagataella*, and *Schizosaccharomyces pombe*.

4. The host cell of claim 1, wherein the protein of interest is an enzyme, a therapeutic protein, a food additive, feed additive, or an antibody or antibody fragment.

5. The host cell of claim 1, wherein the host cell is engineered to overexpress at least one polynucleotide encoding a helper protein.

6. The host cell of claim 5, wherein the helper protein has an amino acid sequence as shown in SEQ ID NO: 1, 2, 3, 4, 5, 6, 7, 8, 9, or 162 or a functional homologue thereof, wherein the functional homologue has at least 70% sequence identity to an amino acid sequence as shown in SEQ ID NO: 1, 2, 3, 4, 5, 6, 7, 8, 9, or 162.

7. A yeast host cell obtained by providing a cell which expresses KO protein 1, KO protein 2, and/or KO protein 3, or functional homologue thereof and engineering the cell to underexpress the gene which encodes KO1, KO2 and/or KO3, or functional homologue thereof compared to the yeast host cell prior to genetic manipulation to achieve underexpression, wherein underexpression is achieved by knocking-out the polynucleotide encoding the KO protein or a homologue thereof from the genome of said host cell, disrupting the polynucleotide encoding the KO protein or a homologue thereof in the host cell, disrupting a promoter which is operably linked with said polypeptide encoding the KO protein or a homologue thereof, replacing the promoter which is operably linked with said polypeptide encoding the KO protein or a homologue thereof with another promoter which has lower promoter activity, or disrupting expression control sequences of the KO protein or a homologue thereof, wherein the KO protein has an amino acid sequence as shown in SEQ ID NO: 10, 11 or 12 or the functional homologue has at least 70% sequence identity to an amino acid sequence as shown in SEQ ID NO: 10 or 11 or at least 70% sequence identity to an amino acid sequence as shown in SEQ ID NO: 12, and wherein the host cell is engineered to express a heterologous protein of interest.

8. The host cell of claim 1, wherein the host cell is engineered to
(i) underexpress a polynucleotide encoding a protein having an amino acid as shown in SEQ ID NO: 10 or a functional homologue thereof and further engineered to overexpress a polynucleotide encoding a helper protein having an amino acid sequence as shown in SEQ ID NO: 1 or a functional homologue thereof and a helper protein having an amino acid sequence as shown in SEQ ID NO: 2 or a functional homologue thereof, or
(ii) underexpress a polynucleotide encoding a protein having an amino acid as shown in SEQ ID NO: 10 or a functional homologue thereof and further engineered to overexpress a polynucleotide encoding a helper protein having an amino acid sequence as shown in SEQ ID NO: 4 or a functional homologue thereof and SEQ ID NO: 1 or a functional homologue thereof.

9. A method of increasing the yield of a heterologous protein of interest in a yeast host cell engineered to underexpress at least one polynucleotide encoding a KO protein having an amino acid sequence as shown in SEQ ID NO: 10, 11, 12 or a functional homologue thereof compared to the yeast host cell prior to genetic manipulation to achieve underexpression, comprising underexpressing the at least one polynucleotide encoding the KO protein, wherein the functional homologue has at least 70% sequence identity to an amino acid sequence as shown in SEQ ID NO: 10 or 11 or at least 70% sequence identity to an amino acid sequence as shown in SEQ ID NO: 12.

10. The method of increasing the yield of a heterologous protein of interest in a host cell of claim 9, further comprising:

engineering said host cell to comprise a heterologous polynucleotide encoding a protein of interest, culturing said host cell under suitable conditions to express the protein of interest, and optionally isolating the protein of interest from the cell culture.

11. A method of producing a heterologous protein of interest in a yeast host cell comprising:

providing a yeast host cell engineered to underexpress at least one polynucleotide encoding a KO protein having an amino acid sequence as shown in SEQ ID NO: 10, 11, 12 or a functional homologue thereof compared to the yeast host cell prior to genetic manipulation to achieve underexpression, wherein the functional homologue has at least 70% sequence identity to an amino acid sequence as shown in SEQ ID NO: 10 or 11 or at least 70% sequence identity to an amino acid sequence as shown in SEQ ID NO: 12, wherein said yeast host cell comprises a heterologous polynucleotide encoding a protein of interest;

culturing the yeast host cell under suitable conditions to express the heterologous protein of interest, and optionally isolating the protein of interest from the cell culture.

12. The method of claim 9, wherein the protein of interest is an enzyme, a therapeutic protein, a food additive or feed additive.

13. The method of claim 9, wherein said polynucleotide encoding the KO protein increases the yield of the model protein SDZ-Fab and/or HyHEL-Fab compared to the host cell prior to engineering.

14. The method of claim 11, wherein the protein of interest is an enzyme, a therapeutic protein, a food additive or feed additive.

15. The method of claim 11, wherein said polynucleotide encoding the KO protein increases the yield of the model protein SDZ-Fab and/or HyHEL-Fab compared to the host cell prior to engineering.

16. The host cell of claim 7, wherein the host cell is engineered to (i) underexpress a polynucleotide encoding a protein having an amino acid as shown in SEQ ID NO: 10 or a functional homologue thereof and further engineered to overexpress a polynucleotide encoding a helper protein having an amino acid sequence as shown in SEQ ID NO: 1 or a functional homologue thereof and a helper protein having an amino acid sequence as shown in SEQ ID NO: 2 or a functional homologue thereof, or (ii) underexpress a polynucleotide encoding a protein having an amino acid as shown in SEQ ID NO: 10 or a functional homologue thereof and further engineered to overexpress a polynucleotide encoding a helper protein having an amino acid sequence as shown in SEQ ID NO: 4 or a functional homologue thereof and SEQ ID NO: 1 or a functional homologue thereof.

* * * * *